(12) United States Patent
Small et al.

(10) Patent No.: US 9,586,872 B2
(45) Date of Patent: Mar. 7, 2017

(54) OLEFIN OLIGOMERIZATION METHODS

(75) Inventors: Brooke L. Small, Kingwood, TX (US); Ray Rios, Cypress, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 701 days.

(21) Appl. No.: 13/340,780

(22) Filed: Dec. 30, 2011

(65) Prior Publication Data

US 2013/0172651 A1 Jul. 4, 2013

(51) Int. Cl.
*C07C 2/32* (2006.01)
*C07C 11/02* (2006.01)
*C10G 50/00* (2006.01)
*B01J 31/18* (2006.01)

(52) U.S. Cl.
CPC ............. *C07C 2/32* (2013.01); *B01J 31/1815* (2013.01); *C10G 50/00* (2013.01); *B01J 2231/20* (2013.01); *B01J 2531/0244* (2013.01); *B01J 2531/842* (2013.01); *B01J 2531/845* (2013.01); *C07C 2531/14* (2013.01); *C07C 2531/30* (2013.01)

(58) Field of Classification Search
CPC ....... C07C 2/32; C07C 11/02; C07C 2531/18; C07C 2531/14; C07C 2/08; C07C 2531/28; C10G 50/00
USPC ....... 585/502, 510, 511, 512, 513, 520, 521, 585/522, 523
See application file for complete search history.

(56) References Cited

U.S. PATENT DOCUMENTS

| | | | |
|---|---|---|---|
| 3,635,869 A | 1/1972 | Steele et al. | |
| 3,819,746 A | 6/1974 | Katzakian, Jr. et al. | |
| 3,873,602 A | 3/1975 | Katzakian, Jr. et al. | |
| 3,932,285 A | 1/1976 | Ceprini et al. | |
| 3,962,182 A | 6/1976 | Steele et al. | |
| 3,968,135 A | 7/1976 | Steele et al. | |
| 3,977,996 A | 8/1976 | Katzakian, Jr. et al. | |
| 3,978,026 A | 8/1976 | Katzakian, Jr. et al. | |
| 4,017,429 A | 4/1977 | Steele et al. | |
| 4,057,565 A | 11/1977 | Manzer | |

(Continued)

FOREIGN PATENT DOCUMENTS

| | | |
|---|---|---|
| AU | 650808 | 6/1994 |
| CA | 2087578 A1 | 7/1994 |

(Continued)

OTHER PUBLICATIONS

CRC Handbook of Chemistry and Physics, 95th edition, 2015 Internet Version, D. R. Lide, ed.—month unknown.*

(Continued)

*Primary Examiner* — In Suk Bullock
*Assistant Examiner* — Ali Z Fadhel
(74) *Attorney, Agent, or Firm* — Conley Rose, P.C.; Rodney B. Carroll; Lynda Jolly

(57) ABSTRACT

Processes for oligomerizing olefins utilizing a catalyst system including a) a transition metal complex that is transition metal compound complexed to a pyridine bisimine ligand and b) a metal alkyl and controlling the olefin oligomer product distribution K value by adjusting i) a transition metal of the transition metal complex concentration in the reactor, ii) a metal of the metal alkyl concentration in the reactor, iii) a metal of the metal alkyl to transition metal of the transition metal complex molar ratio in the reactor, and iv) any combination thereof.

22 Claims, 2 Drawing Sheets

(56) References Cited

U.S. PATENT DOCUMENTS

| | | | |
|---|---|---|---|
| 4,451,573 A | 5/1984 | Ikegami et al. |
| 4,668,838 A | 5/1987 | Briggs |
| 4,777,315 A | 10/1988 | Levine et al. |
| 4,853,356 A | 8/1989 | Briggs |
| 4,876,229 A | 10/1989 | Furtek |
| 4,971,986 A | 11/1990 | Stanek et al. |
| 5,081,089 A | 1/1992 | Rekers et al. |
| 5,118,648 A | 6/1992 | Furtek et al. |
| 5,137,994 A | 8/1992 | Goode et al. |
| 5,198,401 A | 3/1993 | Turner et al. |
| 5,198,563 A | 3/1993 | Reagen et al. |
| 5,288,823 A | 2/1994 | Reagan et al. |
| 5,331,070 A | 7/1994 | Pettijohn et al. |
| 5,331,104 A | 7/1994 | Reagen et al. |
| 5,340,785 A | 8/1994 | Reagen et al. |
| 5,340,892 A | 8/1994 | Kuramoto |
| 5,360,879 A | 11/1994 | Reagen et al. |
| 5,376,612 A | 12/1994 | Reagen et al. |
| 5,382,738 A | 1/1995 | Reagen et al. |
| 5,393,719 A | 2/1995 | Pettijohn et al. |
| 5,399,539 A | 3/1995 | Reagen et al. |
| 5,438,027 A | 8/1995 | Reagen et al. |
| 5,451,645 A | 9/1995 | Reagen et al. |
| 5,470,926 A | 11/1995 | Reagen et al. |
| 5,491,272 A | 2/1996 | Tanaka et al. |
| 5,523,507 A | 6/1996 | Reagen et al. |
| 5,543,375 A | 8/1996 | Lashier et al. |
| 5,550,305 A | 8/1996 | Wu |
| 5,557,026 A | 9/1996 | Tanaka et al. |
| 5,563,312 A | 10/1996 | Knudsen et al. |
| 5,689,028 A | 11/1997 | Lashier et al. |
| 5,696,240 A | 12/1997 | Vallarino et al. |
| 5,714,556 A | 2/1998 | Johnson et al. |
| 5,731,487 A | 3/1998 | Tamura et al. |
| 5,744,677 A | 4/1998 | Wu |
| 5,750,816 A | 5/1998 | Araki et al. |
| 5,750,817 A | 5/1998 | Tanaka et al. |
| 5,763,723 A | 6/1998 | Reagen et al. |
| 5,786,291 A | 7/1998 | Speca et al. |
| 5,786,431 A | 7/1998 | Reagen et al. |
| 5,811,618 A | 9/1998 | Wu |
| 5,814,575 A | 9/1998 | Reagen et al. |
| 5,830,955 A | 11/1998 | Takeda et al. |
| 5,856,257 A | 1/1999 | Freeman et al. |
| 5,856,610 A | 1/1999 | Tamura et al. |
| 5,856,612 A | 1/1999 | Araki et al. |
| 5,859,303 A | 1/1999 | Lashier |
| 5,880,241 A | 3/1999 | Brookhart et al. |
| 5,910,619 A | 6/1999 | Urata et al. |
| 5,919,996 A | 7/1999 | Freeman et al. |
| 5,955,555 A | 9/1999 | Bennett |
| 5,968,866 A | 10/1999 | Wu |
| 5,986,153 A | 11/1999 | Kallenbach et al. |
| 6,031,145 A | 2/2000 | Commereuc et al. |
| 6,063,881 A | 5/2000 | Bennett |
| 6,103,654 A | 8/2000 | Commereuc et al. |
| 6,103,658 A | 8/2000 | Mackenzie et al. |
| 6,103,946 A | 8/2000 | Brookhart, III et al. |
| 6,127,301 A | 10/2000 | Iwanaga et al. |
| 6,133,495 A | 10/2000 | Urata et al. |
| 6,150,482 A | 11/2000 | Brookhart et al. |
| 6,184,428 B1 | 2/2001 | Zahoor et al. |
| 6,214,761 B1 | 4/2001 | Bennett |
| 6,221,986 B1 | 4/2001 | Commereuc et al. |
| 6,239,237 B1 | 5/2001 | Xu et al. |
| 6,281,303 B1 | 8/2001 | Lavoie et al. |
| 6,291,733 B1 | 9/2001 | Small et al. |
| 6,337,297 B1 | 1/2002 | Mimura et al. |
| 6,344,594 B1 | 2/2002 | Sen et al. |
| 6,369,177 B1 | 4/2002 | Tohi et al. |
| 6,380,451 B1 | 4/2002 | Kreischer et al. |
| 6,399,535 B1 | 6/2002 | Shih et al. |
| 6,407,188 B1 | 6/2002 | Guan et al. |
| 6,414,098 B1 | 7/2002 | Engehausen et al. |
| 6,417,305 B2 | 7/2002 | Bennett |
| 6,417,364 B1 | 7/2002 | Lenges |
| 6,423,848 B2 | 7/2002 | Bennett |
| 6,432,862 B1 | 8/2002 | Bennett |
| 6,451,939 B1 | 9/2002 | Britovsek et al. |
| 6,455,648 B1 | 9/2002 | Freeman et al. |
| 6,455,660 B1 | 9/2002 | Clutton et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,465,386 B1 | 10/2002 | Maddox et al. |
| 6,472,341 B1 | 10/2002 | Kimberley et al. |
| 6,489,497 B1 | 12/2002 | Brookhart, III et al. |
| 6,521,806 B1 | 2/2003 | Tamura et al. |
| 6,534,691 B2 * | 3/2003 | Culver et al. ............... 585/527 |
| 6,545,108 B1 | 4/2003 | Moody et al. |
| 6,548,672 B1 | 4/2003 | Gibson et al. |
| 6,555,633 B1 | 4/2003 | Tanaka et al. |
| 6,555,723 B2 | 4/2003 | Schiffino |
| 6,559,091 B1 | 5/2003 | Moody et al. |
| 6,562,973 B1 | 5/2003 | Liu |
| 6,657,026 B1 | 12/2003 | Kimberley et al. |
| 6,683,141 B1 | 1/2004 | Gibson et al. |
| 6,683,187 B2 * | 1/2004 | De Boer et al. ............ 546/345 |
| 6,689,848 B2 | 2/2004 | Nagy et al. |
| 6,710,006 B2 | 3/2004 | De Boer et al. |
| 6,720,468 B2 | 4/2004 | Elomari et al. |
| 6,740,715 B2 | 5/2004 | Brookhart, III et al. |
| 6,777,584 B2 | 8/2004 | Patil et al. |
| 6,787,499 B2 | 9/2004 | Tanaka et al. |
| 6,818,715 B1 | 11/2004 | Kristen et al. |
| 6,825,297 B1 | 11/2004 | Devore et al. |
| 6,828,269 B2 | 12/2004 | Commereuc et al. |
| 6,841,693 B1 | 1/2005 | Watanabe et al. |
| 6,844,290 B1 | 1/2005 | Maas et al. |
| 6,894,134 B2 | 5/2005 | Brookhart et al. |
| 6,900,152 B2 | 5/2005 | Yoshida et al. |
| 6,903,042 B2 | 6/2005 | Drochon et al. |
| 6,911,505 B2 | 6/2005 | Small |
| 6,911,506 B2 | 6/2005 | Small et al. |
| 6,927,313 B2 | 8/2005 | Bianchini et al. |
| 7,001,964 B2 | 2/2006 | Small |
| 7,037,988 B2 | 5/2006 | De Boer et al. |
| 7,045,632 B2 | 5/2006 | Small |
| 7,049,442 B2 * | 5/2006 | De Boer et al. ............ 546/268.1 |
| 7,053,020 B2 * | 5/2006 | De Boer et al. ............ 502/155 |
| 7,053,259 B2 | 5/2006 | Culver et al. |
| 7,056,997 B2 | 6/2006 | Small et al. |
| 7,129,304 B1 | 10/2006 | Small et al. |
| 7,176,266 B2 | 2/2007 | Sato et al. |
| 7,179,871 B2 | 2/2007 | De Boer et al. |
| 7,223,893 B2 | 5/2007 | Small et al. |
| 7,238,764 B2 | 7/2007 | De Boer et al. |
| 7,268,096 B2 | 9/2007 | Small et al. |
| 7,271,121 B2 | 9/2007 | Small et al. |
| 7,297,806 B2 | 11/2007 | Brookhart, III et al. |
| 7,304,159 B2 | 12/2007 | De Boer et al. |
| 7,384,886 B2 | 6/2008 | Knudsen et al. |
| 7,442,819 B2 | 10/2008 | Ionkin et al. |
| 7,456,284 B2 | 11/2008 | Small |
| 7,589,245 B2 | 9/2009 | Maria De Boer et al. |
| 7,683,149 B2 | 3/2010 | Ionkin et al. |
| 7,727,926 B2 | 6/2010 | Small et al. |
| 7,728,160 B2 | 6/2010 | Small et al. |
| 7,728,161 B2 | 6/2010 | Small et al. |
| 7,820,581 B2 | 10/2010 | Knudsen et al. |
| 7,902,415 B2 | 3/2011 | Small |
| 7,906,451 B2 | 3/2011 | Citron et al. |
| 7,910,670 B2 | 3/2011 | Knudsen et al. |
| 7,977,269 B2 | 7/2011 | Small et al. |
| 7,994,376 B2 | 8/2011 | Small et al. |
| 8,076,523 B2 * | 12/2011 | Bollmann et al. ............ 585/513 |
| 8,329,608 B2 | 12/2012 | Knudsen et al. |
| 2001/0053742 A1 | 12/2001 | Knudsen et al. |
| 2004/0122269 A1 | 6/2004 | Van Zon et al. |
| 2004/0122271 A1 | 6/2004 | Van Zon et al. |
| 2004/0143147 A1 | 7/2004 | Ittel et al. |
| 2005/0187098 A1 | 8/2005 | Knudsen et al. |
| 2005/0187418 A1 | 8/2005 | Small et al. |

(56) References Cited

U.S. PATENT DOCUMENTS

| | | | |
|---|---|---|---|
| 2007/0043181 A1 | 2/2007 | Knudsen et al. | |
| 2009/0270567 A1* | 10/2009 | Small et al. | 526/64 |
| 2011/0021343 A1 | 1/2011 | Knudsen et al. | |

FOREIGN PATENT DOCUMENTS

| | | |
|---|---|---|
| CA | 2396614 A1 | 7/2001 |
| CA | 2115639 C | 10/2004 |
| CA | 2556879 A1 | 9/2005 |
| CA | 2664894 A1 | 9/2005 |
| CA | 2745808 A1 | 9/2005 |
| CA | 2619226 A1 | 3/2007 |
| CN | 1108967 A | 9/1995 |
| CN | 1256968 A | 6/2000 |
| CN | 1294109 A | 5/2001 |
| CN | 1306014 A | 8/2001 |
| CN | 1358772 A | 7/2002 |
| CN | 1361093 A | 7/2002 |
| CN | 1374281 A | 10/2002 |
| CN | 1433433 A | 7/2003 |
| CN | 1651142 A | 8/2005 |
| CN | 1850339 A | 10/2006 |
| DE | 19812066 A1 | 1/1999 |
| EP | 0416815 A2 | 3/1991 |
| EP | 0537609 A2 | 4/1993 |
| EP | 0608447 A1 | 8/1994 |
| EP | 0668105 A2 | 8/1995 |
| EP | 1110930 A1 | 6/2001 |
| EP | 1188762 A1 | 3/2002 |
| EP | 1229020 A1 | 8/2002 |
| EP | 1325924 A1 | 7/2003 |
| EP | 1716089 A1 | 11/2006 |
| EP | 1719747 A1 | 11/2006 |
| EP | 1723092 A1 | 11/2006 |
| EP | 1904509 A2 | 4/2008 |
| EP | 1931469 A1 | 6/2008 |
| EP | 2284142 A2 | 2/2011 |
| EP | 2287143 A2 | 2/2011 |
| EP | 2287144 A2 | 2/2011 |
| ES | 2018110 A6 | 3/1991 |
| FR | 2833191 A1 | 6/2003 |
| FR | 2857964 A1 | 1/2005 |
| JP | 6263822 | 9/1994 |
| JP | 7010780 | 1/1995 |
| JP | 7017878 | 1/1995 |
| JP | 7018013 | 1/1995 |
| JP | 7118173 | 5/1995 |
| JP | 7118174 | 5/1995 |
| JP | 7118175 | 5/1995 |
| JP | 7118324 | 5/1995 |
| JP | 7118325 | 5/1995 |
| JP | 7118326 | 5/1995 |
| JP | 7118327 | 5/1995 |
| JP | 7118328 | 5/1995 |
| JP | 7149671 | 6/1995 |
| JP | 7149672 | 6/1995 |
| JP | 7149673 | 6/1995 |
| JP | 7149674 | 6/1995 |
| JP | 7149675 | 6/1995 |
| JP | 7149676 | 6/1995 |
| JP | 7149677 | 6/1995 |
| JP | 7157512 | 6/1995 |
| JP | 7215896 | 8/1995 |
| JP | 8059732 | 3/1996 |
| JP | 8134131 | 5/1996 |
| JP | 8151409 | 6/1996 |
| JP | 8183747 | 7/1996 |
| JP | 8239330 | 9/1996 |
| JP | 8239331 | 9/1996 |
| JP | 8239418 | 9/1996 |
| JP | 8245429 | 9/1996 |
| JP | 8245430 | 9/1996 |
| JP | 8245431 | 9/1996 |
| JP | 8283330 | 10/1996 |
| JP | 8283332 | 10/1996 |
| JP | 8301921 | 11/1996 |
| JP | 8301922 | 11/1996 |
| JP | 8301923 | 11/1996 |
| JP | 8301924 | 11/1996 |
| JP | 8301925 | 11/1996 |
| JP | 8325317 | 12/1996 |
| JP | 8325318 | 12/1996 |
| JP | 8325319 | 12/1996 |
| JP | 8333407 | 12/1996 |
| JP | 9012627 | 1/1997 |
| JP | 9020692 | 1/1997 |
| JP | 9020693 | 1/1997 |
| JP | 9040710 | 2/1997 |
| JP | 9087318 | 3/1997 |
| JP | 9143213 | 6/1997 |
| JP | 9176228 | 7/1997 |
| JP | 9176229 | 7/1997 |
| JP | 9188634 | 7/1997 |
| JP | 9194400 | 7/1997 |
| JP | 9194524 | 7/1997 |
| JP | 9262480 | 10/1997 |
| JP | 9268133 | 10/1997 |
| JP | 9268134 | 10/1997 |
| JP | 9268135 | 10/1997 |
| JP | 10007593 | 1/1998 |
| JP | 10007594 | 1/1998 |
| JP | 10007595 | 1/1998 |
| JP | 10007681 | 1/1998 |
| JP | 10036431 | 2/1998 |
| JP | 10036432 | 2/1998 |
| JP | 10036433 | 2/1998 |
| JP | 10036435 | 2/1998 |
| JP | 10045634 | 2/1998 |
| JP | 10045638 | 2/1998 |
| JP | 10045833 | 2/1998 |
| JP | 10060043 | 3/1998 |
| JP | 10087517 | 4/1998 |
| JP | 10087518 | 4/1998 |
| JP | 10101587 | 4/1998 |
| JP | 10218799 | 8/1998 |
| JP | 11060511 | 3/1999 |
| JP | 11060626 | 3/1999 |
| JP | 11092407 | 4/1999 |
| JP | 11092408 | 4/1999 |
| JP | 2000176291 | 6/2000 |
| JP | 2000202299 | 7/2000 |
| JP | 2000212212 | 8/2000 |
| JP | 2001002724 | 1/2001 |
| JP | 2001009290 | 1/2001 |
| JP | 2001096164 | 4/2001 |
| JP | 2001149788 | 6/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233764 | 8/2002 |
| JP | 2002233765 | 8/2002 |
| JP | 2002371062 A | 12/2002 |
| JP | 2003071294 | 3/2003 |
| JP | 2003088760 | 3/2003 |
| JP | 2003147009 A | 5/2003 |
| JP | 2004136270 | 5/2004 |
| JP | 2004136271 | 5/2004 |
| JP | 2004306014 | 11/2004 |
| KR | 20030029253 | 4/2003 |
| WO | 9415940 A1 | 7/1994 |
| WO | 9611193 A1 | 4/1996 |
| WO | 9623010 A2 | 8/1996 |
| WO | 9821171 A1 | 5/1998 |
| WO | 9827124 A1 | 6/1998 |
| WO | 9919280 A1 | 4/1999 |
| WO | 9950318 A1 | 10/1999 |
| WO | 9962963 A1 | 12/1999 |
| WO | 9962967 A2 | 12/1999 |
| WO | 0020427 A1 | 4/2000 |
| WO | 0037175 A1 | 6/2000 |

(56) References Cited

FOREIGN PATENT DOCUMENTS

| | | |
|---|---|---|
| WO | 0058320 A1 | 10/2000 |
| WO | 0066638 A1 | 11/2000 |
| WO | 0068280 A1 | 11/2000 |
| WO | 0069923 A1 | 11/2000 |
| WO | 0110875 A1 | 2/2001 |
| WO | 0123443 A1 | 4/2001 |
| WO | 0136379 A1 | 5/2001 |
| WO | 0136503 A1 | 5/2001 |
| WO | 0138270 A1 | 5/2001 |
| WO | 0147839 A1 | 7/2001 |
| WO | 0148028 A1 | 7/2001 |
| WO | 0158874 A1 | 8/2001 |
| WO | 0168572 A1 | 9/2001 |
| WO | 0168725 A2 | 9/2001 |
| WO | 0174830 A1 | 10/2001 |
| WO | 0183446 A1 | 11/2001 |
| WO | 0183447 A2 | 11/2001 |
| WO | 0200339 A2 | 1/2002 |
| WO | 0204119 A1 | 1/2002 |
| WO | 0210133 A1 | 2/2002 |
| WO | 0228805 A2 | 4/2002 |
| WO | 0234701 A1 | 5/2002 |
| WO | 0234746 A2 | 5/2002 |
| WO | 02066404 A1 | 8/2002 |
| WO | 02066405 A1 | 8/2002 |
| WO | 02079276 A2 | 10/2002 |
| WO | 02083306 A2 | 10/2002 |
| WO | 02083306 A3 | 10/2002 |
| WO | 02090365 A1 | 11/2002 |
| WO | 02096919 A1 | 12/2002 |
| WO | 03004158 A2 | 1/2003 |
| WO | 03010207 A1 | 2/2003 |
| WO | 03011876 A1 | 2/2003 |
| WO | 03022889 A1 | 3/2003 |
| WO | 03024902 A1 | 3/2003 |
| WO | 03053890 A1 | 7/2003 |
| WO | 03053891 A1 | 7/2003 |
| WO | 03059511 A1 | 7/2003 |
| WO | 03072529 A1 | 9/2003 |
| WO | 2004026795 A2 | 4/2004 |
| WO | 2004029012 A1 | 4/2004 |
| WO | 2004033398 A1 | 4/2004 |
| WO | 2004043887 A2 | 5/2004 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2004078799 A1 | 9/2004 |
| WO | 2005080301 A1 | 9/2005 |
| WO | 2005082816 A1 | 9/2005 |
| WO | 2005092821 A1 | 10/2005 |
| WO | 2005111099 A1 | 11/2005 |
| WO | 2006008438 A1 | 1/2006 |
| WO | 2006016101 A1 | 2/2006 |
| WO | 2006065458 A2 | 6/2006 |
| WO | 2006065458 A3 | 6/2006 |
| WO | 2007013931 A2 | 2/2007 |
| WO | 2007013931 A3 | 2/2007 |
| WO | 2007021955 A2 | 2/2007 |
| WO | 2007024504 A1 | 3/2007 |
| WO | 2007059015 A1 | 5/2007 |
| WO | 2007080081 A2 | 7/2007 |
| WO | 2008038173 A2 | 4/2008 |
| WO | 2009085886 A1 | 7/2009 |
| WO | 2009085411 A1 | 11/2009 |

OTHER PUBLICATIONS

Britovesk et al. "Oligomerization of Ethylene by Bis(imino)pyridyliron and -cobalt Complexes", Chem. Eur. J. 2000, 6, No. 12.*
Bianchini et al. "Ethylene oligomerization, homopolymerization and copolymerization by iron and cobalt catalysts with 2,6-(bis-organylimino)pyridiyl ligands", Coordination Chemistry Reviews 250 (2006) 1391-1418.*
Bennett, Alison M. A., "Novel, highly active iron and cobalt catalysts for olefin polymerization," Chemtech, Jul. 1999, pp. 24-28, vol. 29, No. 7, American Chemical Society.
Britovsek, George J. P., et al., "Novel Olefin Polymerization Catalysts Based on Iron and Cobalt," Chem. Commun., 1998, pp. 849-850.
Britovsek, George J. P., et al., "Iron and Cobalt Ethylene Polymerization Catalysts Bearing 2,6-Bis(Imino) Pyridyl Ligands: Synthesis, Structures, and Polymerization Studies," J. Am. Chem. Soc., 1999, pp. 8728-8740, vol. 121, No. 38, American Chemical Society.
Zhang, Zhicheng, et al., "Ethylene oligomerization catalyzed by a novel iron complex containing fluoro and methyl substituents," Journal of Molecular Catalysis A: Chemical, 2004, pp. 249-254, vol. 219, Elsevier B.V.
Foreign communication from a related counterpart application—International Search Report and Written Opinion, PCT/US2012/067066 dated Mar. 13, 2013, 11 pages.
Beck, Wolfgang, et al., "Metal complexes of weakly coordination anions. Precursors of strong cationic organometallic Lewis acids," Chemical Reviews, 1988, pp. 1405-1421, vol. 88, No. 7, American Chemical Society.
Chang, Sechin, et al., "Model complexes of the active site in peptide deformylase: a new family of mononuclear N2S-M(II) complexes," Inorg. Chem. 2001, pp. 194-195, vol. 40, No. 2, American Chemical Society.
Chen, Yaofeng, et al., "Fluoro-substituted 2,6-bis(imino)pyridyl iron and cobalt complexes: high-activity ethylene oligomerization catalysts," Organometallics, 2003, pp. 1231-1236, vol. 22, No. 6, American Chemical Society.
Chen, Yaofeng, "Halogen-substituted 2,6-bis(imino)pyridyl iron and cobalt complexes: highly active catalysts for polymerization and oligomerization of ethylene," Organometallics, 2003, pp. 4312-4321, vol. 22, No. 21, American Chemical Society.
Dubois, Thomas D., "Four- and five-coordinate nickel(II) complexes of 2,3-butanedionebis(2-diphenylphosphinoethylimine)," Inorganic Chemistry, 1972, pp. 718-722, vol. 11, No. 4.
Foreign communication from a related counterpart application—Australian Examination Report, AU2005217601, May 25, 2010, 4 pages.
Foreign communication from a related counterpart application—Invitation to Pay Additional Fees, PCT/US2006/028068, Jan. 5, 2007, 6 pages.
Foreign communication from a related counterpart application—Canadian Office Action, CA2556879, Apr. 1, 2008, 3 pages.
Foreign communication from a related counterpart application—Canadian Office Action, CA2556879, Nov. 13, 2008, 3 pages.
Foreign communication from a related counterpart application—Canadian Office Action, CA2556879, Jul. 16, 2009, 2 pages.
Foreign communication from a related counterpart application—Canadian Office Action, CA2619226, Sep. 21, 2012, 2 pages.
Foreign communication from a related counterpart application—Canadian Office Action, CA2664894, Sep. 14, 2009, 3 pages.
Foreign communication from a related counterpart application—Canadian Office Action, CA2664894, Apr. 30, 2010, 4 pages.
Foreign communication from a related counterpart application—Canadian Office Action, CA2745808, Oct. 3, 2011, 2 pages.
Foreign communication from a related counterpart application—Canadian Office Action, CA2745808, Oct. 30, 2012, 3 pages.
Foreign communication from a related counterpart application—Chinese First Office Action, CN200580012496.3, Nov. 28, 2008, 8 pages.
Foreign communication from a related counterpart application—Chinese Second Office Action, CN200580012496.3, Jul. 24, 2009, 4 pages.
Foreign communication from a related counterpart application—Chinese Third Office Action, CN200580012496.3, Nov. 6, 2009, 4 pages.
Foreign communication from a related counterpart application—Chinese Fourth Office Action, CN200580012496.3, May 16, 2011, 5 pages.

(56) References Cited

OTHER PUBLICATIONS

Foreign communication from a related counterpart application—Chinese Rejection Decision, CN200580012496.3, Sep. 14, 2011, 2 pages.
Foreign communication from a related counterpart application—Chinese Fifth Office Action, CN200580012496.3, May 2, 2012, 5 pages.
Foreign communication from a related counterpart application—Chinese Sixth Office Action, CN200580012496.3, Nov. 27, 2012, 3 pages.
Foreign communication from a related counterpart application—Chinese First Office Action, CN200680033897.1, Dec. 31, 2010, 6 pages.
Foreign communication from a related counterpart application—Chinese Second Office Action, CN200680033897.1, Jun. 24, 2011, 6 pages.
Foreign communication from a related counterpart application—Chinese Third Office Action, CN200680033897.1, Nov. 1, 2011, 5 pages.
Foreign communication from a related counterpart application—Chinese First Office Action, CN200680038895.1, Jan. 15, 2010, 7 pages.
Foreign communication from a related counterpart application—Chinese Second Office Action, CN200680038895.1, Oct. 8, 2010, 3 pages.
Foreign communication from a related counterpart application—Chinese Third Office Action, CN200680038895.1, Oct. 25, 2011, 6 pages.
Foreign communication from a related counterpart application—Chinese First Office Action, CN200910148885.9, Jul. 3, 2012, 16 pages.
Foreign communication from a related counterpart application—Chinese Second Office Action, CN200910148885.9, Apr. 1, 2013, 7 pages.
Foreign communication from a related counterpart application—International Search Report and Written Opinion, PCT/US2006/028068, Jun. 20, 2007, 15 pages.
Foreign communication from a related counterpart application—European Examination Report, EP05723396.7, Mar. 8, 2010, 3 pages.
Foreign communication from a related counterpart application—European Examination Report, EP06787885.0, Apr. 17, 2009, 7 pages.
Foreign communication from a related counterpart application—European Examination Report, EP06787885.0, Apr. 9, 2010, 3 pages.
Foreign communication from a related counterpart application—European Examination Report, EP06801210.3, Oct. 12, 2009, 4 pages.
Foreign communication from a related counterpart application—European Search Report, EP10183724.3, Jan. 27, 2012, 6 pages.
Foreign communication from a related counterpart application—European Search Report, EP10183728.4, Jan. 26, 2012, 7 pages.
Foreign communication from a related counterpart application—European Search Report, EP10183732.6, Jan. 27, 2012, 5 pages.
Foreign communication from a related counterpart application—Gulf Cooperation Council (GCC) Search Report with Examination Report, GCC/P/2006/6589, Dec. 23, 2010, 8 pages.
Foreign communication from a related counterpart application—Gulf Cooperation Council (GCC) Examination Report with Search Report, GCC/P/2006/6720, Jun. 28, 2009, 15 pages.
Foreign communication from a related counterpart application—International Preliminary Report on Patentability, PCT/US2004/004472, Sep. 9, 2005, 5 pages.
Foreign communication from a related counterpart application—International Preliminary Report on Patentability, PCT/US2006/031303, Aug. 20, 2008, 7 pages.
Advisory Action dated May 21, 2009 (3 pages), U.S. Appl. No. 11/207,232, filed Aug. 19, 2005.
Foreign communication from a counterpart application—European Examination Report, EP05723401.5, May 4, 2010, 7 pages.
Foreign communication from a counterpart application—Australian Examination Report, AU2006283779, Jun. 11, 2010, 2 pages.
Foreign communication from a counterpart application—Mexican Office Action, MX2006/009474, Dec. 17, 2008, 4 pages.
Foreign communication from a counterpart application—Singapore Office Action, SG200605612-1, Jun. 12, 2008, 6 pages.
Ionkin, Alex S., et al., "High-temperature catalysts for the production of a-olefins based on iron(II) and iron(III) tridentate bis(imino)pyridine complexes with double pattern of substitution: ortho-methyl plus meta-aryl," Organometallics, 2006, pp. 2978-2992, vol. 25, No. 12, American Chemical Society.
Ionkin, Alex S., et al., "High-temperature catalysts for the production of a-olefins based on iron(II) and iron(III) tridentate bis(imino)pyridine complexes modified by nitrilo group," Journal of Polymer Science: Part A: Polymer Chemistry, 2008, pp. 585-611, vol. 46, Wiley Periodicals, Inc.
Ionkin, Alex S., et al., "High-temperature catalysts for the production of a-olefins based on iron(II) and cobalt(II) tridentate bis(imino)pyridine complexes with double pattern of substitution: o-methyl plus o-fluorine in the same imino arm," Organometallics, 2008, pp. 1147-1156, vol. 27, No. 6, American Chemical Society.
Ionkin, Alex S., et al., "Modification of iron(II) tridentate bis(imino)pyridine complexes by a boryl group for the production of a-olefins at high temperature," Organometallics, 2008, pp. 1902-1911, vol. 27, No. 8, American Chemical Society.
Katritzky, Alan R., et al., "Syntheses of 1,4-benzothiazepines and 1,4-benzoxazepines via cyclizations of 1-[2-arylthio(oxy)ethyl]-5-benzotriazolyl-2-pyrrolidinones and 3-benzotriazolyl-2[2-arylthio(oxy)ethyl]-1-isoindolinones," J. Org. Chem. 2001, pp. 5590-5594, vol. 66, No. 16, American Chemical Society.
McNaught, Alan D., et al., Compendium of chemical terminology, IUPAC recommendations, Second Edition, 1997, 4 pages, Wiley-Blackwell.
Periodic table of the elements, Feb. 4, 1985, pp. 26-27, C&EN.
Rosenberger, Volker, et al., "Diazadien-komplexe des rutheniums," XP-002410474, Journal of Organometallic Chemistry, 1991, pp. 445-456, vol. 411, Elsevier Sequoia S.A., Lausanne.
Small, Brooke L., et al., "Comparative dimerization of 1-butene with a variety of metal catalysts, and the investigation of a new catalyst for C—H bond activation," Chem. Eur. J., 2004, pp. 1014-1020 plus 4 pages of supporting information, vol. 10, Wiley-VCH Verlag GmbH & Co. KGaA, Weinheim.
Small, Brooke L., et al., "New chromium complexes for ethylenen oligomerization: extended use of tridentate ligands in metal-catalyzed olefin polymerization," Macromolecules, 2004, pp. 4375-4386, vol. 37, No. 12, American Chemical Society.
Small, Brooke L., et al., "New iron and cobalt catalysts for the polymerization of olefins," 1 page.
Stojcevic Goran, et al., "Coordination insertion reactions of acrylonitrile into Pd—H and Pd—methyl bonds in a diimine-palladium(II) system," XP-002410475, Journal of Organometallic Chemistry, 2005, pp. 4349-4355, vol. 690, Elsevier B.V.
Stollenz, Michael, et al., "Complexes of nickel(II) with oxalic amidines and oxalic amidinates with additional R2P-donor groups," Z. Anorg. Allg. Chem., 2004, pp. 2701-2708, vol. 630, Wiley-VCH Verlag GmbH & Co. KGaA, Weinheim.
Strauss, Steven H., "The search for larger and more weakly coordinating anions," Chem. Rev., 1993, pp. 927-942, vol. 93, No. 3, American Chemical Society.
Tempel, Daniel J., et al., Mechanistic studies of Pd(II)—a-diimine-catalyzed olefin polymerizations, XP-002410476, J. Am. Chem. Soc., 2000, pp. 6686-6700, vol. 122, No. 28, American Chemical Society.
Wang, Sheena Hallin, et al., "Catalytic sulfoxidation and epoxidation with a Mn(III) triazacorrole: evidence for a "third oxidant" in high-valent porphyrinold oxidations," J. Am. Chem. Soc., 2004, pp. 18-19, vol. 126,No. 1, American Chemical Society.
Foreign communication from a related counterpart application—International Preliminary Report on Patentability, PCT/US2005/005437, Aug. 22, 2006, 10 pages.

(56) References Cited

OTHER PUBLICATIONS

Foreign communication from a related counterpart application—International Preliminary Report on Patentability, PCT/US2005/042175, Jun. 13, 2007, 6 pages.
Foreign communication from a related counterpart application—International Preliminary Report on Patentability, PCT/US2006/028068, Jan. 22, 2008, 9 pages.
Foreign communication from a related counterpart application—International Preliminary Report on Patentability, PCT/US2008/083026, Jun. 22, 2010, 6 pages.
Adams, Harry, et al., "Complexes of ligands providing endogenous bridges. Part 1. The syntheses and crystal structures of barium and lead(II) complexes of macrocyclic schiff bases derived from heterocyclic dicarbonyls and 1,n-diamino-n'-hydroxyalkanes (n,n'=3,2; 4,2; or 5,3)," XP009070491, 1987, pp. 207-218, J. Chem. Soc. Dalton Trans.
Advisory Action dated Aug. 9, 2006 (3 pages), U.S. Appl. No. 10/783,429, filed Feb. 20, 2004.
Advisory Action dated Mar. 29, 2007 (3 pages), U.S. Appl. No. 10/783,429, filed Feb. 20, 2004.
Allen, Geoffrey, Editor, "Comprehensive polymer science, vol. 4," 1989, pp. 1-108, 409-412, 533-584 plus 1 cover page, 2 publishing pages, and 2 contents pages, Pergamon Press, England.
Boor, Jr., John, "Ziegler-natta catalysts and polymerizations,"1979, 1 cover page and 1 publishing page, Academic Press, Inc., New York.
Brintzinger, Hans H., et al., "Stereospecific olefin polymerization with chiral metallocene catalysts," Angew. Chem. Int. Ed. Engl., 1995, pp. 1143-1170, VCH Verlagsgesellschaft mbH, Weinheim.
Britovsek, George J. P., et al., "Oligomerisation of ethylene by bis(imino)pyridyliron and -cobalt complexes," Chem. Eur. J., 2000, pp. 2221-2231, vol. 6, No. 12, Wiley-VCH Verlag GmbH, Weinheim.
Foreign communication from a related counterpart application—International Search Report and Written Opinion, PCT/US2004/004472, Jul. 16, 2004, 7 pages.
Foreign communication from a related counterpart application—International Search Report and Written Opinion, PCT/US2005/005437, Jul. 4, 2005, 13 pages.
Foreign communication from a related counterpart application—International Search Report and Written Opinion, PCT/US2005/042175, Aug. 17, 2006, 9 pages.
Foreign communication from a counterpart application—Written Opinion, SG 200605612-1, Aug. 28, 2007, 5 pages.
Foreign communication from a counterpart application No. CA 2,556,879 filed Feb. 18, 2005—Filing of Prior Art under Section 34.1 of the Patent Act Protest under Section 10 of the Patent Rules, Jan. 11, 2008, 11 pages.
Kumar, R. N., et al., "Mononuclear and binuclear complexes of Fe(II) and Cu(II) with 2,6-diacetyl pyridine monoxime and phenylene diamine," Jul.-Sep. 1999, pp. 964-969 plus 1 cover page, vol. 11, No. 3, Asian Journal of Chemistry.
Li, Yuesheng, et al., "Preparation of iron- or cobalt-based polynuclear pyridine-containing diimine catalysts for olefin polymerization," XP-002284349, Jun. 14, 2004, 1 page, CAPLUS.
Nelson, S. Martin, et al., "Metal-ion controlled reactions of 2,6-diacetylpyridine with 1,2-diaminoethane and 2,6-diformylpyridine with o-phenylenediamine and the crystal and molecular structure of a pentagonal pyramidal cadmium (II) complex containing unidentate o-phenylenediamine," 1982, pp. 407-415, J.C.S. Dalton.
Office Action dated Apr. 19, 2007 (8 pages), U.S. Appl. No. 10/783,429, filed Feb. 20, 2004.
Office Action dated Aug. 8, 2007 (13 pages), U.S. Appl. No. 10/782,554, filed Feb. 19, 2004.
Office Action dated Sep. 28, 2007 (8 pages), U.S. Appl. No. 10/783,429, filed Feb. 20, 2004.
Office Action dated Feb. 7, 2008 (6 pages), U.S. Appl. No. 10/782,554, filed Feb. 19, 2004.
Office Action dated Jun. 26, 2008 (16 pages), U.S. Appl. No. 11/207,232, filed Aug. 19, 2005.

Office Action dated Dec. 8, 2008 (41 pages), U.S. Appl. No. 10/782,554, filed Feb. 19, 2004.
Office Action (Final) dated Feb. 3, 2009 (15 pages), U.S. Appl. No. 11/207,232, filed Aug. 19, 2005.
Ranwell, A., et al., "Potential application of ionic liquids for olefin oligomerization," Sasol Technology R&D, Sasolburg, South Africa, 2002, pp. 147-160, American Chemical Society.
Rao, Guo-Ying, et al., "Coordination mode of the Cr(2-ethylhexanoate)3/triethylaluminum/dimethylpyrrole/tetrachloroethane," 2003, pp. 80-82, vol. 30, No. 1, Journal of Beijing University of Chemical Technology, Beijing, China.
Reagen, W. K., "Chromium(II) and (III) pyrrolyl ethylene oligomerization catalysts. Synthesis and crystal structure of square planar Cr(NC4H4)4-2, and pentanuclear (Cr5(NC4H4)10(OC4H8)4)," Symposium on Novel Preparation and Conversion of Light Olefins presented before the division of Petroleum Chemistry, Inc., Sep. 10-15, 1989, pp. 583-588, American Chemical Society.
Schofer, Susan J., et al., "Studies of a chromium-based ethylene oligomerization system," 1 page, INOR 817.
Small, Brooke L., et al., "Highly active iron and cobalt catalysts for the polymerization of ethylene," Journal of the American Chemical Society, 1998, pp. 4049-4050 plus 1 cover page, vol. 120, No. 16, American Chemical Society.
Small, Brooke L., et al., "Iron-based catalysts with exceptionally high activities and selectivities for oligomerization of ethylene to linear a-olefins," Journal of the American Chemical Society, 1998, pp. 7143-7144 plus 1 cover page, American Chemical Society.
Small, Brooke L., et al., "Polymerization of propylene by a new generation of iron catalysts: mechanisms of chain initiation, propagation, and termination," Macromolecules, 1999, pp. 2120-2130, vol. 32, No. 7, American Chemical Society.
Sui, Junlong, et al., "Synthesis of 1—hexene by trimerization of ethylene," 2001, pp. 23-26, 43, vol. 18, No. 2, China Synthetic Resin and Plastics.
Tamura, Takao, "Recent trends in a-olefin manufacturing technology," Idemitsu Giho, 1995, pp. 266-269, vol. 38, No. 3.
Tobisch, Sven, et al., "Catalytic linear oligomerization of ethylene to higher a-olefins: insight into the origin of the selective generation of 1-hexene promoted by a cationic cyclopentadienyl-arene titanium active catalyst," Organometallics, 2003, pp. 5392-5405, vol. 22, No. 26, American Chemical Society.
Tobisch, Sven, et al., "Catalytic oligomerization of ethylene to higher linear a-olefins promoted by cationic group 4 cyclopentadienyl-arene active catalysts: a DFT investigation exploring the influence of electronic factors on the catalytic properties by modification of the hemilabile arene functionality," Organometallics, 2004, pp. 4077-4088, vol. 23, No. 17, American Chemical Society.
Tobisch, Sven, et al., "Catalytic oligomerization of ethylene to higher linear a-olefins promoted by cationic group 4 [(n5-Cp-(CMe2-bridge)-Ph)M11(ethylene)2]+ (M=Ti, Zr, Hf) active catalysts: a density functional investigation of the influence of the metal on the catalytic activity and selectivity," J. Am. Chem. Soc., 2004, pp. 9059-9071, vol. 126, No. 29, American Chemical Society.
Tobisch, Sven, et al.,"Catalytic oligomerization of ethylene to higher linear a-olefins promoted by cationic group 4 cyclopentadienyl-arene active catalysts: toward the computational design of zirconium- and hafnium-based ethylene trimerization catalysts," Organometallics, 2005, pp. 256-265, vol. 24, No. 2, American Chemical Society.
Van Rensburg, Werner Janse, et al., "A DFT study toward the mechanism of chromium-catalyzed ethylene trimerization," Organometallics, 2004, pp. 1207-1222, vol. 23, No. 6, American Chemical Society.
Agapie, Theodor, et al., "Mechanistic studies of the ethylene trimerization reaction with chromium-diphosphine catalysts: experimental evidence for a mechanism involving metallacyclic intermediates," J. Am. Chem. Soc. 2004, pp. 1304-1305, vol. 126, No. 5, American Chemical Society.
Agapie, Theodor, et al., "Structural and mechanistic studies of a chromium-diphosphine system for catalytic trimerization of ethyl-

(56) References Cited

OTHER PUBLICATIONS ene," INOR 494, Mar. 28-Apr. 1, 2004, 1 page, The 227th ACS National Meeting, Anaheim, California.
"Aldrich," Catalog Handbook of Fine Chemicals, Aldrich Chemical Company, 1990-1991, Cover page, Information Sheet, and pp. 1274-1275.
Alobaidi, Fahad, et al., "Direct synthesis of linear low-density polyethylene of ethylene/1-hexene from ethylene with a tandem catalytic system in a single reactor," Journal of Polymer Science: Part A: Polymer Chemistry, 2004, pp. 4327-4336, vol. 42, Wiley Periodicals, Inc.
Andes, Cecily, et al., "Formation of an ethene trimerization catalyst from (CH3)2TACL3," 1 page, INOR 261.
Andes, Cecily, et al., "New tantalum catalyst for the selective trimerization of ethene," 1 page, INOR 273.
Andes, Cecily, et al., "New tantalum-based catalyst system for the selective trimerization of ethene to 1-hexene," J. Am. Chem. Soc., 2001, pp. 7423-7424, vol. 123, No. 30, American Chemical Society.
Blok, Arno N. J., et al., "Mechanism of ethene trimerization at an ansa-(arene) (cyclopentadienyl) titanium fragment," Organometallics, 2003, pp. 2564-2570, vol. 22, No. 13, American Chemical Society.
Bollmann, Annette, et al., "Ethylene tetramerization: a new route to produce 1-octene in exceptionally high selectivities," J. Am. Chem. Soc., 2004, pp. 14712-14713, vol. 126, No. 45, American Chemical Society.
Briggs, John R., "The selective trimerization of ethylene to hex-1-ene," 1989, pp. 674-675, J. Chem. Soc., Chem. Commun.
Carter, Anthea, et al., "High activity ethylene trimerisation catalysts based on diphosphine ligands," Chem. Commun., 2002, pp. 858-859, The Royal Society of Chemistry.
Chen, Jwu-Ting, et al., "Dimerization and oligomerization of ethylene catalyzed by a palladium(II) complex with imine-phosphine ligand," 2000, pp. 279-281, vol. 47, No. 1, Journal of the Chinese Chemical Society.
Dai, Changhua, "Commercialization of 1-hexene by ethylene trimerization in China," Nov. 2002, pp. 25-29, vol. 10, No. 11, Petroleum & Petrochemical Today.
De Bruin, Theodorus J. M., et al., "Hemilabile ligand induced selectivity: a DFT study on ethylene trimerization catalyzed by titanium complexes," Organometallics, 2003, pp. 3404-3413, vol. 22, No. 17, American Chemical Society.
De Wet-Roos, Deon, et al., "Homogeneous tandem catalysis of bis(2-decylthioethyl)amine-chromium trimerization catalyst in combination with metallocene catalysts," Macromolecules, 2004, pp. 9314-9320, vol. 37, No. 25, American Chemical Society.
Deckers, Patrick J. W., et al., "Catalytic trimerization of ethene with highly active cyclopentadienyl-arene titanium catalysts," Organometallics, 2002, pp. 5122-5135, vol. 21, No. 23, American Chemical Society.
Deckers, Patrick J. W., et al., "Switching a catalyst system from ethene polymerization to ethene trimerization with a hemilabile ancillary ligand," Angew. Chem. Int. Ed., 2001, pp. 2516-2519, vol. 40, No. 13, Wiley-VCH Verlag GmbH, D-69451 Weinheim.
Dixon, John T., et al., "Advances in selective ethylene trimerisation—a critical overview," Journal of Organometallic Chemistry, 2004, pp. 3641-3668, vol. 689, Elsevier B.V.
Emrich, Rainer, "The role of metallacycles in the chromium-catalyzed trimerization of ethylene," Organometallics, Apr. 15, 1997, pp. 1511-1513, vol. 16, No. 8, American Chemical Society.
Fang, Yiqun, et al., "A new chromium-based catalyst coated with paraffin for ethylene oligomerization and the effect of chromium state on oligomerization selectivity," Applied Catalysis A: General, 2002, pp. 33-38, vol. 235, Elsevier Science B.V.
Foreign communication from a related counterpart application—International Search Report and Written Opinion, PCT/US2005/005416, Jun. 1, 2005, 10 pages.
Foreign communication from a related counterpart application—International Search Report and Written Opinion, PCT/US2006/031303, Dec. 19, 2006, 13 pages.
Foreign communication from a related counterpart application—EP Examination Report, 05723396.7, Oct. 10, 2007, 4 pages.
Foreign communication from a counterpart application—International Search Report and Written Opinon, PCT/US2008/083026, Mar. 19, 2009, 9 pages.
Freemen, J. W., et al., "Selective production of 1-hexene from ethylene," Florida Catalysis Conference, Apr. 19-23, 1999, 30 pages.
Hessen, Bart, "Monocyclopentadienyl titanium catalysts: ethene polymerisation versus ethene trimerisation," Journal of Molecular Catalysis A: Chemical, 2004, pp. 129-135, vol. 213, Elsevier B.V.
Huang, Jiling, et al., "Ethylene trimerization with a half-sandwich titanium complex bearing a pendant thienyl group," Chem Commun, 2003, pp. 2816-2817, The Royal Society of Chemistry.
Jiang, Tao, et al., "Research advances of 1-hexene process by ethylene trimerization," Oct. 2000, pp. 284-287, vol. 18, No. 5, Petrochemical Technology & Application.
Köhn, R. D., et al., "Olefin trimerization with 1,3,5-triazacyclohexane complexes of chromium," INOR 278, 2 pages.
Köhn, Randolf D., et al., "1,3,5-Triazacyclohexane complexes of chromium as homogeneous model systems for the phillips catalyst," 2003, pp. 88-100, American Chemical Society.
Köhn, Randolf D., et al., "1,3,5-Triazacyclohexane complexes of chromium as homogeneous model systems for the phillips catalyst," pp. 147-155.
Köhn, Randolf D., et al., "Selective trimerization of a-olefins with triazacyclohexane complexes of chromium as catalysts," Angew. Chem. Int. Ed., 2000, pp. 4337-4339, vol. 39, No. 23, Wiley-VCH Verlag GmbH, D-69451 Weinheim.
Luo, He-Kuan, et al., "The effect of halide and the coordination geometry of chromium center in homogeneous catalyst system for ethylene trimerization," Journal of Molecular Catalysis A: Chemical, 2004, pp. 9-17, vol. 221, Elsevier B.V.
Mahomed, Hamdani, et al., "Ethylene trimerisation catalyst based on substituted cyclopentadienes," Applied Catalysis A: General, 2003, pp. 355-359, vol. 255, Elsevier B.V.
Manyik, R. M., et al., "A soluble chromium-based catalyst for ethylene trimerization and polymerization," Journal of Catalysis, 1977, pp. 197-209, vol. 47, Academic Press, Inc.
Mark, Herman, F., Editor, "Encyclopedia of polymer science and engineering," vol. 6, 1986, pp. 383-522 plus 1 cover page, 2 publishing pages, and 1 contents page, John Wiley & Sons, Inc., USA.
McGuinnes, David S., et al., "First Cr(III)—SNS complexes and their use as highly efficient catalysts for the trimerization of ethylene to 1-hexene," J. Am. Chem. Soc., 2003, pp. 5272-5273, vol. 125, No. 18, American Chemical Society.
McGuinnes, David S., et al., "Novel Cr-PNP complexes as catalysts for the trimerisation of ethylene," Chem. Commun., 2003, pp. 334-335, The Royal Society of Chemistry.
Meijboom, Nicolaas, et al., "Organometallic chemistry of chromium(VI): synthesis of chromium(VI) alkyls and their precursors. X-ray crystal structure of the metallacycle Cr(NtBu)2{o-(CHSiMe3)2C6H4}," Organometallics, 1990, pp. 774-782, vol. 9, No. 3, American Chemical Society.
Mihan, Shahram, et al., "Triazacyclohexane complexes of chromium for selective trimerization," 1 page, INOR 114.
Monoi, Takashi, et al., "Silica-supported Cr[N(SiMe3)2]3/isobutylalumoxane catalyst for selective ethylene trimerization," Journal of Molecular Catalysis A: Chemical, 2002, pp. 135-141, vol. 187, Elsevier Science B.V.
Morgan, David H., et al., "The effect of aromatic ethers on the trimerisation of ethylene using a chromium catalyst and aryloxy ligands," Adv. Synth. Catal., 2003, pp. 939-942, vol. 345, Wiley-VCH Verlag GmbH & Co. KGaA, Weinheim.
Ninanalov, I. I., et al., "Equilibrium of the trimerization of ethylene into hexenes," Ref. Zh., Khim, Abstract No. 24B897, 1983, 2 pages, Copyright 2003, ACS.
Office Action (Restriction Requirement) dated May 24, 2005 (6 pages), U.S. Appl. No. 10/783,429, filed Feb. 20, 2004.
Office Action dated Aug. 31, 2005 (13 pages), U.S. Appl. No. 10/783,429, filed Feb. 20, 2004.

(56) References Cited

OTHER PUBLICATIONS

Office Action dated Jan. 18, 2006 (15 pages), U.S. Appl. No. 10/783,429, filed Feb. 20, 2004.
Office Action (Final) dated May 24, 2006 (8 pages), U.S. Appl. No. 10/783,429, filed Feb. 20, 2004.
Office Action dated Sep. 7, 2006 (4 pages), U.S. Appl. No. 10/783,429, filed Feb. 20, 2004.
Office Action dated Jan. 9, 2007 (13 pages), U.S. Appl. No. 10/783,429, filed Feb. 20, 2004.
Esteruelas, Miguel A., et al., "Preparation, Structure and Ethylene Polymerization Behavior of Bis (imino) pyridyl Chromium(III) Complexes," Organometallics—American Chemical Society, Jan. 1, 2003, pp. 395-406, vol. 22.
Small, Brooke L, et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.
Foreign communication from a related counterpart application—International Preliminary Report on Patentability, PCT/US2005/005416, Aug. 22, 2006, 6 pages.
Foreign communication from a related counterpart application—International Preliminary Report on Patentability, PCT/US2006/031303, Feb. 20, 2008, 7 pages.
Wu, Tianzhi, et al., "Catalytic trimerization of ethylene by half-sandwich titanium complexes bearing a pendant ethereal group," Journal of Molecular Catalysis A: Chemical, 2004, pp. 227-229, vol. 214, Elsevier B.V.
Yang, Y., et al., "Roles of chloro compound in homogeneous [Cr(2-ethylhexanoate)3/2,5-dimethylpyrrole/triethylaluminum/chlorocompound] catalyst system for ethylene trimerization," Applied Catalysis A: General, 2000, pp. 29-38, vol. 193, Elsevier Science B.V.
Ye, Zhibin, et al., "A tandem catalytic system for the synthesis of ethylene-hex-1-ene copolymers from ethylene stock," Macromol. Rapid Commun., 2004, pp. 647-652, vol. 25, Wiley-VCH Verlag GmbH & Co. KGaA, Weinheim.
Yu, Zhi-Xiang, "Theoretical studies of the mechanisms of ethene trimerization by Ta- and Cr-based catalysts," 1 page, INOR 857.
Yu, Zhi-Xiang, et al., "Why trimerization? Computational elucidation of the origin of selective trimerization of ethene catalyzed by [TaCl3(CH3)2] and an agostic-assisted hydride transfer mechanism," Angew. Chem. Int. Ed., 2003, pp. 808-811, vol. 42, No. 7, Wiley-VCH Verlag GmbH & Co. KGaA, Weinheim.

* cited by examiner

OLEFIN OLIGOMERIZATION METHODS

CROSS-REFERENCE TO RELATED APPLICATIONS

Not applicable.

FIELD OF THE INVENTION

The present disclosure relates to processes for producing an olefin oligomer. More particularly, the present disclosure relates to improved processes for oligomerizing olefins.

BACKGROUND OF THE INVENTION

Olefins are important items of commerce. Their many applications include employment as intermediates in the manufacture of detergents, as precursors to more environmentally friendly refined oils, as monomers, and as precursors for many other types of products. An important subset of olefins are olefin oligomers, and one method of making olefin oligomers is via oligomerization of other olefins (e.g., ethylene) in a catalytic reaction involving various types of catalysts and/or catalyst systems. Examples of catalyst systems used commercially in the oligomerization of olefins include alkylaluminum compounds, certain nickel-phosphine complexes, a titanium halide with a Lewis acid (e.g., diethyl aluminum chloride), and a selective 1-hexene catalyst system containing a chromium containing compound (e.g., a chromium carboxylate), a nitrogen containing ligand (e.g., a pyrrole), and a metal alkyl (e.g., alkyl aluminum compounds).

Several non-commercial olefin oligomerization catalyst systems are based upon metal complexes of pyridine bisimines, metal complexes of α-diimine compounds having a metal complexing group, and selective trimerization and/or tetramerization catalyst system using a metal complex of a compound having a diphosphinylaminyl group. These catalyst systems typically use an alkylaluminum compound (e.g., aluminoxane) to activate the metal complexes for olefin oligomerization.

Applications and demand for olefin oligomers (e.g., alpha olefins) continue to multiply, and competition to supply them correspondingly intensifies. Thus, additional novel and improved methods for olefin oligomerization are desirable.

SUMMARY OF THE INVENTION

In an aspect, the present application relates to an olefin oligomerization process comprising a) contacting an olefin and a catalyst system comprising i) a transition metal complex and ii) a metal alkyl compound to form an olefin oligomer product in a continuous reactor and b) controlling an olefin oligomer product distribution K value by adjusting an olefin oligomerization parameter selected from i) a transition metal of the transition metal complex concentration in the continuous reactor, ii) a metal of the metal alkyl compound concentration in the continuous reactor, iii) a metal of the metal alkyl to transition metal of the transition metal complex molar ratio in the continuous reactor, or iv) any combination thereof. In another aspect, the present application relates to an olefin oligomerization process comprising a) contacting an olefin and a catalyst system comprising i) a transition metal complex and ii) a metal alkyl compound to form an olefin oligomer product in a continuous reactor, b) selecting an olefin oligomer product distribution K value from a correlation of the olefin oligomer product distribution K value with an olefin oligomerization parameter selected from i) a transition metal of the transition metal complex concentration in the continuous reactor, ii) a metal of the metal alkyl compound concentration in the continuous reactor, iii) a metal of the metal alkyl to transition metal of the transition metal complex molar ratio in the continuous reactor, or iv) any combination thereof; and c) adjusting the selected olefin oligomerization parameter to obtain the selected olefin oligomer product distribution K value. In yet another aspect, the present application relates to an olefin oligomerization process comprising a) correlating an olefin oligomer product distribution K value for oligomerizing an olefin in a continuous reactor in the presence of a catalyst system comprising i) a transition metal complex and ii) a metal alkyl compound to an olefin oligomerization parameter selected from i) a transition metal of the transition metal complex concentration in the continuous reactor, ii) a metal of the metal alkyl compound concentration in the continuous reactor, iii) a metal of the metal alkyl to transition metal of the transition metal complex molar ratio in the continuous reactor, or iv) any combination thereof; b) selecting an olefin oligomerization reactor K value; and c) oligomerizing the olefin in the continuous reactor to form an olefin oligomer product at the selected olefin oligomer product distribution K value by setting the selected olefin oligomerization parameters necessary to achieve the selected olefin oligomer distribution K value. In yet a further aspect, the present application relates to an oligomerization process comprising a) contacting an olefin and a catalyst system comprising i) a transition metal complex and ii) a metal alkyl compound, and b) forming an olefin oligomer product in a continuous reactor at olefin oligomerization temperature ranging from 100° C. to 150° C.

In an embodiment, the transition metal complex comprises a transition metal compound complexed to a ligand comprising a pyridine bisimine group. In some embodiments, the transition metal compound comprises a Group 8-10 halide, nitrate, sulfate, phosphate, halate, hydrocarboxide, carboxylate, or β-dionate. In some embodiments, the metal alkyl compound comprises an alumoxane. In some embodiments, the olefin oligomer product distribution K value can be controlled in a range from 0.5 to 0.8. In an embodiment, the olefin oligomer product distribution K value can be controlled by adjusting an olefin oligomerization parameter selected from i) the transition metal of the transition metal complex concentration in the continuous reactor ranges from $1.0 \times 10^{-6}$ to $5.0 \times 10^{-1}$ mole of transition metal per kilogram olefin oligomerization solution, ii) the metal of the metal alkyl compound concentration in the continuous reactor ranges from $5.0 \times 10^{-3}$ to $1.0 \times 10^{3}$ mole of metal per kilogram olefin oligomerization solution, iii) the metal of the metal alkyl to transition metal of the transition metal complex molar ratio in the continuous reactor ranges from 5:1 to 100,000:1, or iv) any combination thereof. In some embodiments, olefin oligomer product is produced at a temperature ranging from 20° C. to 150° C. In other embodiments, 1) the olefin consists essentially of ethylene, 2) the transition metal complex comprises an iron(II) halide or a cobalt(II) halide complexed to a ligand comprising a pyridine bisimine group, 3) the metal alkyl compound comprises an alumoxane, 4) the olefin oligomer product is produced at a temperature ranging from 50° C. to 130° C. and an ethylene partial pressure ranging from 150 psig to 2,000 psig, and 5) the olefin oligomer product distribution K value for the transition metal complex is controlled in a range from 0.55 to 0.7 by adjusting an olefin oligomerization parameter selected from i) the transition metal of the transition metal complex concentration in the continuous reactor ranges from $1.0 \times 10^{-5}$ to $1.0 \times 10^{-2}$ mole of transition metal per kilogram olefin oligomerization solution ii) the metal of the metal alkyl compound concentration in the continuous reactor ranges from $5.0 \times 10^{-2}$ to $1.0 \times 10^{1}$ mole of metal per kilogram olefin oligomerization solution, iii) the of the metal alkyl to transition metal of the transition metal complex molar ratio in the continuous reactor ranges from 5:1 to 100,000:1, or iv) any combination thereof.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
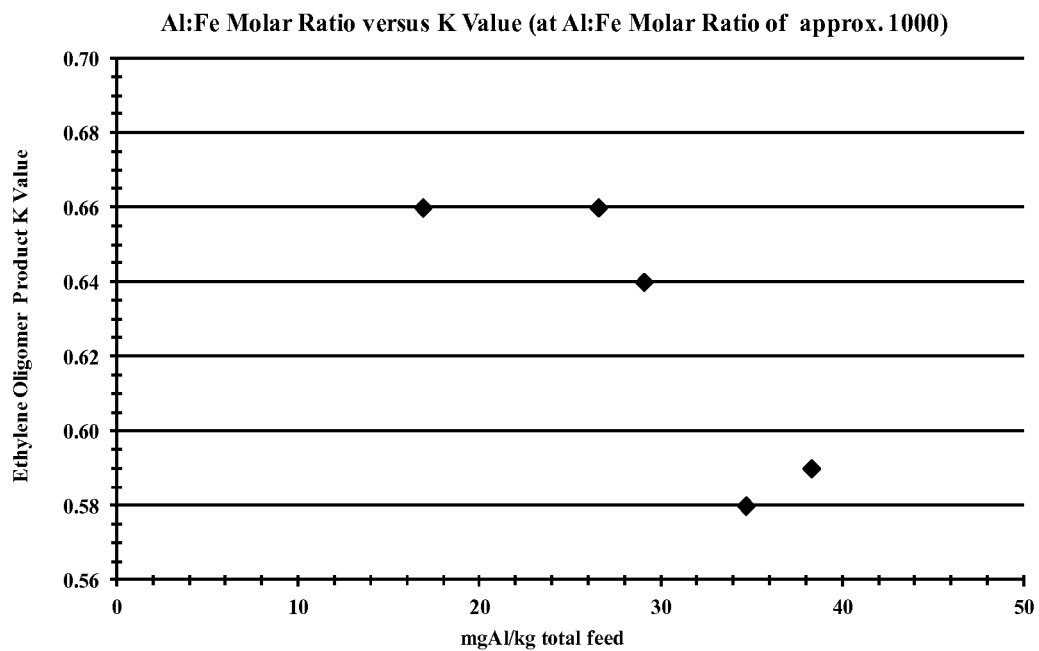
FIG. 1 provides a graph showing the relationship between the aluminum of the aluminoxane concentration and the ethylene oligomer product distribution K value.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in Chemical and Engineering News, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting of specific or alternatively, consist of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

In this disclosure, the terms first, second, and third, among others, can be utilized to differentiate multiple occurrences of a similar element. For example a method can utilize two or more solvents in different steps of a method, or alternatively, two different solvents in a mixture. The differentiating term can be applied to any element described herein when necessary to provide a differentiation. It should be understood that the numerical or alphabetical precedence of the differentiating terms do not imply a particular order or preference of the element in a method or compound described herein unless specifically specified otherwise.

In this disclosure, a process can have multiple steps or can include features having a number of different elements (e.g., components in a catalyst system or components in an olefin oligomerization process, among other features). These steps and/or elements can be designated utilizing the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), an N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," among others, as members.

For the purposes of this application, the term or variations of the term "organyl group consisting of inert functional groups" refers to an organyl group (having a free valence on a carbon atom) wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group having a free valence on a heteroatom which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an hydrocarboxy group can complex with a metal compound, a hydrocarboxy group located at a para position of a substituted pyridine ring or substituted imine phenyl group can be an inert functional group because a single metal compound molecule cannot complex with the three nitrogen atoms of a bis(imine)pyridine ligand and the para hydrocarboxy group within the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include a halide (fluoride, chloride, bromide, and iodide), nitro, hydrocarboxy groups (e.g., alkoxy, and/or aroxy, among others), and/or hydrocarbosulfidyl groups (e.g., RS—), among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, tertiary, and quaternary alkyl groups are derived by removal of a hydrogen atom from methane, a primary, a secondary, and a tertiary carbon atom, respectively, of an alkane. The n-alkyl group can be derived by removal of a hydrogen atom from a terminal carbon atom of a linear alkane. The groups $CH_3$, $RCH_2$ ($R \neq H$), $R_2CH$ ($R \neq H$), and $R_3C$ ($R \neq H$) are primary, secondary, tertiary, and quaternary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

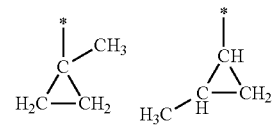

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or an aromatic ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s). The term "hydrocarbon olefin" refers to olefin compounds containing only hydrogen and carbon.

The term "alkene" whenever used in this specification and claims refers a linear or branched aliphatic hydrocarbon olefin that has one or more carbon-carbon double bonds. Alkenes having only one, only two, only three, etc. . . . such multiple bond can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" (e.g., pyrrolidin-1-yl or morpholin-1-yl, among others), aromatic "arylheteryl groups" (e.g., pyrrol-1-yl or indol-1-yl, among others), and acyclic groups (e.g., organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

A "heterocyclic compound" is a cyclic compound having at least two different elements as ring member atoms. For example, heterocyclic compounds can comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

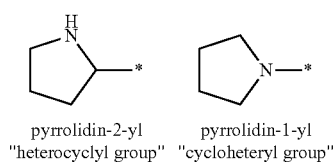 [SMILES: *C1CCCN1 ; *N1CCCC1]

pyrrolidin-2-yl "heterocyclyl group"    pyrrolidin-1-yl "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. Generally, a heterocyclic compound can be aliphatic or aromatic unless otherwise specified.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g., benzene, toluene, or xylene, among others. An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

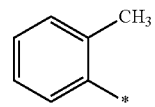 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g., the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g., the 2 carbon atom in the phenyl group of 6-phenylbenzofuran and a heteroarene group if the removed hydrogen carbon came from a heteroaromatic ring or ring system carbon atom (e.g., the 2 or 7 carbon atom of the benzofuran group or 6-phenylbenzo-furan). It should be noted that according the definitions provided herein, general arene groups (including an aryl group and an areylene group) include those having zero, one, or more than one hydrocarbyl substituent groups located on an aromatic hydrocarbon ring or ring system carbon atom (e.g a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized is an aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "primary carbon group," a "secondary carbon group," a "tertiary carbon group," and a "quaternary carbon group" describe the type of carbon atom which would be created when the group is attached to a base structure. A "primary carbon group" is a group wherein the carbon atom having the free valence has no other carbon atom containing group attached to it (e.g., a methyl group, a chloromethyl group, among others. A "secondary carbon group" is a group wherein the carbon atom having the free valence has one and only one other carbon atom containing group attached to it (e.g., an ethyl group, a 1-chloroeth-1-yl group, or a methoxymethyl group, among others). A "tertiary carbon group" is a group wherein the carbon atom having the free valence has two and only two other carbon atom containing groups attached to it (e.g., an isopropyl group, a 2-chloroprop-1-yl group, or a 1-methoxyethyl-1-yl group, among others). A "quaternary carbon group" is a group wherein the carbon atom having the free valence has three and only three other carbon atom containing groups attached to it (e.g., a tert-butyl group or a 2-methoxyprop-2-yl group, among others).

A "halide" has its usual meaning; therefore, examples of halides include fluoride, chloride, bromide, and iodide.

An "organoaluminum compound," is used to describe any compound that contains an aluminum-carbon bond. A "hydrocarbyl aluminum compound," is used to describe any compound that has at least one hydrocarbyl group attached to an aluminum atom. Other groups such as hydrocarboxide group(s) (or alkoxide group(s)) and halogens can also be bound to aluminum atoms in the compound unless otherwise specified; for example, a trihydrocarbyl aluminum compound, a dihydrocarbyl aluminum halide, a hydrocarbyl aluminum dihydrocarboxide compound, and a hydrocarbyl aluminoxane (among others) are all hydrocarbyl aluminum compounds. An "alkyl aluminum compound" is used to describe any compound having an alkyl group attached to an aluminum atom. Other groups such as hydrocarboxide group(s) (or alkoxide group(s)) and halogens can also be bound to aluminum atoms in the compound unless otherwise specified; for example, a trialkyl aluminum compound, a dialkyl aluminum halide, an alkyl aluminum dialkoxide compound, and an alkyl aluminoxane (among others) are all alkyl aluminum compounds. The terms "organoaluminum compounds," hydrocarbyl aluminum compounds," and "alkyl aluminum compounds" also include their respective aluminate compounds which contain an aluminum-carbon bond unless otherwise specified; e.g., tetrakis(p-tolyl)aluminate salts, among others.

Within this disclosure a "neutral Lewis base" is meant a compound, which is not an ion, which can act as a Lewis base. Examples of such compounds include ethers, amines, thioethers, and nitriles. By "cationic Lewis acid" is meant a cation which can act as a Lewis acid. Examples of such cations are sodium and silver cations. By relatively non-coordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405-1421 (1988), and S. H. Strauss, Chem. Rev., vol. 93, p. 927-942 (1993), both of which are hereby incorporated by reference. Among such anions are those formed from alkylaluminum compounds, defined above, and $X^-$, including $R^9{}_3AlX^-$, $R^9{}_2AlClX^-$, $R^9AlCl_2X^-$, and $R^9AlOX^-$. Other useful non-coordinating anions include $BAF^-$ {BAF is tetrakis[3,5-bis(trifluoromethyl)phenyl]borate}, $SbF_6{}^-$, $PF_6{}^-$, and $BF_4{}^-$, trifluoromethanesulfonate, p-toluenesulfonate, $(R_fSO_2)_2N^-$ (wherein $R_f$ is perfluoroalkyl), and $(C_6F_5)_4B^-$. By an empty coordination site is meant a potential coordination site that does not have a ligand bound to it.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be reference using comprising or some other alternative language. For example, a reference to a phenyl group comprising a substituent at the 4-position refers to a group having a non-hydrogen atom at the 4-position and hydrogen or any other non-hydrogen group at the 2-, 3-, 5-, and 6-positions.

The term "reactor effluent," and it derivatives (e.g., oligomerization reactor effluent) generally refers to all the material which exits the reactor. The term "reactor effluent," and its derivatives, can also be prefaced with other descriptors that limit the portion of the reactor effluent being referenced. For example, the term "reactor effluent" would refer to all material exiting the reactor (e.g., product and solvent or diluent, among others), while the term "olefin reactor effluent" refers to the effluent of the reactor which contains an olefin (i.e. carbon-carbon) double bond and the term "olefin oligomer product reactor effluent" refers to the effluent of the reactor which is an olefin oligomer product.

The term "oligomerization," and its derivatives, refers to processes which produce a mixture of products containing at least 70 wt. % products containing from 2 to 30 monomer units. Similarly, an "oligomer" is a product that contains from 2 to 30 monomer units while an "oligomer product" or an "oligomerization product" includes all products made by the "oligomerization" process including the "oligomers" and products which are not "oligomers" (e.g., product which contain more than 30 monomer units). It should be noted that the monomer units in the "oligomer" or "oligomerization product" do not have to be the same. For example, an "oligomer," "oligomer product," or "oligomerization product" of an "oligomerization" process using ethylene and propylene as monomers can contain both ethylene and/or propylene units.

The term or variation of the terms an "oligomer product having X carbon atoms" and "$C_x$ oligomer product," wherein X can be any positive non-zero integer, refers to materials produced by the oligomerization which have X carbon atoms. Thus, the term "oligomer product having X carbon atoms" excludes materials having X carbon atoms which were not produced by the olefin oligomerization (e.g., solvent). These terms can also include other descriptive words (e.g., olefin, liquid, and mixture, among others) without detracting from the essence of the term referring to materials having X carbon atoms, produced by the oligomerization, and fitting the additional descriptive terms. The term "olefin oligomerization solution" refers to a solution containing all the components necessary to oligomerize the olefin and includes the olefin oligomer product produced by the olefin oligomerization.

Catalyst system activity is defined as grams of a product produced per gram of metal of the metal compound (or metal complex) utilized in the catalyst system over the first 30 minutes of an oligomerization or polymerization reaction beginning from the time when the complete catalyst system is contacted with the olefin. Catalyst system activity can be stated in terms of various products of an olefin oligomerization or polymerization. For example, in an ethylene oligomerization process utilizing a catalyst system comprising an iron complex as the metal complex, the catalyst system activities which can be utilized include (g ethylene oligomer)/(g Fe), and (total oligomer product)/(g Fe), among other activities.

Unless otherwise specified, the terms contacted, combined, and "in the presence of" refer to any addition sequence, order, or concentration for contacting or combining the recited two or more components. The combining or contacting of the components, according to the various methods described herein can occur in one or more contact zones under suitable contact conditions such as temperature, pressure, contact time, flow rates, etc. . . . . The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact, unless otherwise specified. The processes can be carried out in a batch or continuous process as is suitable for a given embodiment, unless otherwise specified.

The terms "simultaneously," "simultaneously contact," "contact simultaneously," and their derivatives when referring to a contact method refers to a contact method wherein the two or more recited compounds, mixtures, streams, and/or compositions are contacted by flowing into a common junction, pot, vessel, or reactor, among others, at the same time. The terms "substantially simultaneously," "substantially simultaneously contact," "contact substantially simultaneously," and their derivatives when referring to a contact method refers to a contact method wherein, during the contact of two or more recited compounds, mixtures, streams, and/or compositions, the two or more recited compounds, mixtures, streams, and/or compositions are contacted such that for some period during the during the contact process the two or more recited compounds, mixtures, streams, and/or compositions flow into a common junction, pot, vessel, or reactor at the same time. It should be noted that the terms "substantially simultaneously," "substantially simultaneously contact," "contact substantially simultaneously," and their derivatives do not mean that the two or more recited compounds, mixtures, streams, and/or compositions are contacted simultaneously over the entire addition of each of the two or more recited compounds, mixtures, streams, and/or compositions. The terms "substantially simultaneously," "substantially simultaneously contact," "contact substantially simultaneously," and it derivatives include scenarios where the flow of one of the (or less than all of the) recited compounds, mixtures, streams, and/or compositions can be initiated into the common junction, pot, vessel, or reactor before the others and/or the flow of one of the (or less than all of the) recited compounds, mixtures, streams, and/or compositions into the common junction, pot, vessel, or reactor can be completed, stopped, or discontinued before the other recited compounds, mixtures, streams, and/or compositions. In any embodiment or aspect described herein, the terms "simultaneously," "simultaneously contact," "contact simultaneously," and their derivatives, these terms can be modified by the inclusion of a term providing a quantity of the each of the recited compounds, mixtures, streams, and/or compositions which can be contacted simultaneously indicate scenarios of various degrees of "substantially simultaneously," "substantially simultaneously contact," "contact substantially simultaneously," and their derivatives. For example, at least 20%, 30%, 40%, 50%, 60%, 70%, 75%, 80%, 85%, 90%, 95% of each of the recited compounds, mixtures, streams, and/or compositions can be "simultaneously contacted" or "contacted simultaneously." Generally, the percentages of the recited compounds, mixtures, streams, and/or compositions that can be "simultaneously contacted" or "contacted simultaneously" can be by weight (wt. %), by volume (volume %), or by mole (mole %). Unless otherwise specified, recited compounds, mixtures, streams, and/or compositions that are "substantially simultaneously," "substantially simultaneously contact," "contact substantially simultaneously," and their derivatives shall mean that at least 50% of each of the recited compounds, mixtures, streams, and/or compositions can be "simultaneously contacted" or "contacted simultaneously."

It should be further noted, that in reference to contact method or process, "simultaneously," "simultaneously contact," "contact simultaneously," "substantially simultaneously contact," "contact substantially simultaneously," and their derivatives is different than a process or method wherein one or more a first materials (e.g., compound, mixture, stream, and/or composition) already resides in a pot, vessel, or reactor and one or more other compounds, mixtures, streams, and/or compositions are added to the pot, vessel, or reactor. In this instance the first material in the pot, vessel, or reactor does not flow into the pot, vessel, or reactor concurrently with the other compounds, mixtures, streams, and/or compositions and the material in the pot. Thus, the first material and the other compounds, mixtures, streams, and/or compositions cannot be said to be "simultaneously contacted," "contacted simultaneously," "substantially simultaneously contacted," or "contacted substantially simultaneously." with the other component(s).

The term "controlling" in any phrase directed to controlling an olefin oligomerization dependent parameter (e.g., "controlling an olefin oligomer product distribution K value"), whenever used in this specification and claims, refers to changing the internal state of the olefin oligomerization to a different state (changing the dependent process parameter) by making a change to (or adjusting) an independent olefin oligomerization process parameter. Further, the phrase "correlating an olefin oligomer product distribution K value" in reference to one or more of the identified independent olefin oligomerization process parameters refers to establishing that the one or more identified parameters influences the value of the olefin oligomer product distribution K value. The relationship/correlation between the identified parameter and K is such that a change in the identified parameter results in a change in the olefin oligomer product distribution K value. The relationship between the olefin oligomer product distribution K value and the identified parameter can be directly or indirectly causative and is not limited by the phrase "correlating an olefin oligomer product distribution K value." Generally, controlling the dependent olefin oligomerization parameter (e.g., "controlling an olefin oligomer product distribution K value") can be achieved by making a change to (or adjusting) one or more of the independent olefin oligomerization process parameters that correlate with the independent olefin oligomerization parameter.

Disclosed herein are olefin oligomerization processes. In an embodiment, the olefin oligomerization processes can be a continuous process implemented in one or more reactors. Herein a continuous process refers to a process meeting one or more of the following criteria: (a) materials are fed into the reactor at the same time as product is removed from the reactor; (b) the condition of a material introduced to the reactor is a function of its position with the process as it flows from the point at which it is introduced to the reactor to the point at which it is removed from the reactor; (c) the quantity of product produced is a function of (i) the duration for which the process is operated and (ii) the throughput rate of the process. In an embodiment, the olefin oligomerization process can comprise contacting an olefin and a catalyst system to form an olefin oligomer product. In another embodiment, the olefin oligomerization process can comprise contacting an olefin, a transition metal complex, and a metal alkyl compound to from an olefin oligomer product. In an embodiment, the olefin oligomer product can comprise more than one type of olefin oligomer and the number and type of olefin oligomers present in the olefin oligomer product can be altered using methodologies disclosed herein. Generally, the olefin and the catalyst system (or the transition metal complex and a metal alkyl compound) are independent elements of the olefin oligomerization process. The olefin oligomerization process can be described utilizing any combination of any aspect or embodiment of the olefin described herein and any aspect or embodiment of the catalyst system (or any aspect or embodiment of the transition metal complex and any aspect or embodiment of the metal alkyl compound) described herein.

Generally, the olefin which can be oligomerized in the olefin oligomerization process can comprise, or consist essentially of, a $C_2$ to $C_{30}$ olefin; alternatively, a $C_2$ to $C_{16}$ olefin; or alternatively, a $C_2$ to $C_{10}$ olefin. In an embodiment, the olefin can be, comprise, or consist essentially of, an alpha olefin; alternatively, a linear alpha olefin; or alternatively, a normal alpha olefin. In an embodiment, the olefin can comprise, or consist essentially of, ethylene, propylene, or a combination thereof; alternatively, ethylene; or alternatively, propylene. When the olefin utilized in the olefin oligomerization process consists essentially of ethylene, the olefin oligomerization process can be referred to as an ethylene oligomerization process.

Generally, the catalyst system which can be utilized in the olefin oligomerization process can comprise a transition metal complex and a Lewis acid capable of abstracting an anionic specie, a hydride, or an alkyl group; alternatively, a transition metal complex and a metal alkyl compound. In an embodiment, the transition metal complex and the Lewis acid are independent elements of a catalyst system. The transition metal complex and the Lewis acid are independently described herein and the catalyst system can be described utilizing any aspect or embodiment of the transition metal complex described herein and any aspect or embodiment of the Lewis acid described herein. Generally, the transition metal complex and the metal alkyl compound are independent elements of a catalyst system. The transition metal complex and the metal alkyl are independently described herein and the catalyst system can be described utilizing any aspect or embodiment of the transition metal complex described herein and any aspect or embodiment of the metal alkyl described herein.

In an aspect, the transition metal complex can comprise a transition metal compound complexed to a ligand. Generally, the transition metal compound and the ligand are independent elements of the transition metal complex. The transition metal compound and the ligand are independently described herein. The transition metal complex can be described using any aspect or embodiment of the transition metal compound described herein and any aspect or embodiment of the ligand described herein. In some embodiments, the ligand can comprise a pyridine bisimine group (one or more) and the transition metal complex can be referred to as a transition metal compound complexed to a ligand comprising a pyridine bisimine group. In other embodiments, the ligand can be a pyridine bisimine ligand (or compound) and the transition metal complex can be referred to as a transition metal pyridine bisimine complex.

In an aspect, the ligand can comprise a pyridine bisimine group (also referred to as a pyridine bisimine ligand). In some embodiments, the pyridine bisimine ligand can comprise only one pyridine bisimine group; or alternatively, the pyridine bisimine ligand can comprise only two pyridine bisimine groups. In an embodiment, the pyridine bisimine ligand can have Structure PBI I, Structure PBI II, Structure PBI III, Structure BPBI I, Structure BPBI III, or any combination thereof. In some embodiments, the pyridine bisimine ligand can have Structure PBI I, Structure PBI II, Structure PBI III, or any combination thereof; or alternatively, Structure BPBI I, Structure MPBI III, or any combination thereof. In other embodiments, the pyridine bisimine ligand can have Structure PBI I; alternatively, Structure PBI II; alternatively, Structure PBI III; alternatively, Structure BPBI I; or alternatively, Structure MPBI III. Substituents $R^1$, $R^2$, $R^3$, $R^4$, and $R^5$ of Structure PBI I, Structure PBI II, Structure PBI III, Structure BPBI I, and Structure PBI III, $R^6$ and $R^7$ of Structure PBI I (or $R^6$ of Structure BPBI I), $R^{12}$, $R^{13}$, $R^{14}$, $R^{15}$, $R^{16}$, $R^{22}$, $R^{23}$, $R^{24}$, $R^{25}$, and $R^{26}$ of Structure PBI II (or $R^{12}$, $R^{13}$, $R^{14}$, $R^{15}$, and $R^{16}$ of Structure PBI III and Structure BPBI III), and L of Structure BPBI I and BPBI III are each independent elements of their respective structures. The pyridine bisimine ligands having Structure PBI I, Structure PBI II, Structure PBI III, Structure BPBI I, and/or Structure BPBI III can be described utilizing any combination of any aspect or embodiment of substituents $R^1$, $R^2$, $R^3$, $R^4$, $R^5$, $R^6$, $R^7$, $R^{12}$, $R^{13}$, $R^{14}$, $R^{15}$, $R^{16}$, $R^{22}$, $R^{23}$, $R^{24}$, $R^{25}$, and $R^{26}$ described herein and any aspect or embodiment of L described herein.

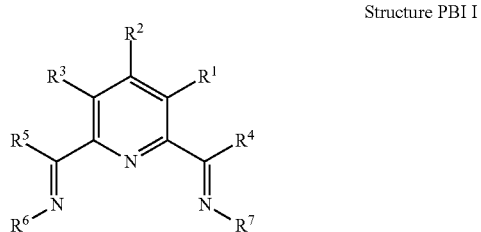

Structure PBI I

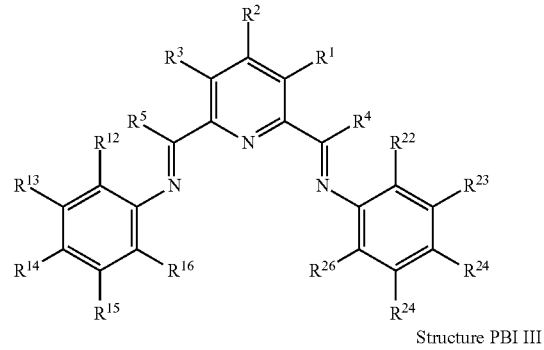

Structure PBI II

Structure PBI III

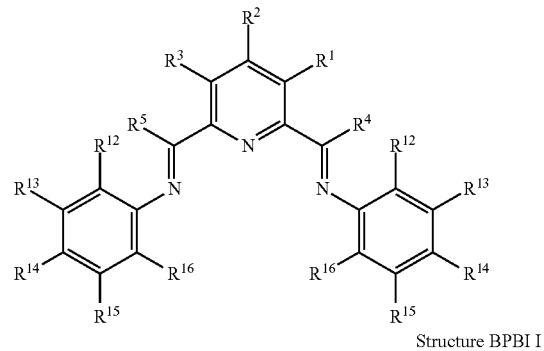

Structure BPBI I

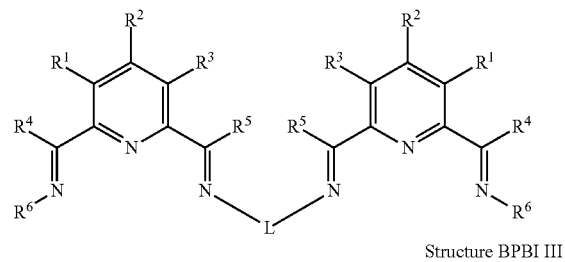

Structure BPBI III

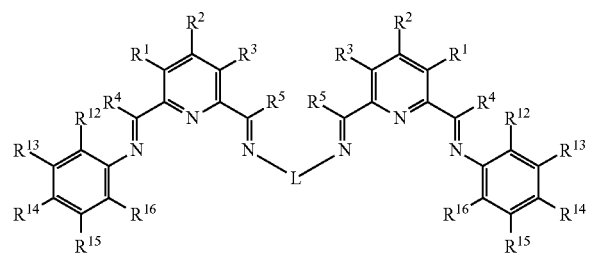

In an aspect, $R^1$, $R^2$, and $R^3$ independently can be hydrogen, an inert functional group, or an organyl group; alternatively, hydrogen or an organyl group; alternatively, an inert functional group or an organyl group; alternatively, hydrogen, an inert functional group, or an organyl group consisting of inert functional groups; alternatively, hydrogen or an organyl group consisting of inert functional groups; alternatively, an inert functional group or an organyl group consisting of inert functional groups; alternatively, hydrogen, an inert functional group, or a hydrocarbyl group; alternatively, hydrogen or a hydrocarbyl group; alternatively, an inert functional group or a hydrocarbyl group; alternatively, alternatively, hydrogen or an inert functional group; alternatively, hydrogen; alternatively, an organyl group; alternatively, organyl group consisting of inert functional groups; or alternatively, a hydrocarbyl group. In an aspect $R^4$ and $R^5$ independently can be hydrogen or an organyl group; alternatively, hydrogen and an organyl group consisting of inert functional groups; alternatively, hydrogen and a hydrocarbyl group; alternatively, hydrogen; alternatively, an organyl group; alternatively, an organyl group consisting of inert functional groups; or alternatively, a hydrocarbyl group. In an aspect $R^6$ and $R^7$ independently can be an organoheteryl group; alternatively, an organyl group; alternatively, an organyl group consisting of inert functional groups; or alternatively, a hydrocarbyl group. In an aspect, $R^{12}$, $R^{13}$, $R^{14}$, $R^{15}$, $R^{16}$, $R^{22}$, $R^{23}$, $R^{24}$, $R^{25}$, and $R^{26}$ independently can be hydrogen, an inert functional group, or an organyl group; alternatively, hydrogen or an organyl group; alternatively, an inert functional group or an organyl group; alternatively, hydrogen, an inert functional group, or an organyl group consisting of inert functional groups; alternatively, hydrogen or an organyl group consisting of inert functional groups; alternatively, an inert functional group or an organyl group consisting of inert functional groups; alternatively, hydrogen, an inert functional group, or a hydrocarbyl group; alternatively, hydrogen or a hydrocarbyl group; alternatively, an inert functional group or a hydrocarbyl group; alternatively, alternatively, hydrogen or an inert functional group; alternatively, hydrogen; alternatively, an organyl group; alternatively, an organyl group consisting of inert functional groups; or alternatively, a hydrocarbyl group. Inert functional groups, organoheteryl groups, organyl groups, organyl groups consisting of inert functional groups, and hydrocarbyl groups are independently described herein. Any aspect or embodiment of the inert functional groups, organoheteryl groups, organyl groups, organyl groups consisting of inert functional groups, and hydrocarbyl groups described herein can be utilized to further describe any aspect or embodiment of a pyridine bisimine ligand having Structure PBI I, Structure PBI II, Structure PBI III, Structure BPBI I, and/or Structure MPBI III.

In embodiment, any organyl group which can be utilized as a non-hydrogen $R^1$-$R^3$, $R^4$-$R^5$, $R^6$-$R^7$, $R^{12}$-$R^{16}$, or $R^{22}$-$R^{26}$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, any organyl group consisting of inert functional groups which can be utilized as a non-hydrogen $R^1$-$R^3$, $R^4$-$R^5$, $R^6$-$R^7$, $R^{12}$-$R^{16}$, or $R^{22}$-$R^{26}$ can be a $C_1$ to $C_{30}$ organyl group consisting of inert functional group; alternatively, a $C_1$ to $C_{20}$ organyl group consisting of inert functional group; alternatively, a $C_1$ to $C_{15}$ organyl group consisting of inert functional group; alternatively, a $C_1$ to $C_{10}$ organyl group consisting of inert functional group; or alternatively, a $C_1$ to $C_5$ organyl group consisting of inert functional group. In embodiment, any hydrocarbyl group which can be utilized as a non-hydrogen $R^1$-$R^3$, $R^4$-$R^5$, $R^6$-$R^7$, $R^{12}$-$R^{16}$, or $R^{22}$-$R^{26}$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In an embodiment, any organoheteryl group which can be utilized as $R^6$ and/or $R^7$ can be a $C_1$ to $C_{30}$ organoheteryl group; alternatively, a $C_1$ to $C_{20}$ organoheteryl group; alternatively, a $C_1$ to $C_{15}$ organoheteryl group; alternatively, a $C_1$ to $C_{10}$ organoheteryl group; or alternatively, a $C_1$ to organoheteryl group.

In an aspect, each non-hydrogen $R^1$-$R^3$, $R^4$-$R^5$, $R^6$-$R^7$, $R^{12}$-$R^{16}$, or $R^{22}$-$R^{26}$ (organyl group, organyl group consisting of inert functional groups, or hydrocarbyl group, depending on its constituents) independently can be an alkyl group, a substituted alkyl group, a cycloalkyl group, a substituted cycloalkyl group, an aryl group, a substituted aryl group, an aralkyl group, or a substituted aralkyl group; alternatively, alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. Generally, these groups can have the same number of carbon atoms as the organyl group, organyl group consisting of inert functional groups, or hydrocarbyl group of which they are a member. These groups are independently described herein. Any aspect or any embodiment of these groups described herein can be utilized as non-hydrogen $R^1$-$R^3$, $R^4$-$R^5$, $R^6$-$R^7$, $R^{12}$-$R^{16}$ and/or $R^{22}$-$R^{26}$ to further describe any aspect or embodiment of a pyridine bisimine ligand having Structure PBI I, Structure PBI II, Structure PBI III, Structure BPBI I, and/or Structure MPBI III. One can readily determine from the descriptions herein whether a particular substituted alkyl group, substituted cycloalkyl group, substituted aryl group, and/or substituted aralkyl group is an organyl group, an organyl group consisting of inert functional groups, and/or a hydrocarbyl group from the description provided herein.

In an embodiment, any alkyl group (substituted or unsubstituted) utilized as a non-hydrogen $R^1$-$R^3$, $R^4$-$R^5$, $R^6$-$R^7$, $R^{12}$-$R^{16}$, and/or $R^{22}$-$R^{26}$ independently can be a $C_1$ to $C_{30}$ alkyl group; alternatively, a $C_1$ to $C_{20}$ alkyl group; alternatively, a $C_1$ to $C_{15}$ alkyl group; alternatively, $C_1$ to $C_{10}$ alkyl group; or alternatively, a $C_1$ to $C_5$ alkyl group. In some embodiments, any non-hydrogen $R^1$-$R^3$, $R^4$-$R^5$, $R^6$-$R^7$, $R^{12}$-$R^{16}$, and/or $R^{22}$-$R^{26}$ independently can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In other embodiments, any non-hydrogen $R^1$-$R^3$, $R^4$-$R^5$, $R^6$-$R^7$, $R^{12}$-$R^{16}$, and/or $R^{22}$-$R^{26}$ independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, any non-hydrogen $R^1$-$R^3$, $R^4$-$R^5$, $R^6$-$R^7$, $R^{12}$-$R^{16}$, and/or $R^{22}$-$R^{26}$ independently can be a substituted alkyl group. Each substituent of a substituted alkyl group which can be utilized as a non-hydrogen $R^1$-$R^3$, $R^4$-$R^5$ $R^6$-$R^7$, $R^{12}$-$R^{16}$ and/or $R^{22}$-$R^{26}$ independently can be a halogen or a hydrocarboxy group; alternatively, a halogen; or alternatively, a hydrocarboxy group. Halogens and hydrocarboxy groups that can be utilized as substituents are independently disclosed herein and can be utilized without limitation to further describe the substituted alkyl group which can be utilized as a non hydrogen $R^1$-$R^3$, $R^4$-$R^5$, $R^6$-$R^7$, $R^{12}$-$R^{16}$, and/or $R^{22}$-$R^{26}$.

In an aspect, any cycloalkyl group (substituted or unsubstituted) utilized as a non-hydrogen $R^1$-$R^3$, $R^4$-$R^5$, $R^6$-$R^7$, $R^{12}$-$R^{16}$, and/or $R^{22}$-$R^{26}$ independently can be a $C_4$ to $C_{30}$ cycloalkyl group; alternatively, a $C_4$ to $C_{20}$ cycloalkyl group; alternatively, a $C_4$ to $C_{15}$ cycloalkyl group; or alternatively, $C_4$ to $C_{10}$ cycloalkyl group. In an embodiment, any non-hydrogen $R^1$-$R^3$, $R^4$-$R^5$, $R^6$-$R^7$, $R^{12}$-$R^{16}$, and/or $R^{22}$-$R^{26}$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, any non-hydrogen $R^1$-$R^3$, $R^4$-$R^5$, $R^6$-$R^7$, $R^{12}$-$R^{16}$, and/or $R^{22}$-$R^{26}$ independently can be a cyclopentyl group, a substituted cyclopentyl group, a cyclohexyl group, or a substituted cyclohexyl group. In other embodiments, any non-hydrogen $R^1$-$R^3$, $R^4$-$R^5$, $R^6$-$R^7$, $R^{12}$-$R^{16}$, and/or $R^{22}$-$R^{26}$ independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, any non-hydrogen $R^1$-$R^3$, $R^4$-$R^5$, $R^6$-$R^7$, $R^{12}$-$R^{16}$, and/or $R^{22}$-$R^{26}$ independently can be a cyclopentyl group; alternatively, a substituted cyclopentyl group; a cyclohexyl group; or alternatively, a substituted cyclohexyl group. Substituents for the substituted cycloalkyl group are independently disclosed herein and can be utilized without limitation to further describe a substituted cycloalkyl group which can be utilized as a non-hydrogen $R^1$-$R^3$, $R^4$-$R^5$, $R^6$-$R^7$, $R^{12}$-$R^{16}$, and/or $R^{22}$-$R^{26}$.

In an aspect, any aryl group (substituted or unsubstituted) utilized as a non-hydrogen $R^1$-$R^3$, $R^4$-$R^5$, $R^6$-$R^7$, $R^{12}$-$R^{16}$, and/or $R^{22}$-$R^{26}$ independently can be a $C_6$ to $C_{30}$ aryl group; alternatively, a $C_6$ to $C_{20}$ aryl group; alternatively, a $C_6$ to $C_{15}$ aryl group; or alternatively, $C_6$ to $C_{10}$ aryl group. In an embodiment, any non-hydrogen $R^1$-$R^3$, $R^4$-$R^5$, $R^6$-$R^7$, $R^{12}$-$R^{16}$ and/or $R^{22}$-$R^{26}$ independently can be a phenyl group, a substituted phenyl group, a naphthyl group, or a substituted naphthyl group. In some embodiments, any non-hydrogen $R^1$-$R^3$, $R^4$-$R^5$, and/or $R^6$-$R^7$ independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, any non-hydrogen $R^1$-$R^3$, $R^4$-$R^5$, $R^6$-$R^7$, $R^{12}$-$R^{16}$, and/or $R^{22}$-$R^{26}$, independently can be a phenyl group; alternatively, a substituted phenyl group; alternatively, a naphthyl group; or alternatively, a substituted naphthyl group. In some embodiments, the naphthyl group (substituted or unsubstituted) which can be utilized as any non-hydrogen $R^1$-$R^3$, $R^4$-$R^5$, $R^6$-$R^7$, $R^{12}$-$R^{16}$, and/or $R^{22}$-$R^{26}$ can be a naphth-1-yl group or a naphth-2-yl group; alternatively, a naphth-1-yl group; or alternatively, a naphth-2-yl group. Substituents for the substituted phenyl or substituted naphthyl group are independently disclosed herein. These substituents can be utilized without limitation to further describe a substituted phenyl group or a substituted naphthyl group which can be utilized as a non-hydrogen $R^1$-$R^3$, $R^4$-$R^5$, $R^6$-$R^7$, $R^{12}$-$R^{16}$, and/or $R^{22}$-$R^{26}$. In some non-limiting embodiments, $R^1$-$R^3$, $R^4$-$R^5$, $R^6$-$R^7$, $R^{12}$-$R^{16}$, and/or $R^{22}$-$R^{26}$ independently can be a phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, each tolyl group which can be utilized as a $R^1$-$R^3$, $R^4$-$R^5$, $R^6$-$R^7$, $R^{12}$-$R^{16}$, and/or $R^{22}$-$R^{26}$ substituent independently can be a 2-methylphenyl group, a 3-methylphenyl group, or a 4-methyl phenyl group; alternatively, a 2-methylphenyl group; alternatively, a 3-methylphenyl group; or alternatively, a 4-methyl phenyl group. In an embodiment, each xylyl group which can be utilized as a $R^1$-$R^3$, $R^4$-$R^5$, $R^6$-$R^7$, $R^{12}$-$R^{16}$, and/or $R^{22}$-$R^{26}$ substituent independently can be a 2,3-dimethyl phenyl group, a 2,4-dimethylphenyl group, a 2,5-dimethyl phenyl group, a 2,6-dimethyl phenyl group, a 3,4-dimethyl phenyl group, or a 3,5-dimethyl phenyl group; alternatively, a 2,4-dimethylphenyl group or a 2,6-dimethyl phenyl group; alternatively, a 2,3-dimethyl phenyl group; alternatively, a 2,4-dimethylphenyl group; alternatively, a 2,5-dimethyl phenyl group; alternatively, a 2,6-dimethyl phenyl group; alternatively, a 3,4-dimethyl phenyl group; or alternatively, a 3,5-dimethyl phenyl group.

In an aspect, any aralkyl group (substituted or unsubstituted) utilized as a non-hydrogen $R^1$-$R^3$, $R^4$-$R^5$, $R^6$-$R^7$, $R^{12}$-$R^{16}$, and/or $R^{22}$-$R^{26}$ independently can be a $C_7$ to $C_{30}$ aralkyl group; alternatively, a $C_7$ to $C_{20}$ aralkyl group; alternatively, a $C_7$ to $C_{15}$ aralkyl group; or alternatively, $C_7$ to $C_{10}$ aralkyl. In an embodiment, any non-hydrogen $R^1$-$R^3$, $R^4$-$R^5$, $R^6$-$R^7$, $R^{12}$-$R^{16}$, and/or $R^{22}$-$R^{26}$ independently can be benzyl group, a substituted benzyl group, an ethylphenyl group (2-phenyleth-1-yl or 1-phenyleth-1-yl), or a substituted ethylphenyl group (2-phenyleth-1-yl or 1-phenyleth-1-yl). In some embodiments, any non-hydrogen $R^1$-$R^3$, $R^4$-$R^5$, $R^6$-$R^7$, $R^{12}$-$R^{16}$, and/or $R^{22}$-$R^{26}$ independently can be a benzyl group or a substituted benzyl group; alternatively, an ethylphenyl group or a substituted ethylphenyl group; alternatively, a benzyl group or an ethylphenyl group. In other embodiments, any non-hydrogen $R^1$-$R^3$, $R^4$-$R^5$, $R^6$-$R^7$, $R^{12}$-$R^{16}$, and/or $R^{22}$-$R^{26}$ independently can be a benzyl group; alternatively, a substituted benzyl group; alternatively, an ethylphenyl group; or alternatively, a substituted ethylphenyl group. Substituents for the substituted benzyl group or substituted ethylphenyl group (2-phenyleth-1-yl or 1-phenyleth-1-yl) are independently disclosed herein. These substituents can be utilized without limitation to further describe a substituted benzyl group or a substituted ethylphenyl group which can be utilized as a non-hydrogen $R^1$-$R^3$, $R^4$-$R^5$, $R^6$-$R^7$, $R^{12}$-$R^{16}$, and/or $R^{22}$-$R^{26}$.

In an aspect, each inert functional group which can be utilized as a non-hydrogen $R^1$-$R^3$, $R^{12}$-$R^{16}$, and/or $R^{22}$-$R^{26}$ independently can be a halide, a halogenated hydrocarbyl group, or a hydrocarboxy group; alternatively, a halide or a halogenated hydrocarbyl group; alternatively, a halide or a hydrocarboxy group; alternatively, a halogenated hydrocarbyl group or a hydrocarboxy group; alternatively, a halide; alternatively, a halogenated hydrocarbyl group; or alternatively, a hydrocarboxy group. In an embodiment, each halogenated hydrocarbyl group which can be utilized as a non-hydrogen $R^1$-$R^3$, $R^{12}$-$R^{16}$, and/or $R^{22}$-$R^{26}$ independently can be a $C_1$ to $C_{30}$ halogenated hydrocarbyl group; alternatively, a $C_1$ to $C_{20}$ halogenated hydrocarbyl group; alternatively, a $C_1$ to $C_{15}$ halogenated hydrocarbyl group; alternatively, a $C_1$ to $C_{10}$ halogenated hydrocarbyl group; or alternatively, a $C_1$ to $C_5$ halogenated hydrocarbyl group. In an embodiment, each hydrocarboxy group which can be utilized as a non hydrogen $R^1$-$R^3$, $R^{12}$-$R^{16}$, and/or $R^{22}$-$R^{26}$ independently can be a $C_1$ to $C_{30}$ hydrocarboxy group; alternatively, a $C_1$ to $C_{20}$ hydrocarboxy group; alternatively, a $C_1$ to $C_{15}$ hydrocarboxy group; alternatively, a $C_1$ to $C_{10}$ hydrocarboxy group; or alternatively, a $C_1$ to $C_5$ hydrocarboxy group. In an embodiment, an inert functional group which can be utilized as a non hydrogen $R^1$-$R^3$, $R^{12}$-$R^{16}$, and/or $R^{22}$-$R^{26}$ independently can be a $C_1$ to $C_{30}$ trihydrocarbylsiloxy group; alternatively, a $C_1$ to $C_{20}$ trihydrocarbylsiloxy group; alternatively, a $C_1$ to $C_{15}$ trihydrocarbylsiloxy group; alternatively, a $C_1$ to $C_{10}$ trihydrocarbylsiloxy group; or alternatively, a $C_1$ to $C_5$ trihydrocarbylsiloxy group.

In an aspect, each inert functional group which can be utilized as a non-hydrogen $R^1$-$R^3$, $R^{12}$-$R^{16}$, and/or $R^{22}$-$R^{26}$ independently can be a halide, a halogenated alkyl group, or an alkoxy group; alternatively, a halide or a halogenated alkyl group; alternatively, a halide or an alkoxy group; alternatively, a halogenated alkyl group or an alkoxy group; alternatively, a halide; alternatively, a which can be utilized as a non-hydrogen $R^1$-$R^3$, $R^{12}$-$R^{16}$, and/or $R^{22}$-$R^{26}$ independently can be a $C_1$ to $C_{30}$ trialkylsiloxy group; alternatively, a $C_1$ to $C_{20}$ trialkylsiloxy group; alternatively, a $C_1$ to $C_{15}$ trialkylsiloxy group; alternatively, a $C_1$ to $C_{10}$ trialkylsiloxy group; or alternatively, a $C_1$ to $C_5$ trialkylsiloxy group. The halogenated alkyl group can have the same number of carbon atoms as the herein described halogenated hydrocarbyl group. The alkoxy group can have the same number of carbon atoms as the herein described hydrocarboxy group. The trialkylsiloxy group can have the same number of carbon atoms as the herein described trihydrocarbylsiloxy group.

In an embodiment, each halide which can be utilized as a non-hydrogen $R^1$-$R^3$, $R^{12}$-$R^{16}$, and/or $R^{22}$-$R^{26}$ (or as a halogen for any general or specific halogenated hydrocarbyl group described herein) independently can be fluoride, chloride, bromide, or iodide. In some embodiments, each halide which can be utilized as a non-hydrogen $R^1$-$R^3$, $R^{12}$-$R^{16}$, and/or $R^{22}$-$R^{26}$ (or as a halogen for a halogenated hydrocarbyl group) independently can be fluoride; alternatively, chloride; alternatively, bromide; or alternatively, iodide.

In an embodiment, a halogenated hydrocarbyl group (or alkyl group) utilized as a non-hydrogen $R^1$-$R^3$, $R^{12}$-$R^{16}$ and/or $R^{22}$-$R^{26}$ independently can be any hydrocarbyl group (or alkyl group), wherein one or more hydrogen atoms has been replaced with a equal number of halogen atoms. Hydrocarbyl groups (or alkyl groups) and halogens have been disclosed herein as potential non-hydrogen groups which can be utilized for at least $R^1$-$R^3$, $R^{12}$-$R^{16}$, and/or $R^{22}$-$R^{26}$. These hydrocarbyl group (or alkyl groups) and halogens can be utilized without limitation to further described a halogenated hydrocarbyl group (or a halogenated alkyl group) which can be utilized as $R^1$-$R^3$, $R^{12}$-$R^{16}$, and/or $R^{22}$-$R^{26}$. In some non-limiting embodiments, the halogenated alkyl group which can be utilized as $R^1$-$R^3$, $R^{12}R^{16}$, and/or $R^{22}$-$R^{26}$ can be a trifluoromethyl group or a pentafluoroethyl group; alternatively, a trifluoromethyl group; or alternatively, a pentafluoroethyl group.

In an aspect, each non-hydrogen $R^1$-$R^3$, $R^{12}$-$R^{16}$, $R^{22}$-$R^{26}$ independently can be an alkoxy group, an aryloxy group, or an aralkoxy group; alternatively, an alkoxy group or an aryloxy group; alternatively, an alkoxy group; alternatively, an aryloxy group; or alternatively, an aralkoxy group. Generally, these groups can have the same number of carbon atoms as the hydrocarboxy group which can be utilized as a non hydrogen $R^1$-$R^3$, $R^{12}$-$R^{16}$, and/or $R^{22}$-$R^{26}$ to further describe any aspect or embodiment of a pyridine bisimine ligand having Structure PBI I, Structure PBI II, Structure PBI III, Structure BPBI I, and/or Structure MPBI III.

In an embodiment, any alkoxy group utilized as a non-hydrogen $R^1$-$R^3$, $R^{12}$-$R^{16}$ and/or $R^{22}$-$R^{26}$ independently can be a $C_1$ to $C_{30}$ alkoxy group; alternatively, a $C_1$ to $C_{20}$ alkoxy group; alternatively, a $C_1$ to $C_{15}$ alkoxy group; alternatively, $C_1$ to $C_{10}$ alkoxy group; or alternatively, a $C_1$ to $C_5$ alkoxy group. In some embodiments, any non-hydrogen $R^1$-$R^3$, $R^{12}$-$R^{16}$ and/or $R^{22}$-$R^{26}$ independently can be a methoxy group, an ethoxy group, a propoxy group, a butoxy group, a pentoxy group, a hexoxy group, a heptoxy group, an octoxy group, a nonoxy group, a decoxy group, a undecoxy group, a dodecoxy group, a tridecoxy group, a tetradecoxy group, a pentadecoxy group, a hexadecoxy group, a heptadecoxy group, an octadecoxy group, or a nonadecoxy group; or alternatively, a methoxy group, an ethoxy group, a propoxy group, a butoxy group, a pentoxy group, a hexoxy group, a heptoxy group, an octoxy group, a nonoxy group, or a decoxy group. In other embodiments, any non-hydrogen $R^1$-$R^3$, $R^{12}$-$R^{16}$, and/or $R^{22}$-$R^{26}$ independently can be a methoxy group, an ethoxy group, an n-propoxy group, an iso-propoxy group, an n-butoxy group, an iso-butoxy group, a sec-butoxy group, a tert-butoxy group, an n-pentoxy group, an iso-pentoxy group, a sec-pentoxy group, or a neopentoxy group; alternatively, a methoxy group, an ethoxy group, an iso-propoxy group, a tert-butoxy group, or a neopentoxy group; alternatively, a methoxy group; alternatively, an ethoxy group; alternatively, an n-propoxy group; alternatively, an iso-propoxy group; alternatively, a tert-butoxy group; or alternatively, a neopentoxy group.

In an aspect, any cycloalkoxy group utilized as a non-hydrogen $R^1$-$R^3$, $R^{12}$-$R^{16}$, and/or $R^{22}$-$R^{26}$ independently can be a $C_4$ to $C_{30}$ cycloalkoxy group; alternatively, a $C_4$ to $C_{20}$ cycloalkoxy group; alternatively, a $C_4$ to $C_{15}$ cycloalkoxy group; or alternatively, $C_4$ to $C_{10}$ cycloalkoxy group. In an embodiment, any non-hydrogen $R^1$-$R^3$, $R^{12}$-$R^{16}$, and/or $R^{22}$-$R^{26}$ independently can be a cyclobutoxy group, a cyclopentoxy group, a cyclohexoxy group, a cycloheptoxy group, or a cyclooctoxy group; alternatively, cyclopentoxy group or a cyclohexoxy group; alternatively, cyclopentoxy group; or alternatively, a cyclohexoxy group.

In an aspect, any aroxy group utilized as a non-hydrogen $R^1$-$R^3$, $R^{12}$-$R^{16}$, and/or $R^{22}$-$R^{26}$ independently can be a $C_6$ to $C_{30}$ aroxy group; alternatively, a $C_6$ to $C_{20}$ aroxy group; alternatively, a $C_6$ to $C_{15}$ aroxy group; or alternatively, $C_6$ to $C_{10}$ aroxy group. In an embodiment, any non-hydrogen $R^1$-$R^3$, $R^{12}$-$R^{16}$, and/or $R^{22}$-$R^{26}$ independently can be a phenoxy group, a toloxy group, a xyloxy group, or a trimethylphenoxy; alternatively, a phenoxy group; alternatively, a toloxy group; alternatively, a xyloxy group; or alternatively, a trimethylphenoxy.

In an aspect, any aralkoxy group utilized as a non-hydrogen $R^1$-$R^3$, $R^{12}$-$R^{16}$, and/or $R^{22}$-$R^{26}$ independently can be a $C_7$ to $C_{30}$ aralkoxy group; alternatively, a $C_7$ to $C_{20}$ aralkoxy group; alternatively, a $C_7$ to $C_{15}$ aralkoxy group; or alternatively, $C_7$ to $C_{10}$ aralkyl. In an embodiment, any non-hydrogen $R^1$-$R^3$, $R^4$-$R^5$, $R^6$-$R^7$, $R^{12}$-$R^{16}$, and/or $R^{22}$-$R^{26}$ independently can be benzoxy group.

In an aspect, each trihydrocarbylsiloxy group which can be utilized as a non-hydrogen $R^1$-$R^3$, $R^{12}$-$R^{16}$, and/or $R^{22}$-$R^{26}$ can be a trimethylsiloxy group, a triethylsiloxy group, a tripropylsiloxy group, or a triphenylsiloxy group. In an embodiment, each trihydrocarbylsiloxy group which can be utilized as a non hydrogen $R^1$-$R^3$, $R^{12}$-$R^{16}$, and/or $R^{22}$-$R^{26}$ can be a trimethylsiloxy group, a triethylsiloxy group, or a tripropylsiloxy group; alternatively, a trimethylsiloxy group; alternatively, a triethylsiloxy group; alternatively, a tripropylsiloxy group; or alternatively, a triphenylsiloxy group.

In an embodiment, each $R^6$ and/or $R^7$ independently can be a phenyl group or a substituted phenyl group; alternatively, a phenyl group; or alternatively, a substituted phenyl group. In an embodiment, each substituted phenyl group which can be utilized as $R^6$ and/or $R^7$ independently can comprise a substituent at a 2-position, a substituent at the 3-position, a substituent at a 4-position, substituents at a 2- and a 3-position, substituents at a 2- and a 4-position, substituents at a 2- and a 5-position, substituents at a 2- and a 6-position, or substituents at a 2-, a 4-, and a 6-position; alternatively, a substituent at a 2-position, a substituent at a 4-position, substituents at a 2- and a 4-position, substituents at a 2- and a 6-position, or substituents at a 2-, a 4-, and a 6-position; alternatively, a substituent at a 2-position; alternatively, a substituent at a 3-position; alternatively, a substituent at a 4-position; alternatively, substituents at a 2- and a 3-position; alternatively, substituents at a 2- and a 4-position; alternatively, substituents at a 2- and a 5-position; alternatively, substituents at a 2- and a 6-position or substituents at a 2-, a 4-, and a 6-position; alternatively, substituents at a 2- and a 6-position; or alternatively, substituents at a 2-, a 4-, and a 6-position. In an embodiment, where $R^6$ and $R^7$ independently can be a substituent phenyl group comprising substituents at particular positions, the remaining positions of the substituted phenyl group and the specified substituent positions can further have any aspect or embodiment consistent with the particular substituted phenyl group comprising a substituent at a specified position. In an embodiment, each substituted phenyl group which can be utilized as $R^6$ and/or $R^7$ independently can be a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group; alternatively, a 4-substituted phenyl group; alternatively, a 2,3-disubstituted phenyl group; alternatively, a 2,4-disubstituted phenyl group; alternatively, a 2,5-disubstituted phenyl group; alternatively, a 2,6-disubstituted phenyl group or a 2,4,6-trisubstituted phenyl group; alternatively, a 2,6-disubstituted phenyl group; alternatively, a 2,4,6-trisubstituted phenyl group; or alternatively, a 3,5-disubstituted phenyl group. Generally, each substituent of a substituted phenyl group can be any group described herein which can be utilized as $R^{12}$, $R^{13}$, $R^{14}$, $R^{15}$, $R^{16}$, $R^{22}$, $R^{23}$, $R^{24}$, $R^{25}$, and/or $R^{26}$.

In some non-limiting embodiments, the substituted phenyl group which can be utilized as $R^6$ and/or $R^7$ independently can be a 2-fluorophenyl group, a 2-chlorophenyl group, 2,6-difluorophenyl group, a 2,6-dichlorophenyl group, a 3-fluoro-2-methylphenyl group, a 4-fluoro-2-methylphenyl group, a 2-fluoro-6-methylphenyl group, a 2-chloro-6-methylphenyl group, a 2-chloro-6-phenylphenyl group, a (3-chlorobiphenyl-2-yl group), 2-(4-tert-butylphenyl)-6-halophenyl group, a (4'-tertbutyl-3-halo-biphenyl-2-yl group), a 2-methylphenyl group, 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,3-diisopropylphenyl group, a 2,6-dimethylphenyl group, a 2,6-diethylphenyl group, a 2,6-diisopropylphenyl group, a 2,6-di-tert-butylphenyl group, a 2,6-diphenylphenyl, a 3,5-di-tert-butylphenyl group, a 2,6-(4-tert-butylphenyl)phenyl group, a 2,4,6-trimethylphenyl group, a 2-trifluoromethylphenyl group, a 2,6-bis(trifluoromethyl)phenyl group, a 2-(phenyl)phenyl group (biphenyl-2-yl group), a 2-(4-tert-butylphenyl)phenyl group, a (4'-tertbutylbiphenyl-2-yl group), a 1,2,3,4-tetrahydronaphthalen-5-yl group, a 2-methoxyphenyl group, a 4-methoxyphenyl group, a 2-trimethylsiloxyphenyl group, or a 4-trimethylsiloxyphenyl group. In other non-limiting embodiments, the substituted phenyl group which can be utilized as $R^6$ and/or $R^7$ independently can be a 2-fluorophenyl group, a 2-chlorophenyl group, a 2,6-difluorophenyl group, or a 2,6-dichlorophenyl group; alternatively, a 3-fluoro-2-methylphenyl group, a 4-fluoro-2-methylphenyl group, a 2-fluoro-6-methylphenyl group, or a 2-chloro-6-methylphenyl group; alternatively, a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, a 2,6-di-tert-butylphenyl group, or a 2,4,6-trimethylphenyl group; alternatively, a 2-trifluoromethylphenyl group or a 2,6-bis(trifluoromethyl)phenyl group; alternatively, a 2-methoxyphenyl group or a 4-methoxyphenyl group; or alternatively, a 2-trimethylsiloxyphenyl group, or a 4-trimethylsiloxyphenyl group. In other non-limiting embodiments, the substituted phenyl group which can be utilized as $R^6$ and/or $R^7$ independently can be a 2-fluorophenyl group; alternatively, a 2,6-difluorophenyl group; alternatively, a 4-fluoro-2-methylphenyl group; alternatively, a 2-fluoro-6-methylphenyl group; alternatively, a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; alternatively, a 4-tert-butylphenyl group; alternatively, 2,3-diisopropylphenyl group; alternatively, a 2,6-dimethylphenyl group; alternatively, a 2,6-diethylphenyl group; alternatively, a 2,6-diisopropylphenyl group; alternatively, a 2,6-di-tert-butylphenyl group; alternatively, a 2,6-diphenylphenyl; alternatively, a 3,5-di-tert-butylphenyl group; alternatively, a 2,6-(4-tert-butylphenyl)phenyl group; alternatively, a 2,4,6-trimethylphenyl group; alternatively, a 2-trifluoromethylphenyl group; alternatively, a 2,6-bis(trifluoromethyl)phenyl group; alternatively, a 2-(phenyl)phenyl group (biphenyl-2-yl group); alternatively, a 2-(4-tert-butylphenyl)phenyl group; alternatively, (4'-tertbutylbiphenyl-2-yl group); alternatively, a 1,2,3,4-tetrahydronaphthalen-5-yl group; alternatively, a 2-methoxyphenyl group; alternatively, a 4-methoxyphenyl group; alternatively, a 2-trimethylsiloxyphenyl group; or alternatively, a 4-trimethylsiloxyphenyl group. One can readily recognize whether a particular substituted phenyl group is a 2-substituted phenyl group, a 4-substituted phenyl group, a 2,4-disubstituted phenyl group, a 2,6-disubstituted phenyl group, or a 2,4,6-trisubstituted phenyl group, 2,3-dimethylphenyl group, a 2,4-dimethylphenyl group, a 2,5-dimethylphenyl group, In an aspect, each organoheteryl group which can be utilized as $R^6$ and $R^7$ independently can be an aminyl group; alternatively, an N-hydrocarbyl aminyl group or an N,N-dihydrocarbylaminyl group, or alternatively, an N-hydrocarbyl aminyl group; or alternatively, an N,N-dihydrocarbylaminyl group. Generally, the aminyl group, the N-hydrocarbyl aminyl group, or the N,N-dihydrocarbylaminyl group can have the same number of carbon atoms as the organoheteryl groups described herein (with the exception that the N,N-dihydrocarbylaminyl group carbon number ranges begin at $C_2$. Hydrocarbyl groups are independently described herein and these hydrocarbyl groups (general or specific) can be utilized without limitation to further describe an N-hydrocarbyl aminyl group or an N,N-dihydrocarbylaminyl group which can be utilized as $R^6$ and $R^7$.

In an aspect, $R^6$ and $R^7$ independently can be a $C_4$ to $C_{30}$ heterocyclyl group; alternatively, a $C_4$ to $C_{20}$ heterocyclyl group; alternatively, a $C_4$ to $C_{15}$ heterocyclyl group; or alternatively, a $C_4$ to $C_{10}$ heterocyclyl group. In some embodiments, $R^6$ and $R^7$ independently can be a $C_4$ to $C_{30}$ pyrrol-1-yl group; alternatively, a $C_4$ to $C_{20}$ pyrrol-1-yl group; alternatively, a $C_4$ to $C_{15}$ pyrrol-1-yl group; or alternatively, a $C_4$ to $C_{10}$ pyrrol-1-yl group. In an embodiment, $R^6$ and $R^7$ independently can be a pyrrol-1-yl group or a substituted pyrrol-1-yl group; alternatively, a pyrrol-1-yl group; or alternatively, a substituted pyrrol-1-yl group. In an embodiment, where $R^6$ and $R^7$ independently can be a substituted pyrroly-1-yl group comprising substituents at particular positions, the remaining positions of the substituted pyrroly-1-yl and the specified substituent positions can further have any aspect or embodiment consistent with the particular substituted pyrrol-1-yl group comprising a substituent at a specified position. In an embodiment, the substituted pyrrol-1-yl group can comprise a substituent at a 2-position, substituents at a 2- and 4-position, or substituents at a 2- and 5-position; alternatively, a substituent at a 2-position or substituents at a 2- and 5-position; alternatively, a substituent at a 2-position; alternatively, substituents at a 2- and 4-position; or alternatively, substituents at a 2- and 5-position. In an embodiment, the substituted pyrrol-1-yl group can be a 2-substituted pyrrol-1-yl group, a 2,3-disubstituted pyrrol-1-yl group, a 2,4-disubstituted pyrrol-1-yl group, or a 2,5-disubstituted pyrrol-1-yl group; alternatively, a 2-substituted pyrrol-1-yl group or a 2,5-disubstituted pyrrol-1-yl group; alternatively, a 2-substituted pyrrol-1-yl group; alternatively, a 2,3-disubstituted pyrrol-1-yl group; alternatively, a 2,4-disubstituted pyrrol-1-yl group; or alternatively, a 2,5-disubstituted pyrrol-1-yl group.

In an embodiment, $R^6$ and $R^7$ independently can have the Structure P1 and Structure P2, respectively.

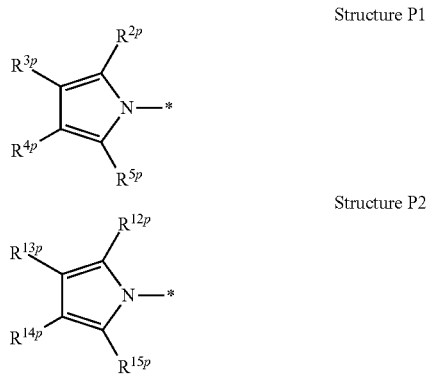

Structure P1

Structure P2

Generally, $R^{2p}$, $R^{3p}$, $R^{4p}$, and $R^5$ are independent elements of the Structure P1 and $R^{12p}$, $R^{13p}$, $R^{14p}$, and $R^{15p}$ are independent elements of the Structure P2. Structure P1 can be described utilizing any combination of $R^{2p}$, $R^{3p}$, $R^{4p}$, and $R^{5p}$ described herein and Structure P2 can be described utilizing any combination of $R^{12p}$, $R^{13p}$, $R^{14p}$, and $R^{15p}$.

In an aspect, each $R^{2p}$, $R^{3p}$, $R^{4p}$, and $R^{5p}$ in Structure P1 and each $R^{12p}$, $R^{13p}$, $R^{14p}$, and $R^{15p}$ in Structure P2 (or each substituent in a substituted pyrrol-1-yl group) and can be hydrogen, an inert functional group, or an organyl group; alternatively, hydrogen or an organyl group; alternatively, an inert functional group or an organyl group; alternatively, hydrogen, an inert functional group, or an organyl group consisting of inert functional groups; alternatively, hydrogen or an organyl group consisting of inert functional groups; alternatively, an inert functional group or an organyl group consisting of inert functional groups; alternatively, hydrogen, an inert functional group, or a hydrocarbyl group; alternatively, hydrogen or a hydrocarbyl group; alternatively, an inert functional group or a hydrocarbyl group; alternatively, alternatively, hydrogen or an inert functional group; alternatively, hydrogen; alternatively, an organyl group; alternatively, organyl group consisting of inert functional groups; or alternatively, a hydrocarbyl group. Inert functional groups, organyl groups, organyl groups consisting of inert functional groups, and hydrocarbyl groups are independently described herein as potential $R^1$, $R^2$, $R^3$, $R^{12}$, $R^{13}$, $R^{14}$, $R^{15}$, $R^{16}$, $R^{22}$, $R^{23}$, $R^{24}$, $R^{25}$, and $R^{26}$ groups within the pyridine bisimine ligands having Structure PBI I, Structure PBI II, Structure PBI III, Structure BPBI I, and Structure MPBI III. These aspects and embodiments of $R^1$, $R^2$, $R^3$, $R^{12}$, $R^{13}$, $R^{14}$, $R^{15}$, $R^{16}$, $R^{22}$, $R^{23}$, $R^{24}$, $R^{25}$, and $R^{26}$ groups can be utilized without limitation to further describe $R^{2p}$, $R^{3p}$, $R^{4p}$, and $R^{5p}$ within P1 and each $R^{12p}$, $R^{13p}$, $R^{14p}$, and $R^{15p}$ within P2 (or each substituent in a substituted pyrrol-1-yl group).

In an embodiment, the substituted pyrrol-1-yl group having Structure P1 and/or Structure P2 can be a 2-methylpyrrol-1-yl group, a 2-ethylpyrrol-1yl group, a 2-isopropylpyrrol-1yl group, a 2-(4-tert-butylphenyl)pyrrol-1-yl group, a 2-phenylpyrrol-1-yl group, a 2-(4-tert-butylphenyl)pyrrol-1-yl group, a 2,4-dimethylpyrrol-1-yl group, a 2,5-dimethylpyrrol-1-yl group, a 2,5-diethylpyrroly-1-yl group, a 2-ethyl-5-methylpyrrol-1-yl group, a 2,5-diisopropylpyrrol-1-yl group, a 2,5-di-tert-butylpyrrol-1-yl group, a 2,5-diphenylpyrrol-1-yl group, a 2,5-di(4-tert-butylphenyl)pyrrol-1-yl group, a 2-methyl-5-phenylpyrrol-1-yl group, a 2-tert-butyl-5-isopropylpyrrol-1-yl group, a 2-tert-butyl-5-phenylpyrrol-1-yl group, a 2-isopropyl-5-tolylylpyrrol-1-yl group, a 2-tert-butyl-4,5-dimethylpyrrol-1-yl group, a 2-halo-5-methylpyrrol-1-yl group, a 2-halo-5-phenylpyrrol-1-yl group, or a 2-halo-5-(4-ter-butyl-phenyl)pyrrol-1-yl group. In other embodiments, the substituted pyrrol-1-yl group having Structure P1 and/or Structure P2 can be a 2,5-dimethylpyrrol-1-yl group, a 2,5-diethylpyrroly-1-yl group, or a 2-ethyl-5-methyl-pyrrol-1-yl group; alternatively, a 2,5-dimethylpyrrol-1-yl group or a 2,5-diethyl-pyrroly-1-yl group; alternatively, a 2,5-diisopropylpyrrol-1-yl group, a 2,5-di-tert-butylpyrrol-1-yl group, a 2,5-diphenylpyrrol-1-yl group, or a 2,5-di(4-tert-butylphenyl)pyrrol-1-yl group; or alternatively, a 2,5-diisopropylpyrrol-1-yl group or a 2,5-di-tert-butylpyrrol-1-yl group. In yet other embodiments, the substituted pyrrol-1-yl group the substituted pyrrol-1-yl group having Structure P1 and/or Structure P2 can be a 2-methylpyrrol-1-yl-group; alternatively, 2,4-dimethylpyrrol-1-yl group; alternatively, a 2,5-dimethylpyrrol-1-yl group; alternatively, a 2,5-diethylpyrroly-1-yl group; alternatively, a 2-ethyl-5-methyl-pyrrol-1-yl group; alternatively, a 2,5-diisopropylpyrrol-1-yl group; alternatively, a 2,5-di-tert-butylpyrrol-1-yl group; alternatively, a 2,5-diphenylpyrrol-1-yl group; or alternatively, a 2,5-di(4-tert-butylphenyl) pyrrol-1-yl group.

In an aspect, L of the pyridine bisimine ligand having Structure BPBI I and/or Structure BPBI III can be an organylene group; alternatively, an organylene group consisting of inert functional group; or alternatively, a hydrocarbylene group. In an embodiment, L of the pyridine bisimine ligand having Structure BPBI I and/or Structure BPBI III can be a $C_1$ to $C_{30}$ organylene group; alternatively, a $C_1$ to $C_{20}$ organylene group; alternatively, a $C_1$ to $C_{15}$ organylene group; alternatively, a $C_1$ to $C_{10}$ organylene group; or alternatively, a $C_1$ to $C_5$ organylene group. In some embodiments, L of the pyridine bisimine ligand having Structure BPBI I and/or Structure BPBI III can be a $C_1$ to $C_{30}$ organylene group consisting of inert functional group; alternatively, a $C_1$ to $C_{20}$ organylene group consisting of inert functional group; alternatively, a $C_1$ to $C_{15}$ organylene group consisting of inert functional group; alternatively, a $C_1$ to $C_{10}$ organylene group consisting of inert functional group; or alternatively, a $C_1$ to $C_5$ organylene group consisting of inert functional group. In other embodiments, L of the pyridine bisimine ligand having Structure BPBI I and/or Structure BPBI III can be a $C_1$ to $C_{30}$ hydrocarbylene group; alternatively, a $C_1$ to $C_{20}$ hydrocarbylene group; alternatively, a $C_1$ to $C_{15}$ hydrocarbylene group; alternatively, a $C_1$ to $C_{10}$ hydrocarbylene group; or alternatively, a $C_1$ to $C_5$ hydrocarbylene group.

In an aspect, L of the pyridine bisimine ligand having Structure BPBI I and/or Structure BPBI III (organylene group, organylene group consisting of inert functional groups, or hydrocarbylene group, depending on its constituents) can be an alkylene group, a substituted alkylene group, a cycloalkylene group, a substituted cycloalkylene group, an arylene group, a substituted arylene group, an aralkylene group, or a substituted aralkylene group; alternatively, alkylene group, a cycloalkylene group, an arylene group, or an aralkylene group; alternatively, an alkylene group or a substituted alkylene group; alternatively, a cycloalkylene group or a substituted cycloalkylene group; alternatively, an arylene group or a substituted arylene group; alternatively, an aralkylene group, or a substituted aralkylene group; alternatively, an alkylene group; alternatively, a substituted alkylene group; alternatively, a cycloalkylene group; alternatively, a substituted cycloalkylene group; alternatively, an arylene group; alternatively, a substituted arylene group; alternatively, an aralkylene group; or alternatively, a substituted aralkylene group. Generally, the alkylene groups, substituted alkylene groups, cycloalkylene groups, substituted cycloalkylene groups, arylene groups, substituted arylene groups, aralkylene groups, and substituted aralkylene groups which can be utilized as L of the pyridine bisimine ligand having Structure BPBI I and/or Structure BPBI III can have the same number of carbon atoms as the organylene group, organylene group consisting of inert functional groups, or hydrocarbylene group of which they are a member.

In an aspect, the alkylene group (substituted or unsubstituted) which can be utilized as L of the pyridine bisimine ligand having Structure BPBI I and/or Structure BPBI III can be a $C_1$ to $C_{40}$ alkylene group (substituted or unsubstituted); alternatively, a $C_1$ to $C_{20}$ alkylene group (substituted or unsubstituted); alternatively, a $C_1$ to $C_{10}$ alkylene group (substituted or unsubstituted); or alternatively, a $C_1$ to $C_5$ alkylene group (substituted or unsubstituted). In an embodiment, L of the pyridine bisimine ligand having Structure BPBI I and/or Structure BPBI III can be a methylene group, an ethylene group, a propylene group, a butylene group, a pentylene group, a hexylene group, a heptylene group, a octylene group, a nonylene group, a decylene group, a undecylene group, a dodecylene group, a tridecylene group, a tetradecylene group, a pentadecylene group, a hexadecylene group, a heptadecylene group, or a octadecylene group; alternatively, a methylene group, an ethylene group, a propylene group, a butylene group, a pentylene group, a hexylene group, a heptylene group, a octylene group, a nonylene group, or a decylene group. In some embodiments, L of the pyridine bisimine ligand having Structure BPBI I and/or Structure BPBI III can be a methylene group, a eth-1,2-ylene group, a prop-1,2-ylene group, a prop-1,3-ylene group, a but-1,2-ylene group, a but-2,3-ylene group, a but-1,4-ylene group, a 2-methyl-prop-1,2-ylene group, a pent-1,5-ylene group, a pent-1,4-ylene group, a pent-1,3-ylene group, a pent-2,4-ylene group, a 2,2-dimethylprop-1,3-ylene group, a hex-1,6-ylene group, a 2-methypent-1,5-ylene group, a 2,3-dimethylbut-1,4-ylene group a 2,3-dimethylbut-2,3-ylene group, a 1,7-heptylene group, a 2,2'-dimethylpent-1,5-ylene group, a oct-1,8-ylene group, a non-1,9-ylene group, a 2,2,4-trimethylhex-1,6-ylene group, a 2,4,4-trimethylhex-1,6-ylene group, a 1,10-decylene group, a undec-1,1'-ylene group, a 2-butyl-2-ethylpent-1,5-ylene group, or a 1,12-dodecylene group; or alternatively, a eth-1,2-ylene group, a prop-1,3-ylene group, a but-1,2-ylene group, a but-1,4-ylene group, a hex-1,6-ylene group, a oct-1,8-ylene group, a 1,10-decylene group, or a 1,12-dodecylene group; alternatively, a methylene group; alternatively, a eth-1,2-ylene group; alternatively, a prop-1,2-ylene group; alternatively, a prop-1,3-ylene group; alternatively, a but-1,2-ylene group; alternatively, a but-2,3-ylene group; alternatively, a but-1,4-ylene group; alternatively, a 2-methylprop-1,2-ylene group; alternatively, a pent-1,5-ylene group; alternatively, a pent-1,4-ylene group; alternatively, a pent-1,3-ylene group; alternatively, a pent-2,4-ylene group; alternatively, a 2,2-dimethylprop-1,3-ylene group; alternatively, a hex-1,6-ylene group; alternatively, a oct-1,8-ylene group; alternatively, a 1,10-decylene group; or alternatively, a 1,12-dodecylene group.

In an aspect, the cycloalkylene group (substituted or unsubstituted) which can be utilized as L of the pyridine bisimine ligand having Structure BPBI I and/or Structure BPBI III can be a $C_3$-$C_{40}$ cycloalkyl group (substituted or unsubstituted); alternatively, a $C_3$-$C_{20}$ cycloalkyl group (substituted or unsubstituted); alternatively, a $C_3$-$C_{15}$ cycloalkyl group (substituted or unsubstituted); or alternatively, a $C_3$-$C_{10}$ cycloalkyl group (substituted or unsubstituted). In an aspect, L of the pyridine bisimine ligand having Structure BPBI I and/or Structure BPBI III can be a cyclopropylene group, a substituted cyclopropylene group, a cyclobutylene group, a substituted cyclobutylene group, a cyclopentylene group, a substituted cyclopentylene group, a cyclohexylene group, a substituted cyclohexylene group, a cycloheptyl group, a substituted cycloheptyl group, a cyclooctyl group, or a substituted cyclooctyl group; or alternatively, a cyclopentylene group, a substituted cyclopentylene group, a cyclohexylene group, or a substituted cyclohexylene group. In an embodiment, L of the pyridine bisimine ligand having Structure BPBI I and/or Structure BPBI III can be a cyclopropylene group or a substituted cyclopropylene group; alternatively, cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group; alternatively, a cyclopentyl group; alternatively, a substituted cyclopentyl group; a cyclohexyl group; or alternatively, a substituted cyclohexyl group.

In an aspect, L of the pyridine bisimine ligand having Structure BPBI I and/or Structure BPBI III can be a cyclopent-1,2-ylene group, a substituted cyclopent-1,2-ylene group, a cyclopent-1,3-ylene group, a substituted cyclopent-1,3-ylene group, a cyclohex-1,2-ylene group, a substituted cyclohex-1,2-ylene group, a cyclohex-1,3-ylene group, a substituted cyclohex-1,3-ylene group, a cyclohex-1,4-ylene group, or a substituted cyclohex-1,4-ylene group. In an embodiment, L of the pyridine bisimine ligand having Structure BPBI I and/or Structure BPBI III can be a cyclopent-1,2-ylene group, a substituted cyclopent-1,2-ylene group, a cyclopent-1,3-ylene group, or a substituted cyclopent-1,3-ylene group; alternatively, a cyclohex-1,2-ylene group, a substituted cyclohex-1,2-ylene group, a cyclohex-1,3-ylene group, a substituted cyclohex-1,3-ylene group, a cyclohex-1,4-ylene group, or a substituted cyclohex-1,4-ylene group; alternatively, a cyclopent-1,3-ylene group, or a substituted cyclopent-1,3-ylene group; alternatively, a cyclohex-1,3-ylene group, a substituted cyclohex-1,3-ylene group, a cyclohex-1,4-ylene group, or a substituted cyclohex-1,4-ylene group; alternatively, a cyclopent-1,3-ylene group, a cyclohex-1,3-ylene group, or a cyclohex-1,4-ylene group; alternatively, a cyclopent-1,3-ylene group; alternatively, a cyclohex-1,3-ylene group; or alternatively, a cyclohex-1,4-ylene group.

In an embodiment, the substituted cyclopent-1,2-ylene group which can be utilized as L of the pyridine bisimine ligand having Structure BPBI I and/or Structure BPBI III can comprise a substituent at the 3-position, the 4-position, or the 3- and 5-positions; alternatively, the 3-position or the 4-position; alternatively, the 3-position; alternatively, the 4-position; or alternatively, the 3- and 5-positions. In some embodiments, the substituted cyclopent-1,2-ylene group which can be utilized as L of the pyridine bisimine ligand having Structure BPBI I and/or Structure BPBI III can be a 3-substituted, a 4-substituted, or a 3,5-disubstituted cyclopent-1,2-ylene group; alternatively, a 3-substituted or a 4-substituted cyclopent-1,2-ylene group; alternatively, a 3-substituted cyclopent-1,2-ylene group; alternatively, a 4-substituted cyclopent-1,2-ylene group; or alternatively, a 3,5-disubstituted cyclopent-1,2-ylene group. In an embodiment, the substituted cyclopent-1,3-ylene group can comprise a substituent at the 2-position, the 4-position, the 2- and 4-position, or the 4- and 5-positions; alternatively, the 2-position or the 4-position; alternatively, the 2-position; alternatively, the 2- and 4-positions; or alternatively, the 4- and 5-positions. In some embodiments, the substituted cyclopent-1,3-ylene group which can be utilized as L of the pyridine bisimine ligand having Structure BPBI I and/or Structure BPBI III can be a 2-substituted, 4-substituted, 2,4-disubstituted, 4,5-disubstituted, 2,4,5-trisubstituted cyclopent-1,3-ylene group; alternatively, a 2-substituted or 4-substituted cyclopent-1,3-ylene group; alternatively, a 2-substituted cyclopent-1,3-ylene group; alternatively, a 4-substituted cyclopent-1,3-ylene group; alternatively, a 2,4-disubstituted cyclopent-1,3-ylene group; alternatively, a 4,5-disubstituted cyclopent-1,3-ylene group; or alternatively, a 2,4,5-trisubstituted cyclopent-1,3-ylene group.

In an embodiment, the substituted cyclohex-1,2-ylene group which can be utilized as $R^2$ and/or $R^4$ can comprise a substituent at the 3-position, the 4-position, the 3- and 4-position, the 3- and 5-positions, or the 3- and 6-positions; alternatively, the 3-position or the 4-position; alternatively, the 3- and 4-position, the 3- and 5-positions, or the 3- and 6-positions; alternatively, the 3-position; alternatively, the 4-position; alternatively, the 3- and 4-positions; alternatively, the 3- and 5-positions; or alternatively, the 3- and 6-positions. In some embodiments, the substituted cyclohex-1,2-ylene group which can be utilized as $R^2$ and/or $R^4$ can be a 3-substituted, 4-substituted, 3,4-disubstituted, 3,5-disubstituted, or 3,6-disubstituted cyclohex-1,2-ylene group; alternatively, a 3-substituted or 4-substituted cyclohex-1,2-ylene group; alternatively, a 3,4-disubstituted, 3,5-disubstituted, or 3,6-disubstituted cyclohex-1,2-ylene group; alternatively, a 3-substituted cyclohex-1,2-ylene group; alternatively, a 4-substituted cyclohex-1,2-ylene group; alternatively, a 3,4-disubstituted cyclohex-1,2-ylene group; alternatively, a 3,5-disubstituted cyclohex-1,2-ylene group; or alternatively, a 3,6-disubstituted cyclohex-1,2-ylene group. In an embodiment, the substituted cyclohex-1,3-ylene group can comprise a substituent at the 2-position, the 4-position, the 5-position, the 2- and 4-positions, the 1- and 5-positions, the 4- and 6-positions, or the 2-, 4-, and 6-positions; alternatively, the 2-position, the 4-position, or the 5-position; alternatively, the 2- and 4-positions, the 2- and 5-positions, or the 4- and 6-positions; alternatively, the 3-position; alternatively, the 4-position; alternatively, the 5-positions; alternatively, the 2- and 4-positions; alternatively, the 2- and 5-positions; alternatively, the 4- and 6-positions; or alternatively, 2-, 4-, and 6-positions. In some embodiments, the substituted cyclohex-1,3-ylene group which can be utilized as $R^2$ and/or $R^4$ can be a 2-substituted, 4-substituted, a 5-substituted, 2,4-disubstituted, 2,5-disubstituted, 4,6-disubstituted, or 2,4,6-trisubstituted cyclohex-1,3-ylene group; alternatively, a 2-substituted, 4-substituted, or 5-substituted cyclohex-1,3-ylene group; alternatively, a 2,4-disubstituted, 2,5-disubstituted, 4,6-disubstituted cyclohex-1,3-ylene group; alternatively, a 2-substituted cyclohex-1,3-ylene group; alternatively, a 4-substituted cyclohex-1,3-ylene group; alternatively, a 5-substituted cyclohex-1,3-ylene group; alternatively, a 2,4-disubstituted cyclohex-1,3-ylene group; alternatively, a 2,5-disubstituted cyclohex-1,3-ylene group; alternatively, a 4,6-disubstituted cyclohex-1,3-ylene group; or alternatively, a 2,4,6-trisubstituted cyclohex-1,3-ylene group. In an embodiment, the substituted cyclohex-1,4-ylene group can comprise a substituent at the 2-position, the 2- and 3-positions, the 2- and 5-positions, the 2- and 6-positions, the 2-, 3-, and 5-positions, or the 2-, 3-, 5-, and 6-positions; alternatively, the 2- and 3-positions, the 2- and 5-positions, or the 2- and 6-positions; alternatively, the 2-position; alternatively, the 2- and 3-positions; alternatively, the 2- and 5-positions; alternatively, the 2- and 6-positions; alternatively, the 2-, 3-, and 5-positions; or alternatively, the 2-, 3-, 5-, and 6-positions. In some embodiments, the substituted cyclohex-1,4-ylene group which can be utilized as $R^2$ and/or $R^4$ can be a 2-substituted, 2,3-disubstituted, 2,5-disubstituted, 2,6-disubstituted, 2,3,5-trisubstituted, or 2,3,5,6-tetrasubstituted cyclohex-1,4-ylene group; alternatively, a 2,3-disubstituted, 2,5-substituted, or 2,6-disubstituted cyclohex-1,4-ylene group; alternatively, a 2-substituted cyclohex-1,4-ylene group; alternatively, a 2,3-disubstituted cyclohex-1,4-ylene group; alternatively, a 2,5-disubstituted cyclohex-1,4-ylene group; alternatively, a 2,6-disubstituted cyclohex-1,4-ylene group; alternatively, a 2,3,5-triisubstituted cyclohex-1,4-ylene group; or alternatively, a 2,3,5,6-tetrasubstituted cyclohex-1,4-ylene group.

In an aspect, L of the pyridine bisimine ligand having Structure BPBI I and/or Structure BPBI III can be a bicyclohexylene group, a substituted bicyclohexylene group, a bis(cyclohexylene)methane group, a substituted bis(cyclohexylene)methane group, a bis(cyclohexylene)ethane group, a substituted bis(cyclohexylene)ethane group; alternatively, a bicyclohexylene group or a substituted bicyclohexylene group; alternatively, a bis(cyclohexylene)methane group or a substituted bis(cyclohexylene)methane group; alternatively, a bis(cyclohexylene)ethane group or a substituted bis(cyclohexylene)ethane group; alternatively, a bis(cyclohexylene) group, bis(cyclohexylene)methane group, or a bis(cyclohex-ylene)ethane group; alternatively, bis(cyclohexylene) group; alternatively, a bis(cyclohexylene)methane group; or alternatively, a bis(cyclohexylene)methane group. In an embodiment, L of the pyridine bisimine ligand having Structure BPBI I and/or Structure BPBI III can be a bicyclohex-3-ylene group, a substituted bicyclohex-3-ylene group, a bicyclohex-4-ylene group, or a substituted bicyclohex-4-ylene group; alternatively, a bicyclohex-3-ylene group or a substituted bicyclohex-3-ylene group; alternatively, a bicyclohex-4-ylene group or a substituted the bicyclohex-4-ylene group; alternatively, a bicyclohex-3-ylene group or a bicyclohex-4-ylene group; alternatively, a bicyclohex-3-ylene group; alternatively, a substituted bicyclohex-3-ylene group; alternatively, a bicyclohex-4-ylene group; or alternatively, a substituted bicyclohex-4-ylene group. In some embodiments, L of the pyridine bisimine ligand having Structure BPBI I and/or Structure BPBI III can be a bis(cyclohex-3-ylene)methane group, a substituted bis(cyclohex-3-ylene)methane group, a bis(cyclohex-4-ylene)methane group, or a substituted bis(cyclohex-4-ylene) methane group; alternatively, a bis(cyclohex-3-ylene)methane group or a substituted bis(cyclohex-3-ylene)methane group; alternatively, a bis(cyclohex-4-ylene)methane group or a substituted the bis(cyclohex-4-ylene)methane group; alternatively, a bis(cyclohex-3-ylene)methane group or a bis(cyclohex-4-ylene)methane group; alternatively, a bis(cyclohex-3-ylene)methane group; alternatively, a substituted bis(cyclohex-3-ylene)methane group; alternatively, a bis(cyclohex-4-ylene)methane group; or alternatively, a substituted bis(cyclohex-4-ylene)methane group. In other embodiments, L of the pyridine bisimine ligand having Structure BPBI I and/or Structure BPBI III can be a bis(cyclohex-3-ylene)ethane group, a substituted bis(cyclohex-3-ylene)ethane group, a bi(cyclohex-4-ylene)ethane group, or a substituted bis(cyclohex-4-ylene)ethane group; alternatively, a bis(cyclohex-3-ylene)ethane group or a substituted bis(cyclohex-3-ylene)ethane group; alternatively, a bis(cyclohex-4-ylene)ethane group or a substituted the bis(cyclohex-4-ylene)ethane group; alternatively, a bis(cyclohex-3-ylene)ethane group or a bis(cyclohex-4-ylene)ethane group; alternatively, a bis(cyclohex-3-ylene)ethane group; alternatively, a substituted bis(cyclohex-3-ylene)ethane group; alternatively, a bis(cyclohex-4-ylene)ethane group; or alternatively, a substituted bis(cyclohex-4-ylene)ethane group. Generally, any bis(cyclohexylene)ethane group disclosed herein (substituted or unsubstituted) can be a bis-1,1-(cyclohexylene)ethane group or a bis-1,2-(cyclo-hexylene)ethane group; alternatively, a bis-1,1-(cyclohexylene)ethane group; or alternatively, a bis-1,2-(cyclohexylene)ethane group.

In an embodiment, the arylene group (substituted or unsubstituted) which can be utilized as L of the pyridine bisimine ligand having Structure BPBI I and/or Structure BPBI III can be a $C_6$-$C_{40}$ arylene group (substituted or unsubstituted); alternatively, a $C_6$-$C_{20}$ arylene group (substituted or unsubstituted); alternatively, a $C_6$-$C_{15}$ arylene group (substituted or unsubstituted); or alternatively, a $C_6$-$C_{10}$ arylene group (substituted or unsubstituted). In other embodiments, L of the pyridine bisimine ligand having Structure BPBI I and/or Structure BPBI III can be a phenylene group, a substituted phenylene group, a naphthylene group, or a substituted naphthylene group; alternatively, a phenylene group or a substituted phenylene group; alternatively, a naphthylene group or a substituted naphthylene group; alternatively, a phenylene group or a naphthylene; alternatively, a phenylene group; alternatively, a substituted phenylene group; alternatively, a naphthylene group; or alternatively, a substituted naphthylene group. In an embodiment, L of the pyridine bisimine ligand having Structure BPBI I and/or Structure BPBI III can be a phen-1,2-ylene group, a substituted phen-1,2-ylene group, a phen-1,3-ylene group, a substituted phen-1,3-ylene group, a phen-1,4-ylene group, or a substituted phen-1,4-ylene group; alternatively, a phen-1,2-ylene group or a substituted phen-1,2-ylene group; alternatively, a phen-1,3-ylene group or a substituted phen-1,3-ylene group; alternatively, a phen-1,4-ylene group or a substituted phen-1,4-ylene group; alternatively, a phen-1,2-ylene group, a phen-1,3-ylene group, or a phen-1,4-ylene group; alternatively, a phen-1,2-ylene group; alternatively, a substituted phen-1,2-ylene group; alternatively, a phen-1,3-ylene group; alternatively, a substituted phen-1,3-ylene group; alternatively, a phen-1,4-ylene group; or alternatively, a substituted phen-1,4-ylene group.

In an aspect, L of the pyridine bisimine ligand having Structure BPBI I and/or Structure BPBI III can be a biphenylene group, a substituted biphenylene group, a bis(phenylene)methane group, a substituted bis(phenylene)methane group, a bis(phenylene)ethane group, or a substituted bis(phenylene)ethane group; alternatively, a biphenylene group or a substituted biphenylene group; alternatively, a bis(phenylene)methane group, or substituted bis(phenylene)methane group; alternatively, a bis(phenylene)ethane group or a substituted bis(phenylene)ethane group; alternatively, a biphenylene group, a bis(phenylene)methane group, or a bis(phenylene)ethane group; alternatively, a biphenylene group; alternatively, a substituted biphenylene group; alternatively, a bis(phenylene)methane group; alternatively, a substituted bis(phenylene)methane group; alternatively, a bis(phenylene)ethane group; or alternatively, a substituted bis(phenylene)ethane group. In an embodiment, L of the pyridine bisimine ligand having Structure BPBI I and/or Structure BPBI III can be a biphen-3-ylene group, a substituted biphen-3-ylene group, a biphen-4-ylene group, or a substituted biphen-4-ylene group; alternatively, a biphen-3-ylene group or a substituted biphen-3-ylene group; or alternatively, a biphen-4-ylene group or a substituted biphen-4-ylene group; alternatively, a biphen-3-ylene group or a biphen-4-ylene group; alternatively, a biphen-3-ylene group; alternatively, a substituted biphen-3-ylene group; alternatively, a biphen-4-ylene group; or alternatively, a substituted biphen-4-ylene group. In some embodiments, L of the pyridine bisimine ligand having Structure BPBI I and/or Structure BPBI III can be a bis(phen-3-ylene)methane group, a substituted bis(phen-3-ylene)methane group, a bis(phen-4-ylene)methane group, or a substituted bis(phen-4-ylene)methane group; alternatively, a bis(phen-3-ylene) methane group or a substituted bis(phen-3-ylene)methane group; alternatively, a bis(phen-4-ylene)methane group or a substituted bis(phen-4-ylene)methane group; alternatively, a bis(phen-3-ylene)methane group or a bis(phen-4-ylene) methane group; alternatively, a bis(phen-3-ylene)methane group; alternatively, a substituted bis(phen-3-ylene)methane group; alternatively, a bis(phen-4-ylene)methane group; or alternatively, a substituted bis(phen-4-ylene)methane group. In other embodiments, L of the pyridine bisimine ligand having Structure BPBI I and/or Structure BPBI III can be a bis(phen-3-ylene)ethane group, a substituted bis(phen-3-ylene)ethane group, a bis(phen-4-ylene)ethane group, or a substituted bis(phen-4-ylene)ethane group; alternatively, a bis(phen-3-ylene)ethane group or a substituted bis(phen-3-ylene)ethane group; or alternatively, a bis(phen-4-ylene) ethane group or a substituted bis(phen-4-ylene)ethane group; alternatively, a bis(phen-3-ylene)ethane group or a bis(phen-4-ylene)ethane group; alternatively, a bis(phen-3-ylene)ethane group; alternatively, a substituted bis(phen-3-ylene)ethane group; alternatively, a bis(phen-4-ylene)ethane group; or alternatively, a substituted bis(phen-4-ylene)ethane group. Generally, any bis(phenylene)ethane group disclosed herein (substituted or unsubstituted) can be a bis-1, 1-(phenylene)ethane group or a bis-1,2-(phenylene)ethane group; alternatively, a bis-1,1-(phenylene)ethane group; or alternatively, a bis-1,2-(phenylene)ethane group.

In an aspect, L of the pyridine bisimine ligand having Structure BPBI I and/or Structure BPBI III can be a fluorenylene group or a substituted fluorenylene group; a fluorenylene group; or alternatively, a substituted fluorenylene group. In some embodiments, L of the pyridine bisimine ligand having Structure BPBI I and/or Structure BPBI III can be a fluoren-2,7-ylene group or a substituted fluoren-2,7-ylene group; a fluoren-2,7-ylene group; or alternatively, a substituted fluoren-2,7-ylene group. In some embodiments, the substituted fluoren-2,7-ylene group can comprise a substituent at 3-position or a substituent at a 3- and a 6-position; alternatively, a substituent at 3-position; or alternatively, a substituent at a 3- and a 6-position. In other embodiments, the substituted fluoren-2,7-ylene group can be a 3-substituted fluoren-2,7-ylene group or a 3,6-disubstituted fluoren-2,7-ylene group; alternatively, a 3-substituted fluoren-2,7-ylene group; or alternatively, a 3,6-disubstituted fluoren-2,7-ylene group. In an embodiment the substituents of any fluorenylene group (general or specific) which can be utilized as L can be a halide, a hydrocarboxy group, or a hydrocarbyl group; alternatively, a halide or a hydrocarboxy group; alternatively, a halide or a hydrocarbyl group; alternatively, a hydrocarboxy group or a hydrocarbyl group; alternatively, a halide; alternatively, a hydrocarboxy group; or alternatively, a hydrocarbyl group. Halide substituents, hydrocarboxy substituent groups, and hydrocarbyl substituent group are independently disclosed herein and can be utilized without limitation to further describe a fluorenylene group which can be utilized as L.

In an aspect, L of the pyridine bisimine ligand having Structure BPBII and/or Structure MPBI III can have Structure 1L, 2L, 3L, 4L, 5L, 6L, 7L, 8L, 9L, 10L, 11L, 12L, 13L, and/or 14L; alternatively, Structure 1L, 2L, 3L, 4L, 5L, 6L, or 7L; or alternatively, 8L, 9L, 10L, 11L, 12L, 13L, or 14L. In some embodiments, L of the pyridine bisimine ligand having Structure BPBI I and/or Structure BPBI III can have Structure 1L, 2L, or 3L; alternatively, Structure 4L, 5L, 6L, or 7L; alternatively, Structure 8L, 9L, or 10L; or alternatively, Structure 11L, 12L, 13L, or 14L. In other embodiments, L of the pyridine bisimine ligand having Structure BPBI I and/or Structure BPBI III can have Structure 2L or 3L; alternatively, Structure 9L or 10L; alternatively, Structure 4L or 5L; alternatively, Structure 6L or 7L; or alternatively, Structure 11L or 12L; or alternatively, Structure 13L or 14L. In further embodiments, $L^1$ can have Structure 1L; alternatively, Structure 2L; alternatively, Structure 3L; alternatively, Structure 4L; alternatively, Structure 5L; alternatively, Structure 6L; alternatively, Structure 7L; alternatively, Structure 8L; alternatively, Structure 9L; alternatively, Structure 10L; alternatively, Structure 11L; alternatively, Structure 12L; alternatively, Structure 13L; or alternatively, Structure 14L.

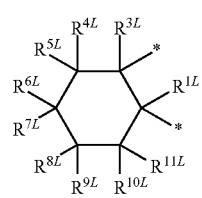

Structure 1L

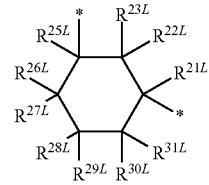

Structure 2L

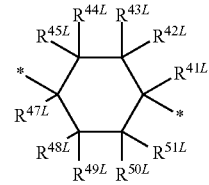

Structure 3L

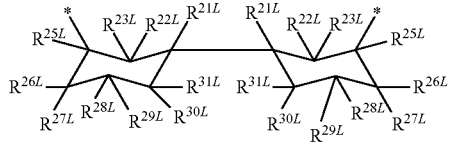

Structure 4L

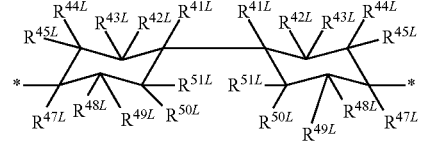

Structure 5L

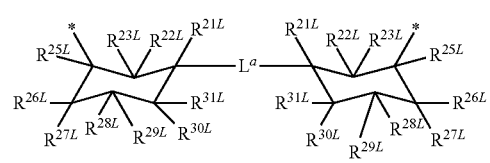

Structure 6L

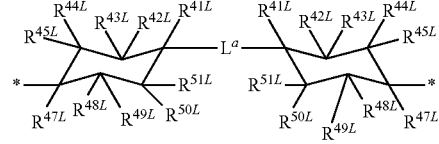

Structure 7L

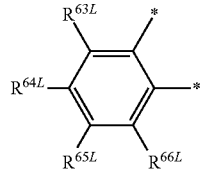

Structure 8L

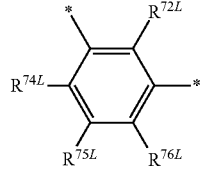

Structure 9L

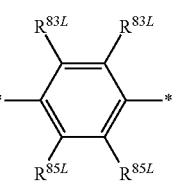

Structure 10L

-continued

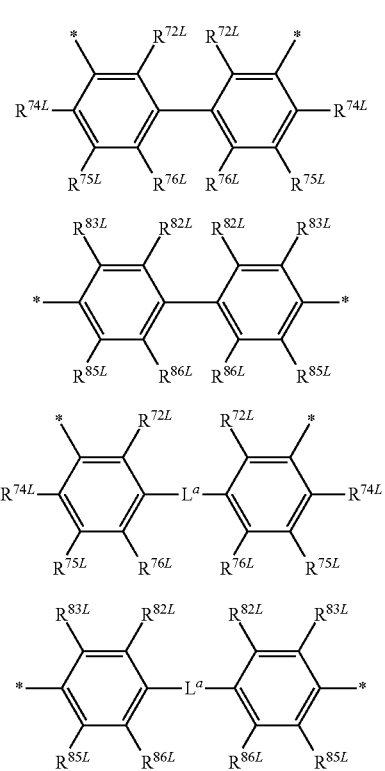

Structure 11L

Structure 12L

Structure 13L

Structure 14L

In an embodiment, $L^a$ within Structures 6L, 7L, 13L, or 14L, or L of the pyridine bisimine ligand having Structure BPBI I and/or Structure BPBI III can be $-(CR^L R^L)_m-$ where each $R^L$ independently can be hydrogen, methyl, ethyl, propyl, isopropyl, or butyl groups and m can be an integer from 1 to 5. In another embodiment, within $L^1$ Structures 6L, 7L, 13L, or 14L, $L^a$ can be $-CR^L R^L(CH_2)_n CR^L R^L-$ where each $R^L$ can independently be hydrogen, methyl, ethyl, propyl, isopropyl, or butyl groups and n can be an integer from 0 to 3. In some non-limiting embodiments, $L^a$ can be $-CH_2-$, $-CH_2CH_2-$, $-CH(CH_3)-$, $-CH_2CH_2CH_2-$, $-CH(CH_3)CH_2-$, $-C(CH_3)_2-$, or $-CH_2CH_2CH_2CH_2-$. In other non-limiting embodiments, $L^a$ can be $-CH_2-$, $-CH_2CH_2-$, $-CH_2CH_2CH_2-$, or $-CH(CH_3)CH_2-$; or alternatively, $-CH_2CH_2-$ or $-CH(CH_3)CH_2-$. In yet other embodiments, the linking group can be $-CH_2-$; alternatively, $-CH_2CH_2-$; alternatively, $-CH(CH_3)-$; alternatively, $-CH_2CH_2CH_2-$; alternatively, $-CH(CH_3)CH_2-$; or alternatively, $-C(CH_3)_2-$. In some embodiments, $L^a$ within Structures 6L, 7L, 13L, or 14L, or L of the pyridine bisimine ligand having Structure BPBI I and/or Structure BPBI III can be $-C(CF_3)_2-$. In yet other embodiments, $L^a$ can be $-O-$ or $-S-$; alternatively, $-O-$; or alternatively, $-S-$.

Generally, each $R^{1L}-R^{11L}$, $R^{21L}-R^{31L}$, $R^{41L}-R^{51L}$, $R^{62L}-R^{66L}$, $R^{72L}-R^{76L}$, and $R^{82L}-R^{82L}$, $R^{85L}-R^{86L}$ (when present in an indicated structure) independently can be hydrogen or a substituent group. In an embodiment, each non-hydrogen $R^{1L}-R^{11L}$, $R^{21L}-R^{31L}$, $R^{41L}-R^{51L}$, $R^{62L}-R^{66L}$, $R^{72L}-R^{76L}$, and $R^{82L}-R^{82L}$ $R^{85L}-R^{86L}$ can be a halide, a hydrocarboxy group, or a hydrocarbyl group; alternatively, a halide or a hydrocarboxy group; alternatively, a halide or a hydrocarbyl group; alternatively, a hydrocarboxy group or a hydrocarbyl group; alternatively, a halide; alternatively, a hydrocarboxy group; or alternatively, a hydrocarbyl group. Halide substituents, hydrocarboxy substituent groups, and hydrocarbyl substituent group are independently disclosed herein and can be utilized without limitation to further describe L having Structure 1L, 2L, 3L, 4L, 5L, 6L, 7L, 8L, 9L, 10L, 11L, 12L, 13L, and/or 14L.

In a non-limiting aspect of the pyridine bisimine ligand having Structure BPBI III, each carbon atom of L attached to the imine nitrogen atom can be an aromatic carbon atom and as such L can be any group described herein wherein each carbon atom of L attached to the imine nitrogen atom can be an aromatic carbon atom. In another non-limiting aspect of the pyridine bisimine ligand having Structure BPBI III, L can have Structure 8L, 9L, 10L, 11L, 12L, 13L, and/or 14L; alternatively, Structure 8L, 9L, or 10L; alternatively, Structure 11L, 12L, 13L, or 14L; alternatively, Structure 11L or 12L; alternatively, Structure 13L or 14L; alternatively, Structure 8L; alternatively, Structure 9L; alternatively, Structure 10L; alternatively, Structure 11L; alternatively, Structure 12L; alternatively, Structure 13L; or alternatively, Structure 14L.

In an embodiment, L of the pyridine bisimine ligand having Structure BPBI I and/or Structure BPBI III can be a phen-1,4-ylene group or a substituted phen-1,4-ylene group; alternatively, a phen-1,4-ylene group; or alternatively, a substituted phen-1,4-ylene group. In some embodiments, the substituted phen-1,4-ylene group which can be utilized as L of the pyridine bisimine ligand having Structure BPBI I and/or Structure BPBI III can comprise a substituent at the 2-position of the phen-1,4-ylene group, a substituent at the 2- and 3-positions of the phen-1,4-ylene group, or a substituent at the 2- and 6-positions of the phen-1,4-ylene group; alternatively, a substituent at the 2-position of the phen-1,4-ylene group; alternatively, a substituent at the 2- and 3-positions of the phen-1,4-ylene group; or alternatively, a substituent at the 2- and 6-positions of the phen-1,4-ylene group. In other embodiments, the substituted phen-1,4-ylene group which can be utilized as L of the pyridine bisimine ligand having Structure BPBI I and/or Structure BPBI III can be a 2-substituted phen-1,4-ylene group, a 2,3-disubstituted phen-1,4-ylene group, a 2,5-disubstituted phen-1,4-ylene group, a 2,6-disubstituted phen-1,4-ylene group, a 2,3,5-triisubstituted phen-1,4-ylene group, or a 2,3,5,6-tetrasubstituted phen-1,4-ylene group; alternatively, a 2,3-disubstituted phen-1,4-ylene group, a 2,5-substituted phen-1,4-ylene group, or a 2,6-disubstituted phen-1,4-ylene group; alternatively, a 2-substituted phen-1,4-ylene group; alternatively, a 2,3-disubstituted phen-1,4-ylene group; alternatively, a 2,5-disubstituted phen-1,4-ylene group; alternatively, a 2,6-disubstituted phen-1,4-ylene group; alternatively, a 2,3,5-triisubstituted phen-1,4-ylene group; or alternatively, a 2,3,5,6-tetrasubstituted phen-1,4-ylene group. Substituent groups are independently described herein and these substituent groups can be utilized without limitation to further describe the substituted phen-1,4-ylene group which can be utilized as L of the pyridine bisimine ligand having Structure BPBI I and/or Structure MPBI III.

In an non-limiting embodiment, the substituted phen-1,4-ylene group which can be utilized as L of the pyridine bisimine ligand having Structure BPBI I and/or Structure BPBI III can be a 2-methylphen-1,4-ylene group, a 2,3-dimethylphen-1,4-ylene group, a 2,5-dimethylphen-1,4-ylene group, a 2,6-dimethylphen-1,4-ylene group, a 2,3,5-trimethylphen-1,4-ylene group, or a 2,3,4,6-tetramethylphen-1,4-ylene group. In other non-limiting embodiments, the substituted phen-1,4-ylene group which can be utilized as L of the pyridine bisimine ligand having Structure BPBI I and/or Structure BPBI III can be a 2-methylphen-1,4-ylene group; alternatively, a 2,3-dimethylphen-1,4-ylene group; alternatively, a 2,5-dimethylphen-1,4-ylene group; alternatively, a 2,6-dimethylphen-1,4-ylene group; alternatively, a 2,3,5-trimethylphen-1,4-ylene group; or alternatively, a 2,3,4,6-tetramethylphen-1,4-ylene group.

In an embodiment, L of the pyridine bisimine ligand having Structure BPBI I and/or Structure BPBI III can be a fluor-2,7-ylene group or a substituted fluor-2,7-ylene group; alternatively, a fluor-2,7-ylene group; or alternatively, a substituted fluor-2,7-ylene group. In some embodiments, the substituted fluor-2,7-ylene group which can be utilized as L of the pyridine bisimine ligand having Structure BPBI I and/or Structure BPBI III can comprise a substituent at the 1- and 6-positions of the fluor-2,7-ylene group, a substituent at the 1- and 8-positions of the fluor-2,7-ylene group, or a substituent at the 3- and 6-positions of the fluor-2,7-ylene group; alternatively, a substituent at the 1- and 6-positions of the fluor-2,7-ylene group; alternatively, a substituent at the 1- and 8-positions of the fluor-2,7-ylene group; alternatively, a substituent at the 3- and 6-positions of the fluor-2,7-ylene group. In other embodiments, the substituted fluor-2,7-ylene group which can be utilized as L of the pyridine bisimine ligand having Structure BPBI I and/or Structure BPBI III can be a 1,6-disubstituted fluor-2,7-ylene group, a 1,8-disubstituted fluor-2,7-ylene group, or a 3,6-disubstituted fluor-2,7-ylene group; alternatively, a 1,6-disubstituted fluor-2,7-ylene group; alternatively, a 1,8-disubstituted fluor-2,7-ylene group; alternatively, a 3,6-disubstituted fluor-2,7-ylene group. Substituent groups are independently described herein and these substituent groups can be utilized without limitation to further describe the substituted fluor-2,7-ylene group which can be utilized as L of the pyridine bisimine ligand having Structure BPBI I and/or Structure MPBI III. In some embodiments, the substituted fluor-2,7-ylene group which can be utilized as L of the pyridine bisimine ligand having Structure BPBI I and/or Structure BPBI III can be a 1-methylfluor-2,7-ylene group, a 1,6-dimethylfluor-2,7-ylene group, a 1,8-dimethylfluor-2,7-ylene group, a 3-methylfluor-2,7-ylene group, or a 3,6-dimethylfluor-2,7-ylene group; alternatively, a 1-methylfluor-2,7-ylene group, a 1,6-dimethylfluor-2,7-ylene group, or a 1,8-dimethylfluor-2,7-ylene group; alternatively, a 3-methylfluor-2,7-ylene group or a 3,6-dimethylfluor-2,7-ylene group; alternatively, a 1-methylfluor-2,7-ylene group; alternatively, a 3-methylfluor-2,7-ylene group; alternatively, a 1,6-dimethylfluor-2,7-ylene group; alternatively, a 1,8-dimethylfluor-2,7-ylene group; or alternatively, a 3,6-dimethylfluor-2,7-ylene group.

In an embodiment, L of the pyridine bisimine ligand having Structure BPBI I and/or Structure BPBI III can be a biphen-4,4'-ylene group or a substituted biphen-4,4'-ylene group; alternatively, a biphen-4,4'-ylene group; or alternatively, a substituted biphen-4,4'-ylene group. In some embodiments, the substituted biphen-4,4'-ylene group which can be utilized as L of the pyridine bisimine ligand having Structure BPBI I and/or Structure BPBI III can comprise a substituent at the 2- and 2'-positions of the biphen-4-ylene group, a substituent at the 3- and 3'-positions of the biphen-4,4'-ylene group, a substituent at the 3-, 3'-, 5-, and 5'-positions of the biphen-4,4'-ylene group; alternatively, a substituent at the 2- and 2'-positions of the biphen-4,4'-ylene group; alternatively, a substituent at the 3- and 3'-positions of the biphen-4,4'-ylene group; or alternatively, a substituent at the 3-, 3'-, 5-, and 5'-positions of the biphen-4,4'-ylene group. In other embodiments, the substituted biphen-4,4'-ylene group which can be utilized as L of the pyridine bisimine ligand having Structure BPBI I and/or Structure BPBI III can be a 2,2'-disubstituted biphen-4,4'-ylene group, a 3,3'-disubstituted biphen-4,4'-ylene group, or a 3,3',5,5'-tetrasubstituted biphen-4,4'-ylene group; alternatively, a 2,2'-disubstituted biphen-4,4'-ylene group; alternatively, a 3,3'-disubstituted biphen-4,4'-ylene group; or alternatively, a 3,3',5,5'-tetrasubstituted biphen-4,4'-ylene group. Substituent groups are independently described herein and these substituent groups can be utilized without limitation to further describe the substituted biphen-4,4'-ylene group which can be utilized as L of the pyridine bisimine ligand having Structure BPBI I and/or Structure MPBI III. In an non-limiting embodiment, the substituted biphen-4-ylene group which can be utilized as L of the pyridine bisimine ligand having Structure BPBI I and/or Structure BPBI III can be a 3,3'-dimethyl biphen-4,4'-ylene group or a 3,3',5,5'-tetramethyl biphen-4,4'-ylene group; alternatively, a 3,3'-dimethyl biphen-4,4'-ylene group; or alternatively, a 3,3',5,5'-tetramethyl biphen-4,4'-ylene group.

In an embodiment, L of the pyridine bisimine ligand having Structure BPBI I and/or Structure BPBI III can be a diphen-3,3'-ylene methane group, a substituted diphen-3,3'-ylene methane group, a diphen-4,4'-ylene methane group, or a substituted diphen-4,4'-ylene methane group; alternatively, a diphen-3,3'-ylene methane group or a substituted diphen-3,3'-ylene methane group; alternatively, a diphen-4,4'-ylene methane group or a substituted diphen-4,4'-ylene methane group; alternatively, a diphen-3,3'-ylene methane group; alternatively, a substituted diphen-3,3'-ylene methane group; alternatively, a diphen-4,4'-ylene methane group; or alternatively, a substituted diphen-4,4'-ylene methane. In some embodiments, the substituted diphen-3,3'-ylene methane group which can be utilized as L of the pyridine bisimine ligand having Structure BPBI I and/or Structure BPBI III can comprise a substituent at the 2- and 2'-positions of the diphen-3,3'-ylene methane group, a substituent at the 4- and 4'-positions of the diphen-3,3'-ylene methane group, or a substituent at the 2-, 2'-, 4-, and 4'-positions of the diphen-3,3'-ylene methane group; alternatively, a substituent at the 2- and 2'-positions of the diphen-3,3'-ylene methane group; alternatively, a substituent at the 4- and 4'-positions of the diphen-3,3'-ylene methane group; or alternatively, a substituent at the 2-, 2'-, 4-, and 4'-positions of the diphen-4,4'-ylene methane group. In other embodiments, the substituted diphen-3,3'-ylene methane group which can be utilized as L of the pyridine bisimine ligand having Structure BPBI I and/or Structure BPBI III can be a 2,2'-disubstituted diphen-3,3'-ylene methane group, a 4,4'-disubstituted diphen-3,3'-ylene methane group, or a 2,2',4,4'-tetrasubstituted diphen-3,3'-ylene methane group; alternatively, a 2,2'-disubstituted diphen-3,3'-ylene methane group; alternatively, a 4,4'-disubstituted diphen-3,3'-ylene methane group; or alternatively, a 2,2',4,4'-tetrasubstituted diphen-3,3'-ylene methane group. In some embodiments, the substituted diphen-4,4'-ylene methane group which can be utilized as L of the pyridine bisimine ligand having Structure BPBI I and/or Structure BPBI III can comprise a substituent at the 2- and 2'-positions of the diphen-4,4'-ylene methane group, a substituent at the 3- and 3'-positions of the diphen-4,4'-ylene methane group, or a substituent at the 3-, 3'-, 5-, and 5'-positions of the diphen-4,4'-ylene methane group; alternatively, a substituent at the 2- and 2'-positions of the diphen-4,4'-ylene methane group; alternatively, a substituent at the 3- and 3'-positions of the diphen-4,4'-ylene methane group; alternatively, a substituent at the 3-, 3'-, 5-, and 5'-positions of the diphen-4,4'-ylene methane group. In other embodiments, the substituted diphen-4,4'-ylene methane group which can be utilized as L of the pyridine bisimine ligand having Structure BPBI I and/or Structure BPBI III can be a 2,2'-disubstituted diphen-4,4'-ylene methane group, a 3,3'-disubstituted diphen-4,4'-ylene methane group, or a 3,3',5,5'-tetrasubstituted diphen-4,4'-ylene methane group; alternatively, a 2,2'-disubstituted diphen-4,4'-ylene methane group; alternatively, a 3,3'-disubstituted diphen-4,4'-ylene methane group; or alternatively, a 3,3',5,5'-tetrasubstituted diphen-4,4'-ylene methane group. Substituent groups are independently described herein and these substituent groups can be utilized without limitation to further describe the substituted diphen-4,4'-ylene methane group which can be utilized as L of the pyridine bisimine ligand having Structure BPBI I and/or Structure MPBI III. In some non-limiting embodiments, the substituted diphen-3,3'-ylene methane group which can be utilized as L of the pyridine bisimine ligand having Structure BPBI I and/or Structure BPBI III can be a 2,2'-dimethyl phen-3,3'-ylene methane group or a 2,2',4,4'-tetramethyl phen-3,3'-ylene methane group; alternatively, a 2,2'-dimethyl phen-3,3'-ylene methane group; or alternatively, a 2,2',4,4'-tetramethyl phen-4,4'-ylene methane group. In other non-limiting embodiments, the substituted diphen-4,4'-ylene methane group which can be utilized as L of the pyridine bisimine ligand having Structure BPBI I and/or Structure BPBI III can be a 3,3'-dimethyl phen-4,4'-ylene methane group or a 3,3',5,5'-tetramethyl phen-4,4'-ylene methane group; alternatively, a 3,3'-dimethyl phen-4,4'-ylene methane group; or alternatively, a 3,3',5,5'-tetramethyl phen-4,4'-ylene methane group.

In an embodiment, L of the pyridine bisimine ligand having Structure BPBI I and/or Structure BPBI III can be a 1,2-di(phen-4-ylene)ethane group or a substituted 1,2-di(phen-4-ylene)ethane group; alternatively, a 1,2-di(phen-4-ylene)ethane group; or alternatively, a substituted 1,2-di(phen-4-ylene) ethane. In some embodiments, the substituted 1,2-di(phen-4-ylene)ethane group which can be utilized as L of the pyridine bisimine ligand having Structure BPBI I and/or Structure BPBI III can comprise a substituent at each of the phenyl group 2-positions of the 1,2-di(phen-4-ylene)ethane group, a substituent at each of the phenyl group 3-positions of the 1,2-di(phen-4-ylene) ethane group, or a substituent at each of the phenyl group 3- and 5-positions of the 1,2-di(phen-4-ylene)ethane group; alternatively, a substituent at each of the phenyl group 2-positions of the 1,2-di(phen-4-ylene)ethane group; alternatively, a substituent at each of the phenyl group 3-positions of the 1,2-di(phen-4-ylene)ethane group; alternatively, a substituent at each of the phenyl group 3- and 5-positions of the 1,2-di(phen-4-ylene)ethane group. In some embodiments, the substituted 1,2-di(phen-4-ylene)ethane group which can be utilized as L of the pyridine bisimine ligand having Structure BPBI I and/or Structure BPBI III L can be a 1,2-di(2-substituted phen-4-ylene)ethane group, a 1,2-di(3-substituted phen-4-ylene) ethane group, or a 1,2-di(3,5-disubstituted phen-4-ylene)ethane group; alternatively, a 1,2-di(2-substituted phen-4-ylene)ethane group; alternatively, a 1,2-di(3-substituted phen-4-ylene)ethane group; or alternatively, a 1,2-di(3,5-disubstituted phen-4-ylene)ethane group. Substituent groups are independently described herein and these substituent groups can be utilized without limitation to further describe the bis(phen-4-ylene)ethane group which can be utilized as L of the pyridine bisimine ligand having Structure BPBI I and/or Structure MPBI III. In some non-limiting embodiments, the substituted 1,2-di(phen-4-ylene) ethane group which can be utilized as L of the pyridine bisimine ligand having Structure BPBI I and/or Structure BPBI III L can be a 1,2-di(2-methylphen-4-ylene)ethane group, a 1,2-di(3-methylphen-4-ylene)ethane group, or a 1,2-di(3,5-dimethylphen-4-ylene)ethane group; alternatively, a 1,2-di(2-methylphen-4-ylene)ethane group; alternatively, a 1,2-di(3-methylphen-4-ylene) ethane group; or alternatively, a 1,2-di(3,5-dimethylphen-4-ylene)ethane group.

In an independent aspect, $R^1$ and $R^2$, $R^2$ and $R^3$, $R'$ and $R^4$, and/or $R^3$ and $R^5$ taken together can form a ring or ring system. In such aspects, $R^1$ and $R^2$, $R^2$ and $R^3$, $R^1$ and $R^4$, and/or $R^3$ and $R^5$ taken together can form an organylene group; alternatively, an organylene group consisting of inert functional group; or a hydrocarbylene group. Organylene groups, organylene groups consisting of inert functional groups, and hydrocarbylene groups are independently disclosed herein as potential L groups and these groups can be utilized without limitation to describe the combined $R^1$ and $R^2$, $R^2$ and $R^3$, $R'$ and $R^4$, and/or $R^3$ and $R^5$. In some embodiments, the combined $R^1$ and $R^2$, the combined $R^2$ and $R^3$, the combined $R^1$ and $R^4$, and/or the combined $R^3$ and $R^5$ in addition with the other atoms of the pyridine bisimine ligand forming the ring can form an aromatic ring (e.g., a phenyl ring).

In a non-limiting embodiment where $R^1$ and $R^4$ and $R^3$ and $R^5$ each form a ring, the pyridine bisimine ligand can have Structure PBI IV, Structure PBI V, Structure PBI VI, Structure BPBI IV, or Structure BPBI VI; alternatively, Structure PBI IV, Structure PBI V, or Structure PBI VI; alternatively, Structure BPBI IV or Structure BPBI VI; alternatively, Structure PBI V or Structure PBI VI; alternatively, Structure PBI IV; alternatively, Structure PBI V; alternatively, Structure PBI VI; alternatively, Structure BPBI IV; or alternatively, Structure BPBI VI.

Structure PBI IV

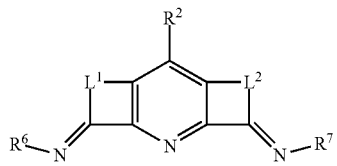

Structure PBI V

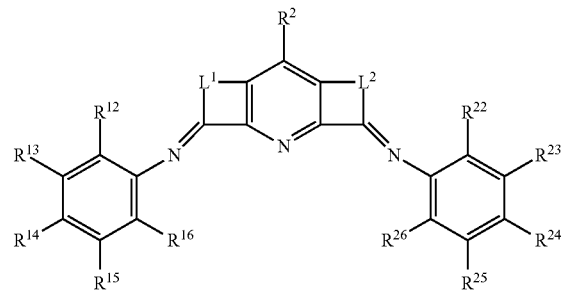

Structure PBI VI

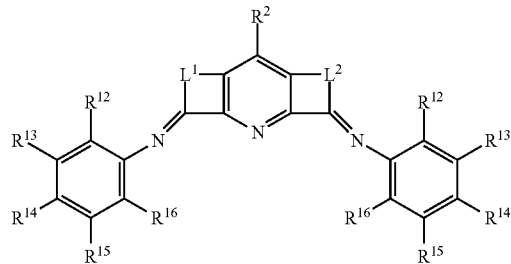

Structure BPBI IV

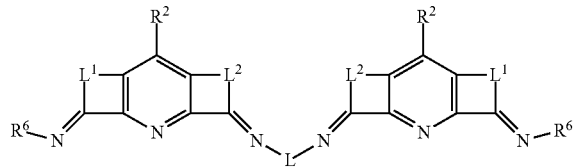

Structure BPBI VI

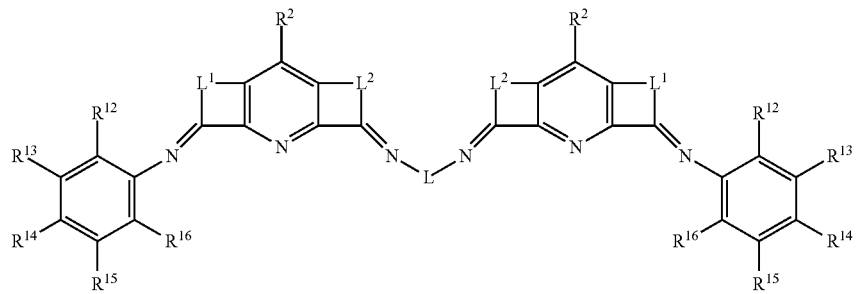

Generally, $R^2 R^6$, $R^7$, $R^{12}$, $R^{13}$, $R^{14}$, $R^{15}$, $R^{16}$, $R^{22}$, $R^{23}$, $R^{24}$, $R^{25}$, $R^{26}$, L, $L^1$, and $L^2$ are independent elements of the respective pyridine bisimine ligands having Structure PBI IV, Structure PBI V, Structure PBI VI, Structure BPBI IV, and/or Structure BPBI VI. These elements of the pyridine bisimine ligands having Structure PBI IV, Structure PBI V, Structure PBI VI, Structure BPBI IV, and/or Structure BPBI VI are independently described herein and the pyridine bisimine ligands having Structure PBI IV, Structure PBI V, Structure PBI VI, Structure BPBI IV, and/or Structure BPBI VI can be described using any combination of these herein independently described elements.

$R^2$, $R^6$, $R^7$, $R^{12}$, $R^{13}$, $R^{14}$, $R^{15}$, $R^{16}$, $R^{22}$, $R^{23}$, $R^{24}$, $R^{25}$, and $R^{26}$ are independently described herein as groups for the pyridine bisimine ligands having Structure PBI I, Structure PBI II, Structure PBI III, Structure BPBI I, and/or Structure BPBI III. These aspects and embodiments of $R^2$, $R^{12}$, $R^{13}$, $R^{14}$, $R^{15}$, $R^{16}$, $R^{22}$, $R^{23}$, $R^{24}$, $R^{25}$, and $R^{26}$ can be utilized without limitation to further describe the pyridine bisimine ligands having Structure PBI IV, Structure PBI V, Structure PBI VI, Structure BPBI IV, or Structure BPBI VI. L is independently described herein as a linking group for the pyridine bisimine ligands having Structure BPBI I and/or Structure MPBI III. These aspects and embodiments of L can be utilized without limitation to further describe the pyridine bisimine ligands having Structure PBI IV or Structure PBI VI.

In an aspect, $L^1$ can be an organylene group; alternatively, an organylene group consisting of inert functional groups; or alternatively, a hydrocarbylene group. In an aspect, $L^2$ can be an organylene group; alternatively, an organylene group consisting of inert functional groups; or alternatively, a hydrocarbylene group. Organylene groups, organylene groups consisting of inert functional groups, and hydrocarbylene groups are independently disclosed herein as potential L groups and these groups can be utilized without limitation as $L^1$ and/or $L^2$. In an embodiment, $L^1$ and $L^2$ can be different. In other embodiments, $L^1$ and $L^2$ can be the same.

In an aspect, $L^1$ can have the structure $-(CR^{41}R^{42})_p-$ and $L^2$ can have the structure $-(CR^{43}R^{44})_q-$. Generally, $R^{41}$, $R^{42}$, and p are independent features of $L^1$ having the structure $-(CR^{41}R^{42})_p-$ and $R^{41}$, $R^{42}$, and q are independent features of $L^2$ having the structure $-(CR^{43}R^{44})_p-$. Consequently, the pyridine bisimine ligands having Structure PBI IV, Structure PBI V, Structure PBI V, Structure PBI IV, and/or Structure PBI VI can be described using any combination of $R^{41}$ described herein, $R^{42}$ described herein, $R^{43}$ described herein, $R^{44}$ described herein, p described herein, and q described herein.

In an embodiment, each $R^{41}$, $R^{42}$, $R^{43}$, and $R^{44}$ independently can be hydrogen, an inert functional group, or an organyl group; alternatively, hydrogen or an organyl group; alternatively, an inert functional group or an organyl group; alternatively, hydrogen, an inert functional group, or an organyl group consisting of inert functional groups; alternatively, hydrogen or an organyl group consisting of inert functional groups; alternatively, an inert functional group or an organyl group consisting of inert functional groups; alternatively, hydrogen, an inert functional group, or a hydrocarbyl group; alternatively, hydrogen or a hydrocarbyl group; alternatively, an inert functional group or a hydrocarbyl group; alternatively, alternatively, hydrogen or an inert functional group; alternatively, hydrogen; alternatively, an organyl group; alternatively, organyl group consisting of inert functional groups; or alternatively, a hydrocarbyl group. Inert functional groups, organyl groups, organyl groups consisting of inert functional group, and hydrocarbyl group are described herein as potential $R^1$, $R^2$, $R^3$, $R^{12}$, $R^{13}$, $R^{14}$, $R^{15}$, $R^{16}$, $R^{22}$, $R^{23}$, $R^{24}$, $R^{25}$, and $R^{26}$ groups within the pyridine bisimine ligands having Structure PBI I, Structure PBI II, Structure PBI III, Structure BPBI I, and Structure BPBI III. These aspects and embodiments of $R^1$, $R^2$, $R^3$, $R^{12}$, $R^{13}$, $R^{14}$, $R^{15}$, $R^{16}$, $R^{22}$, $R^{23}$, $R^{24}$, $R^{25}$, and $R^{26}$ groups can be utilized without limitation to further describe $R^{41}$, $R^{42}$, $R^{43}$, and $R^{44}$ within the pyridine bisimine ligands having Structure PBI IV, Structure PBI V, Structure PBI VI, Structure BPBI I, and Structure BPBI III. In an aspect, p and q independently can be an integer from 1 to 5; alternatively, an integer from 1 to 3; alternatively, an integer from 2 to 3; alternatively, 1; alternatively, 2; alternatively, 3; alternatively, 4; or alternatively, 5.

In some non-limiting embodiments, each $R^{41}$, $R^{42}$, $R^{43}$, and $R^{44}$ independently can be hydrogen, a methyl group, an ethyl group, a propyl group, an isopropyl group, or a butyl group and p and q independently can be an integer from 1 to 5. In another non-limiting embodiment, each $R^{41}$, $R^{42}$, $R^{43}$, and $R^{44}$ independently can be hydrogen, methyl, ethyl, propyl, isopropyl, or butyl groups and n can be an integer from 1 to 3. In yet other non-limiting embodiments, the $L^1$ and $L^2$ independently can be —$CH_2$—, —$CH_2CH_2$—, —$CH_2CH_2CH_2$—, —$CH(CH_3)CH_2$—, —$C(CH_3)_2$—, or —$CH_2CH_2CH_2CH_2$—; alternatively, —$CH_2CH_2$— or —$CH_2CH_2CH_2$—; alternatively, —$CH_2CH_2$—; or alternatively, —$CHCH_2CH_2$—. In an embodiment, $L^1$ and $L^2$ can be different. In other embodiments, $L^1$ and $L^2$ can be the same.

In another independent aspect, any two of $R^{12}$, $R^{13}$, $R^{14}$, $R^{15}$, $R^{16}$, $R^{22}$, $R^{23}$, $R^{24}$, $R^{25}$ and $R^{26}$ vicinal to one another can be taken together can to form a ring. In such aspects, the vicinal $R^{12}$, $R^{13}$, $R^{14}$, $R^{15}$, $R^{16}$, $R^{22}$, $R^{23}$, $R^{24}$, $R^{25}$, and $R^{26}$ taken together can form an organylene group; alternatively, an organylene group consisting of inert functional group; or a hydrocarbylene group. Organylene groups, organylene groups consisting of inert functional groups, and hydrocarbylene groups are independently disclosed herein as potential L groups and these groups can be utilized without limitation to describe the combined vicinal $R^{12}$, $R^{13}$, $R^{14}$, $R^{15}$, $R^{16}$, $R^{22}$, $R^{23}$, $R^{24}$, $R^{25}$, and $R^{26}$. In some embodiments, the combined vicinal $R^{12}$, $R^{13}$, $R^{14}$, $R^{15}$, $R^{16}$, $R^{22}$, $R^{23}$, $R^{24}$, $R^{25}$, and $R^{26}$ in addition with the other atoms of the pyridine bisimine ligand forming the ring can form an aromatic ring (e.g., a phenyl ring).

In another independent aspect, $R^5$ and $R^{12}$ (or alternatively, $R^5$ and $R^{16}$) and/or $R^4$ and $R^{22}$ (or alternatively, $R^4$ and $R^{26}$) taken together can form a ring or ring system. In such aspects, $R^5$ and $R^{12}$ (or alternatively, $R^5$ and $R^{16}$) and/or $R^4$ and $R^{22}$ (or alternatively, $R^4$ and $R^{26}$) taken together can form an organylene group; alternatively, an organylene group consisting of inert functional group; or alternatively, a hydrocarbylene group. Organylene groups, organylene groups consisting of inert functional groups, and hydrocarbylene groups are independently disclosed herein as potential L groups and these groups can be utilized without limitation to describe the combined $R^5$ and $R^{12}$ (or alternatively, $R^5$ and $R^{16}$) and/or $R^4$ and $R^{22}$ (or alternatively, $R^4$ and $R^{26}$). In some embodiments, the combined $R^5$ and $R^{12}$ (or alternatively, $R^5$ and $R^{16}$) and/or $R^4$ and $R^{22}$ (or alternatively, $R^4$ and $R^{26}$) in addition with the other atoms of the pyridine bisimine ligand forming the ring can form an aromatic ring (e.g., a pyridine ring). In the instance where the combined $R^5$ and $R^{12}$ (or alternatively, $R^5$ and $R^{16}$) and/or $R^4$ and $R^{22}$ (or alternatively, $R^4$ and $R^{26}$) in addition with the other atoms of the pyridine bisimine ligand forming the ring can form a pyridine ring, the combined $R^5$ and $R^{12}$ (or alternatively, $R^5$ and $R^{16}$) and/or $R^4$ and $R^{22}$ (or alternatively, $R^4$ and $R^{26}$) can be an ethen-1,2-ylene group or a substituted ethen-1,2-ylene group; alternatively, an ethen-1,2-ylene group; or alternatively, a substituted ethen-1,2-ylene group. In an embodiment, the substituents of the substituted ethen-1,2-ylene group which can be utilized as the combined $R^5$ and $R^{12}$ (or alternatively, $R^5$ and $R^{16}$) and/or $R^4$ and $R^{22}$ (or alternatively, $R^4$ and $R^{26}$) can be a halide, a hydrocarboxy group, or a hydrocarbyl group; alternatively, a halide or a hydrocarboxy group; alternatively, a halide or a hydrocarbyl group; alternatively, a hydrocarboxy group or a hydrocarbyl group; alternatively, a halide; alternatively, a hydrocarboxy group; or alternatively, a hydrocarbyl group. Halide substituents, hydrocarboxy substituent groups, and hydrocarbyl substituent groups are independently disclosed herein and can be utilized without limitation to further describe the substituted ethen-1,2-ylene group which can be utilized as the combined $R^5$ and $R^{12}$ (or alternatively, $R^5$ and $R^{16}$) and/or $R^4$ and $R^{22}$ (or alternatively, $R^4$ and $R^{26}$).

In a non-limiting embodiment of the pyridine bisimine ligand having Structure PBI I, Structure PBI II, Structure PBI III, Structure BPBI I, and/or Structure BPBI III, each $R^1$, $R^2$, and $R^3$ can be hydrogen. In a non-limiting embodiment for the pyridine bisimine ligands having Structure PBI I, Structure PBI II, Structure PBI III, Structure BPBI I, and/or Structure BPBI III, each $R^4$ and $R^5$ independently can be hydrogen, a methyl group, or a phenyl group; alternatively, hydrogen or a methyl group; alternatively, hydrogen; alternatively, a methyl group; or alternatively, a phenyl group. In some other non-limiting embodiments of the pyridine bisimine ligand having Structure PBI I, Structure PBI II, Structure PBI III, Structure BPBI I, and/or Structure BPBI III, each $R^1$, $R^2$, and $R^3$ can be hydrogen and each $R^4$ and $R^5$ independently can be a methyl group. Other aspects and embodiments of $R^1$, $R^2$, and $R^3$, and $R^4$ and $R^5$ are readily apparent from the present disclosure. Other embodiments for the combination of aspect and embodiments of $R^1$, $R^2$, and $R^3$, and aspects and embodiments of $R^4$ and R are readily apparent from the present disclosure. Within these non-limiting embodiments of the pyridine bisimine ligand having Structure PBI I, Structure PBI II, Structure PBI III, Structure BPBI I, and/or Structure BPBI III, the remaining pyridine bisimine ligand groups can be any group(s) or have any features described herein consistent with the features related to $R^1$, $R^2$, and $R^3$, and $R^4$ and $R^5$.

In a non-limiting of the pyridine bisimine ligand having Structure PBI IV, Structure PBI V, Structure PBI VI, Structure BPBI IV, and/or Structure BPBI VI, each $R^2$ can be hydrogen. In a non-limiting of the pyridine bisimine ligand having Structure PBI IV, Structure PBI V, Structure PBI VI, Structure BPBI IV, and/or Structure BPBI VI, each $L^1$ and $L^2$ independently can be —$CH_2CH_2$— or —$CH_2CH_2CH_2$—; alternatively, —$CH_2CH_2$—; or alternatively, —$CH_2CH_2CH_2$—. Other aspects and embodiments of $R^2$, and $L^1$ and $L^2$ are readily apparent from the present disclosure. Other embodiments for the combination of aspect and embodiments of $R^2$, and aspects and embodiments of $L^1$ and $L^2$ are readily apparent from the present disclosure. Within these non-limiting embodiments of the pyridine bisimine ligand having Structure PBI IV, Structure PBI V, Structure PBI VI, Structure BPBI IV, and/or Structure BPBI VI, the remaining pyridine bisimine ligand groups can be any group(s) or have any features described herein consistent with the features related to $R^2$, and $L^1$ and $L^2$.

In a non-limiting embodiment of the pyridine bisimine ligands having Structure PBI II, Structure PBI III, Structure PBI V, and/or Structure PBI VI, the pyridine bisimine ligand can have a structure wherein $R^{12}$, $R^{16}$, $R^{22}$, and $R^{26}$ independently can be hydrogen or any non-hydrogen group described herein. In some embodiments, the non-hydrogen group which can be utilized for any of $R^{12}$, $R^{16}$, $R^{22}$, and/or $R^{26}$ can be an inert functional group, a primary carbon group, a secondary carbon group, a tertiary carbon group, or a quaternary carbon group; alternatively, a halogen, a primary carbon group, a secondary carbon group, a tertiary carbon group, or a quaternary carbon group; alternatively, primary carbon group, a secondary carbon group, a tertiary carbon group, or a quaternary carbon group; alternatively, a primary carbon group or a secondary carbon group; alternatively, and inert functional group; alternatively, a halogen; alternatively, a primary carbon group; alternatively, a secondary carbon group; alternatively, a tertiary carbon group; or alternatively, a quaternary carbon group.

In a non-limiting embodiment of the pyridine bisimine ligands having Structure PBI II, Structure PBI III, Structure PBI V, and/or PBI VI, the pyridine bisimine ligand can have a structure wherein at least one of $R^{12}R^{16}R^{22}$, $R^{22}$, and $R^{26}$ can be any non-hydrogen group described herein and the remainder of $R^{12}$, $R^{16}$, and $R^{26}$ can be hydrogen; alternatively, wherein one of $R^{12}$, $R^{16}$, $R^{22}$, and $R^{26}$ can be any non-hydrogen group described herein and the remainder of $R^{12}$, $R^{16}$, $R^{22}$, and $R^{26}$ can be hydrogen; alternatively, wherein two of $R^{12}$, $R^{16}$, $R^{22}$, and $R^{26}$ independently can be any non-hydrogen group described herein and the remainder of $R^{12}$, $R^{16}$, $R^{22}$, and $R^{26}$ can be hydrogen; or alternatively, wherein three of $R^{12}$, $R^{16}$, $R^{22}$, and $R^{26}$ independently can be any non-hydrogen group described herein and the remainder of $R^{12}$, $R^{16}$, $R^{22}$, and $R^{26}$ can be hydrogen. In another non-limiting embodiment of the pyridine bisimine ligands having Structure PBI II, Structure PBI III, Structure PBI V, and/or PBI VI, the pyridine bisimine ligand can have a structure wherein at least one of $R^{12}$, $R^{16}$, $R^{22}$, and $R^{26}$ can be any non-hydrogen group described herein, the remainder of $R^{12}$, $R^{16}$, $R^{22}$, and $R^{26}$ can be hydrogen, and $R^{13}$, $R^{14}$, $R^{15}$, $R^{23}$ (if present), $R^{24}$ (if present), and $R^{25}$ (if present) can be hydrogen; alternatively, wherein one of $R^{12}$, $R^{16}$, $R^{22}$, $R^{22}$, and $R^{26}$ can be any non-hydrogen group described herein, the remainder of $R^{12}$, $R^{16}$, $R^{22}$, and $R^{26}$ can be hydrogen, and $R^{13}$, $R^{14}$, $R^{15}$, $R^{23}$ (if present), $R^{24}$ (if present), and $R^{25}$ (if present) can be hydrogen; alternatively, two of $R^{12}$, $R^{16}$, $R^{22}$, and $R^{26}$ independently can be any non-hydrogen group described herein, the remainder of $R^{12}$, $R^{16}$, $R^{22}$, and $R^{26}$ can be hydrogen, and $R^{13}$, $R^{14}$, $R^{15}$, $R^{23}$ (if present), $R^{24}$ (if present), and $R^{25}$ (if present) can be hydrogen; or alternatively, three of $R^{12}$, $R^{16}$, $R^{22}$, and $R^{26}$ independently can be any non-hydrogen group described herein, the remainder of $R^{12}$, $R^{16}$, $R^{22}$, and $R^{26}$ can be hydrogen, and $R^{13}$, $R^{14}$, $R^{15}$, $R^{23}$ (if present), $R^{24}$ (if present), and $R^{25}$ (if present) can be hydrogen. In an embodiment of the pyridine bisimine ligand having Structure PBI II and/or Structure PBI V, the pyridine bisimine ligand can have a structure wherein $R^{12}$ and $R^{16}$ are different from $R^{22}$ and $R^{26}$; or alternatively, wherein $R^{12}$ and $R^{16}$ are the same as $R^{22}$ and $R^{26}$. In some embodiments of the pyridine bisimine ligand having Structure PBI I or PBI IV, the pyridine bisimine ligand can have a structure wherein $R^6$ and $R^7$ are different (i.e., $R^{12}$, $R^{13}$, $R^{14}$, $R^{15}$, and $R^{16}$ are not exactly the same as $R^{22}$, $R^{23}$, $R^{24}$, $R^{25}$, and $R^{26}$); or alternatively, wherein $R^6$ and $R^7$ are the same (i.e., $R^{12}$, $R^{13}$, $R^{14}$, $R^{15}$, and $R^{16}$ are exactly the same as $R^{22}$, $R^{23}$, $R^{24}$, $R^{25}$, and $R^{26}$).

In a non-limiting embodiment of the pyridine bisimine ligand having Structure PBI II and/or PBI V, the pyridine bisimine ligand can have a structure wherein one, two, or three of $R^{12}$, $R^{16}$, $R^{22}$, and $R^{26}$ independently can be a halogen, a primary carbon group(s) or a secondary carbon group(s) and the remainder of $R^{12}$, $R^{16}$, $R^{22}$, and $R^{26}$ can be hydrogen; alternatively, one, two, or three of $R^{12}$, $R^{16}$, $R^{22}$, and $R^{26}$ independently can be a primary carbon group(s) or a secondary carbon group(s) and the remainder of $R^{12}$, $R^{16}$, $R^{22}$, $R^{22}$ and $R^{26}$ can be hydrogen; alternatively, one of $R^{12}$, $R^{16}$, $R^{22}$, and $R^{26}$ independently can be a tertiary carbon group(s), none, one, or two of $R^{12}$, $R^{16}$, $R^{22}$, and $R^{26}$ independently can be a halogen, a primary carbon group(s) or a secondary carbon group(s), and the remainder of $R^{12}$, $R^{16}$, $R^{22}$, and $R^{26}$ can be hydrogen; alternatively, one of $R^{12}$, $R^{16}$, $R^{22}$, and $R^{26}$ $R^{16}$, $R^{22}$, and $R^{26}$ independently can be a tertiary carbon group(s), none, one, or two of $R^{12}$, $R^{16}$, $R^{22}$, and $R^{26}$ independently can be a primary carbon group(s) or a secondary carbon group(s), and the remainder of $R^{12}$, $R^{16}$, $R^{22}$, and $R^{26}$ can be hydrogen; alternatively, two of $R^{12}$, $R^{16}$, $R^{22}$, $R^{26}$ independently can be a tertiary carbon group(s), none, or one of $R^{12}$, $R^{16}$, $R^{22}$, and $R^{26}$ independently can be a halogen, a primary carbon group(s), or a secondary carbon group(s), and the remainder of $R^{12}$, $R^{16}$, $R^{22}$, and $R^{26}$ can be hydrogen; alternatively, two of $R^{12}$, $R^{16}$, $R^{22}$, and $R^{26}$ independently can be a tertiary carbon group(s), none, or one of $R^{12}$, $R^{16}$, $R^{22}$, and $R^{26}$ independently can be a primary carbon group(s) or a secondary carbon group(s), and the remainder of $R^{12}$, $R^{16}$, $R^{22}$, and $R^{26}$ can be hydrogen; alternatively, one or two of $R^{12}$, $R^{16}$, $R^{22}$, and $R^{26}$ independently can be a tertiary carbon group(s) and the remainder of $R^{12}$, $R^{16}$, $R^{22}$, and $R^{26}$ can be hydrogen; alternatively, none or one of $R^{12}$, $R^{16}$, $R^{22}$, and $R^{26}$ can be a primary carbon group(s) or a secondary carbon group(s), one of $R^{12}$, $R^{16}$, $R^{22}$, and $R^{26}$ can be a tertiary carbon group, and the remainder of $R^{12}$, $R^{16}$, $R^{22}$, and $R^{26}$ can be hydrogen; alternatively, one of $R^{12}$, $R^{16}$, $R^{22}$, and $R^{26}$ can be a quaternary carbon group and the remainder of $R^{12}$, $R^{16}$, $R^{22}$, and $R^{26}$ can be hydrogen; alternatively, two of $R^{12}$, $R^{16}$, $R^{22}$, and $R^{26}$ can be a quaternary carbon group and the remainder of $R^{12}$, $R^{16}$, $R^{22}$, and $R^{26}$ can be hydrogen; or alternatively, one of $R^{12}$, $R^{16}$, $R^{22}$, and $R^{26}$ can be a quaternary carbon group and the remainder of $R^{12}$, $R^{16}$, $R^{22}$, and $R^{26}$ can be hydrogen.

In some non-limiting embodiments of the pyridine bisimine ligand having Structure PBI II and/or Structure PBI V, the pyridine bisimine ligand can have a structure wherein $R^{12}$ and $R^{22}$ independently can be a primary carbon group(s) or a secondary carbon group(s) and $R^{16}$ and $R^{26}$ can be hydrogen; alternatively, $R^{12}$ can be a primary carbon group, a secondary carbon group, or a tertiary group, $R^{22}$ can be a tertiary carbon group, and $R^{16}$ and $R^{26}$ can be hydrogen; alternatively, $R^{12}$ and $R^{22}$ independently can be a tertiary carbon group, and the remainder of $R^{16}$ and $R^{26}$ can be hydrogen; alternatively, $R^{12}$ and $R^{22}$ independently can be quaternary carbon groups, and $R^{16}$ and $R^{26}$ can be hydrogen; or alternatively, $R^{12}$ and $R^{22}$ independently can be halogens, and $R^{16}$ and $R^{26}$ can be hydrogen. In some non-limiting embodiments of the pyridine bisimine ligand having Structure PBI II and/or Structure PBI V, the pyridine bisimine ligand can have a structure wherein $R^{12}$ and $R^{22}$ independently can be trihalo primary group (e.g., trifluoromethane), and $R^{16}$ and $R^{26}$ can be hydrogen.

In some non-limiting embodiments of the pyridine bisimine ligand having Structure PBI II and/or Structure PBI V, the pyridine bisimine ligand can have a structure wherein $R^{12}$ can be a inert functional group, a primary carbon group, a secondary carbon group, or a tertiary carbon group and $R^{16}$, $R^{22}$, and $R^{26}$ independently can be hydrogen or a halide; $R^{12}$ can be a primary carbon group or a secondary carbon group, or a tertiary carbon group and $R^{16}$, $R^{22}$, and $R^{26}$ independently can be hydrogen or a halide; $R^{12}$ and $R^{16}$ can be an inert functional group(s), a primary carbon group(s), or secondary carbon group(s) and $R^{22}$ and $R^{26}$ independently can be hydrogen or a halide; alternatively, $R^{12}$ and $R^{16}$ can be a primary carbon group(s) or a secondary carbon group(s) and $R^{22}$, and $R^{26}$ independently can be hydrogen or a halide; alternatively, $R^{12}$ can be an inert functional group(s), a primary carbon group(s), or secondary carbon group(s), $R^{16}$ can be a tertiary group, and $R^{22}$ and $R^{26}$ independently can be hydrogen or a halide; alternatively, $R^{12}$ can be a primary carbon group or a secondary carbon group, $R^{16}$ can be a tertiary group, and $R^{22}$ and $R^{26}$ independently can be hydrogen or a halide; alternatively, $R^5$ and $R^{12}$ can form a ring, $R^{16}$ can be an inert functional group, a primary carbon group, or secondary carbon group, and $R^{22}$ and $R^{26}$ independently can be hydrogen or a halide; alternatively, $R^5$ and $R^{12}$ can form a ring, $R^{16}$ can be an a primary carbon group or secondary carbon group, and $R^{22}$ and $R^{26}$ independently can be hydrogen or a halide; or alternatively, $R^{12}$ and $R^{13}$ can form a ring, $R^{15}$ and $R^{16}$ can form a ring, and $R^{22}$ and $R^{26}$ independently can be hydrogen or a halide. In an embodiment, the $R^{12}$ group portion of the group forming a ring with $R^5$, the $R^{12}$ group portion of the group forming a ring with $R^{13}$, and/or the $R^{16}$ group portion of the group forming a ring with $R^{15}$ can be a primary carbon group, secondary carbon group, or tertiary carbon group; alternatively, a primary carbon group or a secondary carbon group; alternatively, a primary carbon group; alternatively, a secondary carbon group; or alternatively, tertiary carbon group.

Within any aspect or any embodiment wherein the pyridine bisimine ligand has Structure PBI II and/or PBI V and where $R^{12}$, $R^{16}$, $R^{22}$, and $R^{26}$ can have particular features, the remaining groups ($R^{13}$, $R^{14}$, $R^{15}$, $R^{23}$, $R^{24}$, and/or $R^{25}$) can be any group(s) or have any features described herein consistent with the features related to $R^{12}$, $R^{16}$, $R^{22}$, and $R^{26}$; or alternatively, the remaining groups ($R^{13}$, $R^{14}$, $R^{15}$, $R^{23}$, $R^{24}$, and/or $R^{25}$) can be hydrogen. Generally, the carbon groups (whether primary, secondary, tertiary, or quaternary) can be an organyl group; alternatively, an organyl group consisting essentially of inert functional groups; or alternatively, a hydrocarbyl group. Organyl groups, an organyl groups consisting essentially of inert functional groups, and hydrocarbyl groups are independently described herein and based upon the present disclosure one can appropriately classify a particular organyl group, an organyl group consisting essentially of inert functional groups, or hydrocarbyl group as a primary carbon group, secondary carbon group, tertiary carbon group, or quaternary carbon group.

In a non-limiting embodiment of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have a structure wherein $R^{2p}$ and $R^{5p}$ on each pyrrol-1-yl group independently can be hydrogen or any non-hydrogen group described herein. In some embodiments, the non-hydrogen group which can be utilized for any of each $R^{2p}$ and $R^{5p}$ independently can be an inert functional group, a primary carbon group, a secondary carbon group, a tertiary carbon group, or a quaternary carbon group; alternatively, a halogen, a primary carbon group, a secondary carbon group, a tertiary carbon group, or a quaternary carbon group; alternatively, primary carbon group, a secondary carbon group, a tertiary carbon group, or a quaternary carbon group; alternatively, a primary carbon group or a secondary carbon group; alternatively, and inert functional group; alternatively, a halogen; alternatively, a primary carbon group; alternatively, a secondary carbon group; alternatively, a tertiary carbon group; or alternatively, a quaternary carbon group.

In a non-limiting embodiment of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have a structure wherein at least one of $R^{2p}$, $R^{5p}$, $R^{12p}$, and $R^{15p}$ can be any non-hydrogen group described herein and the remainder of $R^{2p}$, $R^{5p}$, $R^{12p}$, and $R^{15p}$ can be hydrogen; alternatively, wherein one of $R^{2p}$, $R^{5p}$, $R^{12p}$, and $R^{15p}$ can be any non-hydrogen group described herein and the remainder of $R^{2p}$, $R^{5p}$, $R^{12p}$, and $R^{15p}$ can be hydrogen; alternatively, wherein two of $R^{2p}$, $R^{5p}$, $R^{12p}$, and $R^{15p}$ independently can be any non-hydrogen group described herein and the remainder of $R^{2p}$, $R^{5p}$, $R^{12p}$, and $R^{15p}$ can be hydrogen; or alternatively, wherein three of $R^{2p}$, $R^{5p}$, $R^{12p}$, and $R^{15p}$ independently can be any non-hydrogen group described herein and the remainder of $R^{2p}$, $R^{5p}$, $R^{12p}$, and $R^{15p}$ can be hydrogen. In another non-limiting embodiment of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have a structure wherein at least one of $R^{2p}$, $R^{5p}$, $R^{12p}$, and $R^{15p}$ can be any non-hydrogen group described herein, the remainder of $R^{2p}$, $R^{5p}$, $R^{12p}$, and $R^{15p}$ can be hydrogen, and $R^{3p}$, $R^{4p}$, $R^{13p}$, and $R^{14p}$ can be hydrogen; alternatively, wherein one of $R^{2p}$, $R^{5p}$, $R^{12p}$, and $R^{15p}$ can be any non-hydrogen group described herein, the remainder of $R^{2p}$, $R^{5p}$, $R^{12p}$, and $R^{15p}$ can be hydrogen, and $R^{3p}$, $R^{4p}$, $R^{13p}$, and $R^{14p}$ can be hydrogen; alternatively, two of $R^{2p}$, $R^{5p}$, $R^{12p}$, and $R^{15p}$ independently can be any non-hydrogen group described herein, the remainder of $R^{2p}$, $R^{5p}$, $R^{12p}$, and $R^{15p}$ can be hydrogen, and $R^{3p}$, $R^{4p}$, $R^{13p}$, and $R^{14p}$ can be hydrogen; or alternatively, three of $R^{2p}$, $R^{5p}$, $R^{12p}$, and $R^{15p}$ independently can be any non-hydrogen group described herein, the remainder of $R^{2p}$, and $R^{15p}$ can be hydrogen, and $R^{3p}$, $R^{4p}$, $R^{13p}$, and $R^{14p}$ can be hydrogen. In an embodiment of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have a structure wherein $R^{2p}$ and $R^{5p}$ are different from $R^{12p}$ and $R^{15p}$; or alternatively, wherein $R^{2p}$ and $R^{5p}$ are the same as $R^{12p}$ and $R^{15p}$. In some embodiments of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have a structure wherein $R^6$ (pyrrol-1-yl Structure P1) and $R^7$ (pyrrol-1-yl Structure P2) are different (i.e., $R^{2p}$, $R^{3p}$, $R^{4p}$, and $R^{5p}$ are not exactly the same as $R^{12p}$, $R^{13p}$, $R^{14p}$, and $R^{15p}$); or alternatively, wherein $R^6$ (pyrrol-1-yl Structure P1) and $R^7$ (pyrrol-1-yl Structure P2) are the same (i.e., $R^{2p}$, $R^{3p}$, $R^{4p}$, and $R^{5p}$ are exactly the same as $R^{12p}$, $R^{13p}$, $R^{14p}$, and $R^{15p}$). In some non-limiting embodiments of the pyridine bisimine ligand having Structure PBI I and/or Structure PBI IV where $R^6$ and $R^7$ are pyrrol-1-yl groups having Structure P1 and Structure P2 (respectively), the pyridine bisimine ligand can have any aspect or any embodiment of the pyridine bisimine ligand having Structure PBI II and/or Structure PBI V wherein $R^{2p}$, $R^{3p}$, $R^{4p}$, and $R^{5p}$ correspond to $R^{12}$, $R^{13}$, $R^{15}$, and $R^{16}$ (respectively) and $R^{12p}$, $R^{13p}$, $R^{14p}$, and $R^{15p}$ correspond to $R^{22}$, $R^{23}$, $R^{25}$, and $R^{26}$ (respectively).

In a non-limiting embodiment of the pyridine bisimine ligands having Structure BPBI III and/or Structure BPBI VI where L can have Structure 10L, Structure 12L, and/or Structure 14L, the pyridine bisimine ligand can have a structure where each pyridine bisimine moiety of the pyridine bisimine ligand independently can have a structure wherein $R^{12}$, $R^{16}$, $R^{83L}$, and $R^{85L}$ independently can be hydrogen or any non-hydrogen group described herein. In some embodiments, the non-hydrogen group which can be utilized for any of $R^{12}$, $R^{16}$, $R^{83L}$, and/or $R^{85L}$ can be an inert functional group, a primary carbon group, a secondary carbon group, a tertiary carbon group, or a quaternary carbon group; alternatively, a halogen, a primary carbon group, a secondary carbon group, a tertiary carbon group, or a quaternary carbon group; alternatively, primary carbon group, a secondary carbon group, a tertiary carbon group, or a quaternary carbon group; alternatively, a primary carbon group or a secondary carbon group; alternatively, and inert functional group; alternatively, a halogen; alternatively, a primary carbon group; alternatively, a secondary carbon group; alternatively, a tertiary carbon group; or alternatively, a quaternary carbon group.

In a non-limiting embodiment of the pyridine bisimine ligands having Structure BPBI III and/or Structure BPBI VI where L can have Structure 10L, Structure 12L, and/or Structure 14L, the pyridine bisimine ligand can have a structure where each pyridine bisimine moiety of the pyridine bisimine ligand independently can have a structure wherein at least one of $R^{12}$, $R^{16}$, $R^{83L}$, and $R^{85L}$, independently can be any non-hydrogen group described herein and the remainder of $R^{12}$, and $R^{16}$, $R^{83L}$, and $R^{85L}$ can be hydrogen; alternatively, wherein one of $R^{12}$, $R^{16}$, $R^{83L}$, and $R^{85L}$ can be any non-hydrogen group described herein and the remainder of $R^{12}$, $R^{16}$, $R^{83L}$, and $R^{85L}$ can be hydrogen; alternatively, wherein two of $R^{12}$, $R^{16}$, $R^{83L}$, and $R^{85L}$ independently can be any non-hydrogen group described herein and the remainder of $R^{12}$, $R^{16}$, $R^{83L}$, and $R^{85L}$ can be hydrogen; or alternatively, wherein three of $R^{12}$, $R^{83L}$, and $R^{85L}$ independently can be any non-hydrogen group described herein and the remainder of $R^{12}$, $R^{16}$, $R^{83L}$, and $R^{85L}$ can be hydrogen. In another non-limiting embodiment, of the pyridine bisimine ligands having Structure BPBI III and/or Structure BPBI VI where L can have Structure 10L, Structure 12L, and/or Structure 14L, the pyridine bisimine ligand can have a structure where each pyridine bisimine moiety of the pyridine bisimine ligand independently can have a structure wherein at least one of $R^{12}$, $R^{16}$, $R^{83L}$, and $R^{85L}$ independently can be any non-hydrogen group described herein, the remainder of $R^{12}$, $R^{16}$, $R^{83L}$, and $R^{85L}$ can be hydrogen, and $R^{13}$, $R^{14}$, $R^{15}$, $R^{82L}$ (if present), and $R^{86L}$ (if present) can be hydrogen; alternatively, wherein one of $R^{12}$, $R^{16}$, $R^{83L}$, and $R^{85L}$ can be any non-hydrogen group described herein, the remainder of $R^{12}$, $R^{16}$, $R^{83L}$, and $R^{85L}$ can be hydrogen, and $R^{13}$, $R^{14}$, $R^{15}$, $R^{82L}$ (if present), and $R^{86L}$ (if present) can be hydrogen; alternatively, two of $R^{12}$, $R^{16}$, $R^{83L}$, and $R^{85L}$ independently can be any non-hydrogen group described herein, the remainder of $R^{12}$, $R^{16}$, $R^{83L}$, and $R^{85L}$ can be hydrogen, and $R^{13}$, $R^{14}$, $R^{15}$, $R^{82L}$ (if present), and $R^{86L}$ (if present) can be hydrogen; or alternatively, three of $R^{12}$, $R^{16}$, $R^{83L}$, and $R^{85L}$ independently can be any non-hydrogen group described herein, the remainder of $R^{12}$, $R^{16}$, $R^{83L}$, and $R^{85L}$ can be hydrogen, and $R^{13}$, $R^{14}$, $R^{15}$, $R^{82L}$ (if present), and $R^{86L}$ (if present) can be hydrogen.

Generally, $R^{12}$, $R^{16}$, $R^{83L}$, and $R^{85L}$ around each of the two pyridine bisimine groups in the pyridine bisimine ligand having structure BPBI III are independent of each other. In an embodiment of the pyridine bisimine ligands having Structure BPBI III and/or Structure BPBI VI where L can have Structure 10L, Structure 12L, and/or Structure 14L, the pyridine bisimine ligand can have a structure where $R^{12}$, $R^{16}$, $R^{83L}$, and $R^{12}$, $R^{16}$, $R^{83L}$, and $R^{85L}$ of each pyridine bisimine moiety of the pyridine bisimine ligand can be the same; or alternatively, where $R^{12}$, $R^{16}$, $R^{83L}$, and $R^{85L}$ of each pyridine bisimine moiety of the pyridine bisimine ligand can be different. In some embodiments of the pyridine bisimine ligand having Structure BPBI III or Structure BPBI VI where L has Structure 10L, Structure 12L, or Structure 14L, the pyridine bisimine ligand can have a structure wherein $R^{12}$ and $R^{16}$ are the same as $R^{83L}$ and $R^{85L}$; or alternatively, wherein $R^{12}$ and $R^{16}$ are the different from $R^{83L}$ and $R^{85L}$. In some embodiments of the pyridine bisimine ligands having Structure BPBI III and/or Structure BPBI VI where L can have Structure 10L, Structure 12L, and/or Structure 14L, the pyridine bisimine ligand can have a structure where each pyridine bisimine moiety of the pyridine bisimine ligand can be the same; or alternatively, each pyridine bisimine moiety of the pyridine bisimine ligand can be different.

In an embodiment of the pyridine bisimine ligand Structure BPBI III and/or Structure BPBI VI where L can have Structure 10L, Structure 12L, and/or Structure 14L, the pyridine bisimine ligand can have a structure where each pyridine bisimine moiety of the pyridine bisimine ligand independently can have a structure wherein i) one of $R^{12}$, $R^{16}$, $R^{83L}$, and $R^{85L}$ can be a primary carbon group or a secondary carbon group, ii) none, one or two of the remainder of can be $R^{12}$, $R^{16}$, $R^{83L}$, and $R^{85L}$ can be a primary carbon group, a secondary carbon group, a tertiary carbon group, or a non-halogen inert functional group (or alternatively, a primary carbon group, a secondary carbon group, or a tertiary carbon group), and iii) the $R^{12}$, $R^{16}$, $R^{83L}$, and $R^{85L}$ groups not having a carbon group or an non-halogen inert functional group can be hydrogen or a halogen (alternatively, hydrogen or a fluorine; or alternatively, hydrogen); alternatively, wherein i) one of $R^{12}$, $R^{16}$, $R^{83L}$, and $R^{85L}$ can be a tertiary carbon group, ii) none, one or two of the remainder of can be $R^{12}$, $R^{16}$, $R^{83L}$, and $R^{85L}$ can be a primary carbon group, a secondary carbon group, a tertiary carbon group, or a non-halogen inert functional group (or alternatively, a primary carbon group, a secondary carbon group, or a tertiary carbon group), and iii) the $R^{12}$, $R^{16}$, $R^{83L}$, and $R^{85L}$ groups not having a carbon group or a non-halogen inert functional group can be hydrogen or a halogen (alternatively, hydrogen or a fluorine; or alternatively, hydrogen); alternatively, wherein i) one of $R^{12}$, $R^{16}$, $R^{83L}$, and $R^{85L}$ can be a quaternary carbon group, ii) none or one of the remainder of can be $R^{12}$, $R^{16}$, $R^{83L}$, and $R^{85L}$ can be a tertiary carbon group, a quaternary carbon group, or a non-halogen inert functional group (or alternatively, a tertiary carbon group or a quaternary carbon group), and iii) the $R^{12}$, $R^{16}$, $R^{83L}$, and $R^{85L}$ groups not having a carbon group can be hydrogen or a halogen (alternatively, hydrogen or a fluorine; or alternatively, hydrogen).

Within any embodiment wherein the pyridine bisimine ligand has Structure BPBI III and/or Structure BPBI VI where L can have Structure 10L, Structure 12L, and/or Structure 14L and where $R^{12}$, $R^{16}$, $R^{83L}$, and $R^{85L}$ can have particular features, the remaining pyridine bisimine ligand groups can be any group(s) or have any features described herein consistent with the features related to $R^{12}$, $R^{16}$, $R^{83L}$, and $R^{85L}$. Generally, the carbon groups (whether primary, secondary, tertiary, or quaternary) can be organyl group; alternatively, an organyl group consisting essentially of inert functional groups; or alternatively, a hydrocarbyl group. Organyl groups, organyl groups consisting essentially of inert functional groups, and hydrocarbyl groups are independently described herein and based upon the present disclosure one can appropriately classify a particular organyl group, an organyl group consisting essentially of inert functional groups, or hydrocarbyl group as a primary carbon group, secondary carbon group, tertiary carbon group, or quaternary carbon group. In some embodiments, the primary carbon group, the secondary carbon group, the tertiary carbon group, and/or the quaternary carbon group can be a primary hydrocarbon group, a secondary hydrocarbon group, a tertiary hydrocarbon group, and/or a quaternary hydrocarbon group, respectively.

In an embodiment, the pyridine bisimine ligand can have, either individually or in any combination, Structure 1, Structure 2, Structure 3, Structure 4, Structure 5, Structure 6, Structure 7, Structure 8, Structure 9, Structure 10, Structure 11, Structure 12, Structure 13, Structure 14, Structure 15, Structure 16, Structure 17, Structure 18, Structure 19, Structure 20, Structure 21, Structure 22, Structure 23, Structure 24, Structure 25, Structure 26, Structure 27, Structure 28, Structure 29, Structure 30, Structure 31, Structure 32, Structure 33, Structure 34, Structure 35, Structure 36, Structure 37, Structure 38, Structure 39, Structure 40, Structure 41, Structure 42, Structure 43, Structure 44, Structure 45, Structure 46, Structure 47, Structure 48, Structure 49, Structure 50, Structure 51, Structure 52, Structure 53, Structure 54, Structure 55, Structure 56, Structure 57, Structure 58, Structure 59, Structure 60, Structure 61, Structure 62, Structure 63, Structure 64, or Structure 65.

Structure 1
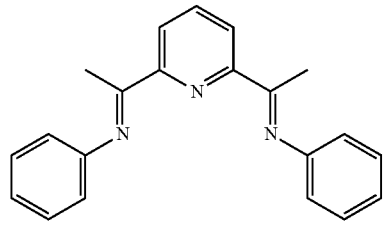

Structure 2
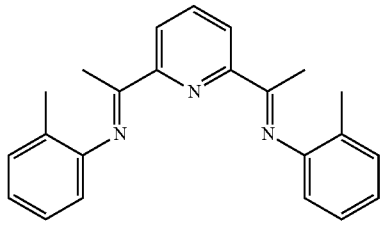

Structure 3
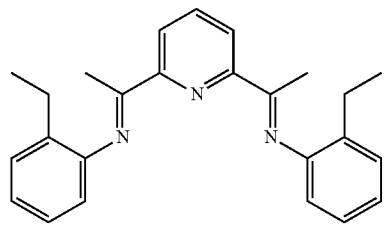

Structure 4
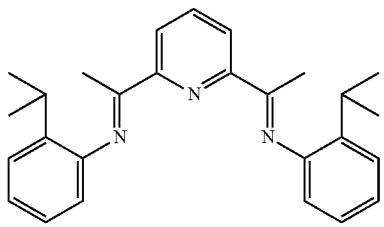

Structure 5
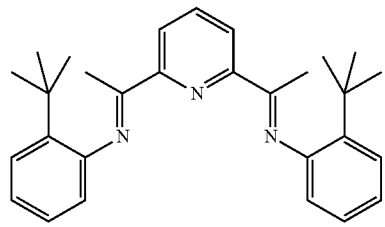

Structure 6
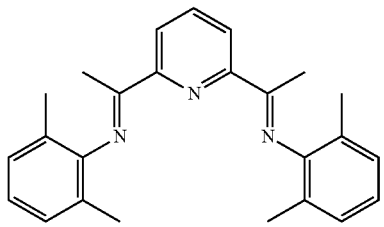

Structure 7
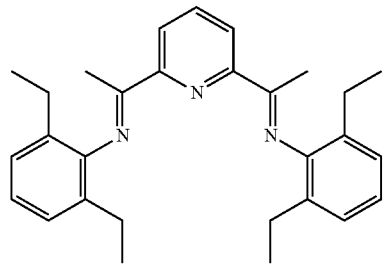

Structure 8
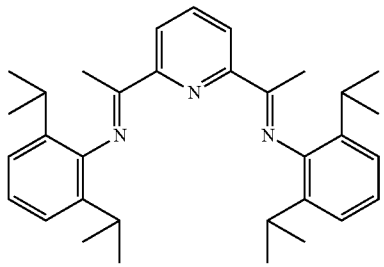

Structure 9
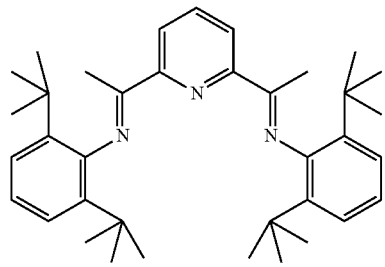

Structure 10
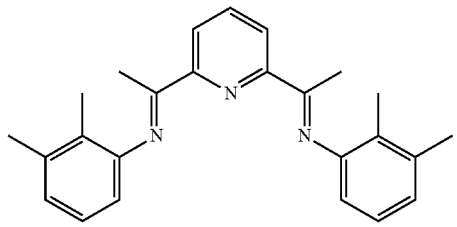

-continued
Structure 11
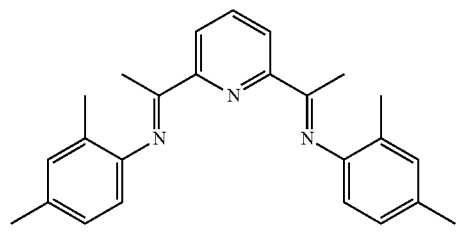
Structure 12
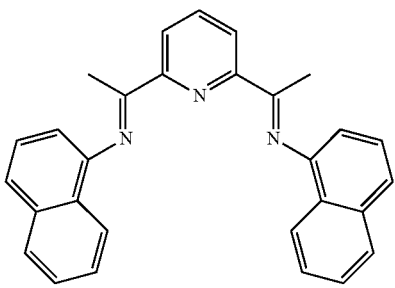
Structure 13
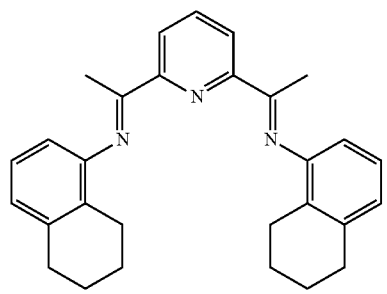
Structure 14
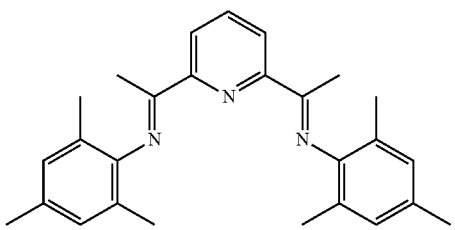
Structure 15
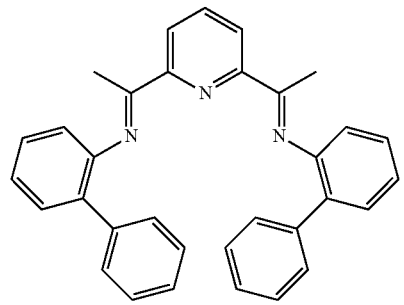
Structure 16
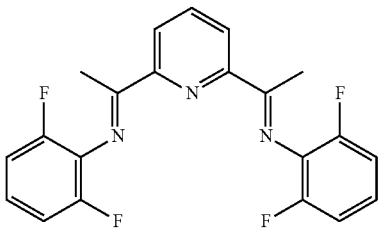
Structure 17
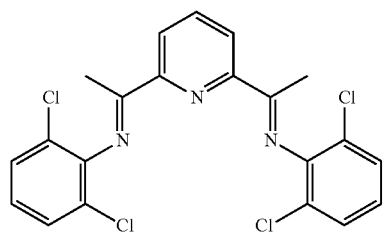
Structure 18
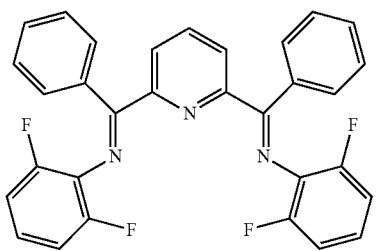
Structure 19
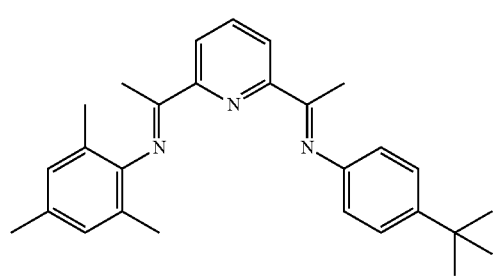
Structure 20
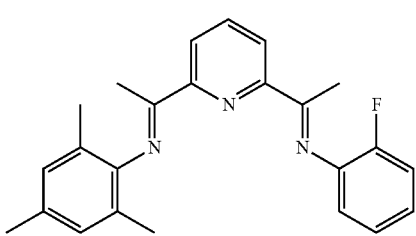

-continued
Structure 21
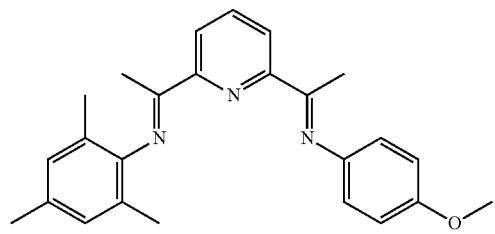
Structure 22
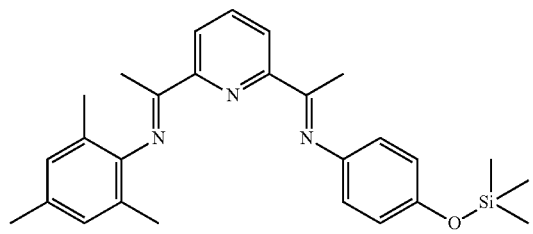
Structure 23
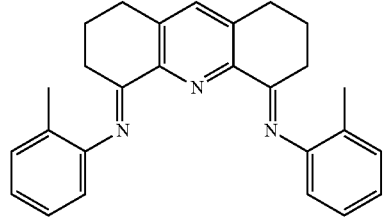
Structure 24
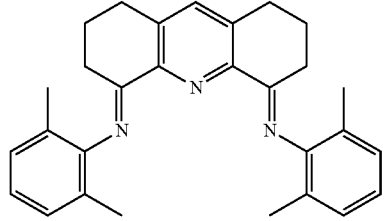
Structure 25
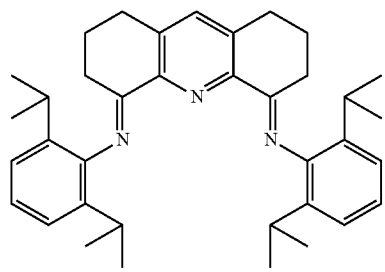
Structure 26
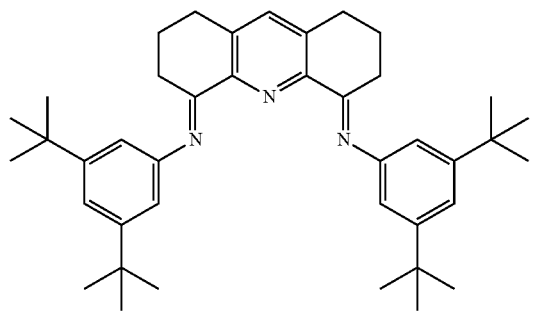
Structure 27
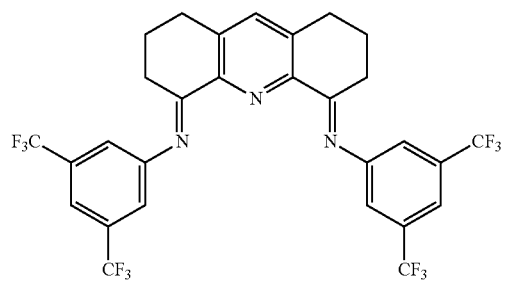
Structure 28
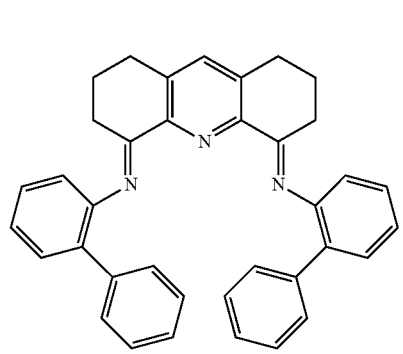
Structure 29
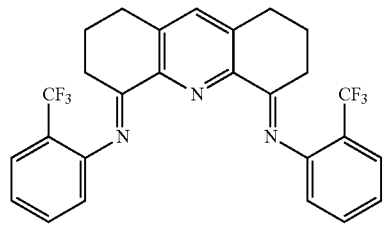
Structure 30
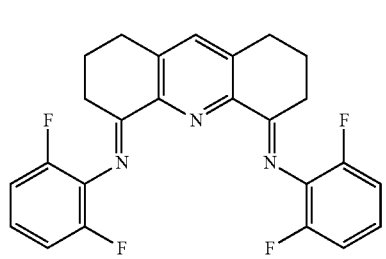

-continued
Structure 31
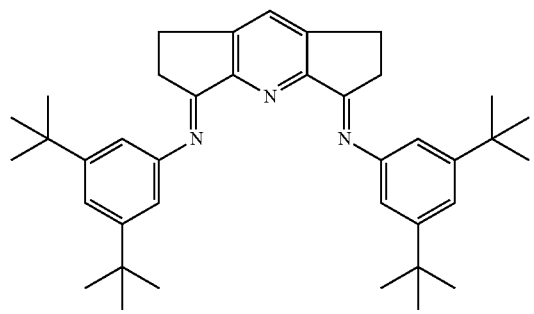
Structure 32
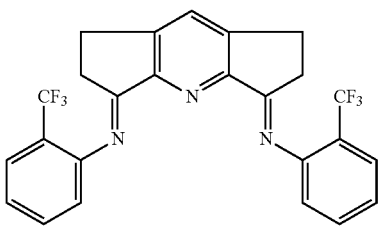
Structure 33
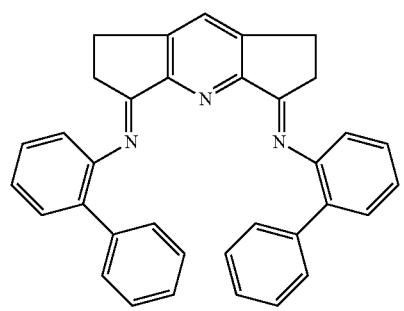
Structure 34
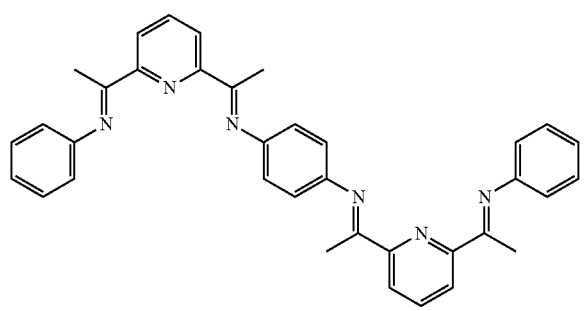
Structure 35
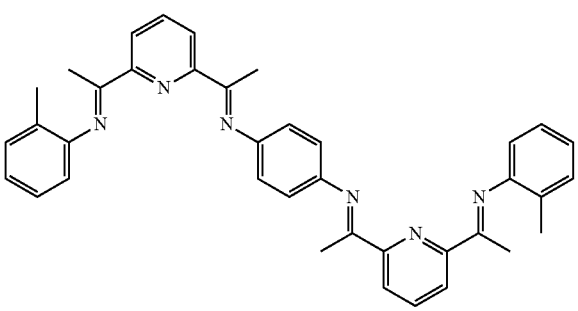
Structure 36
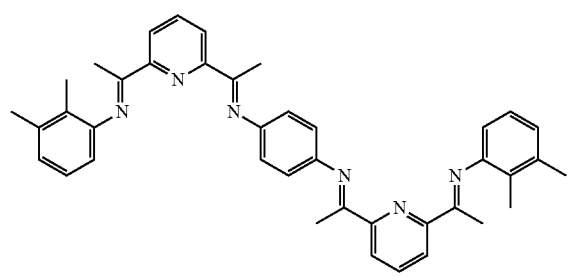
Structure 37
Structure 38
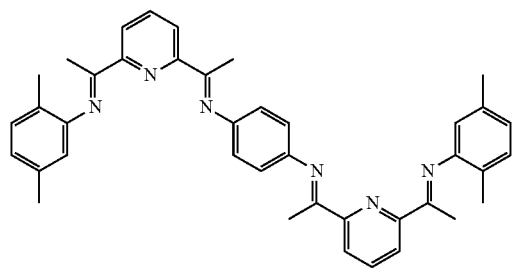
Structure 39
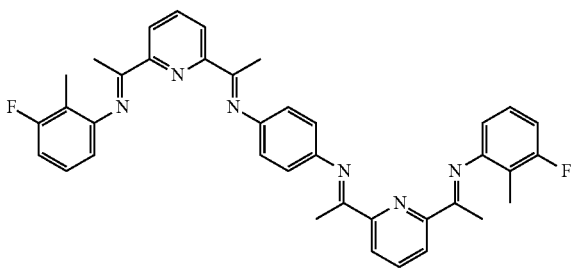

Structure 40
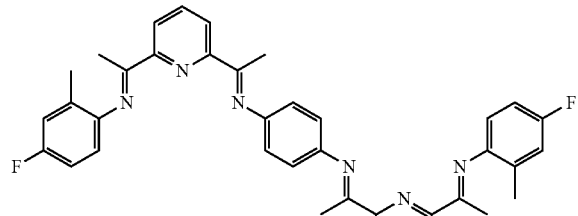
Structure 41
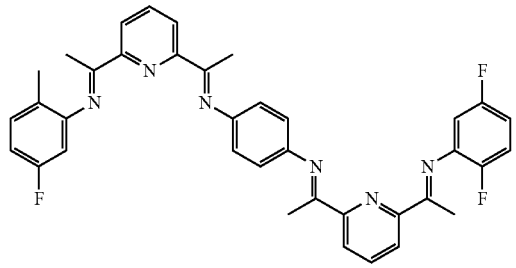
Structure 42
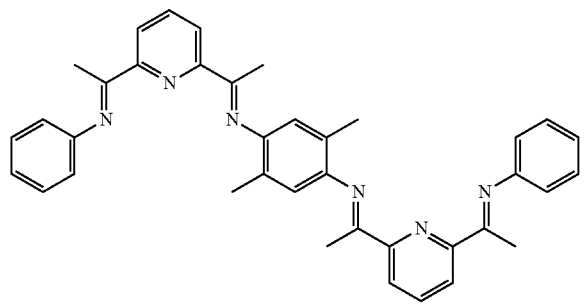
Structure 43
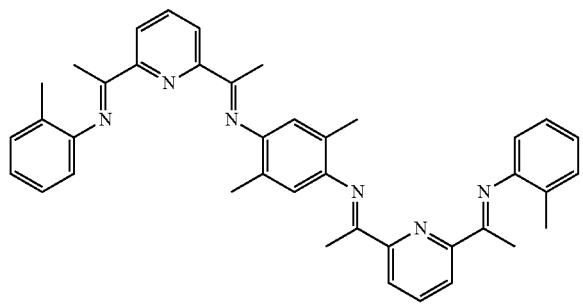
Structure 44
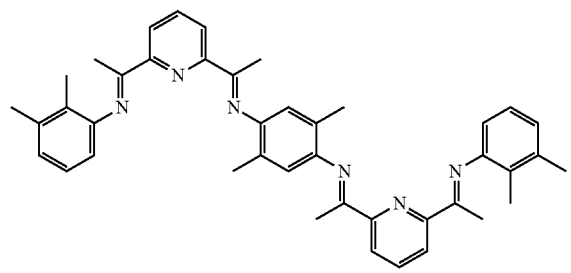
Structure 45
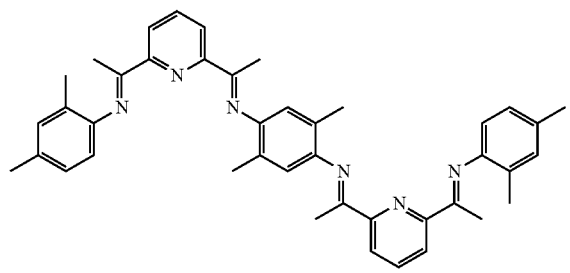
Structure 46
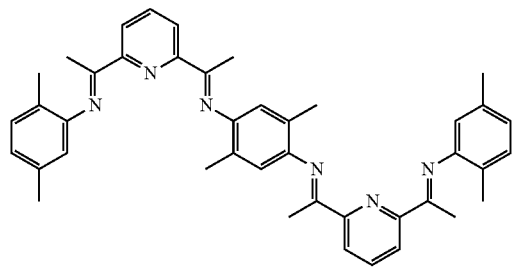
Structure 47
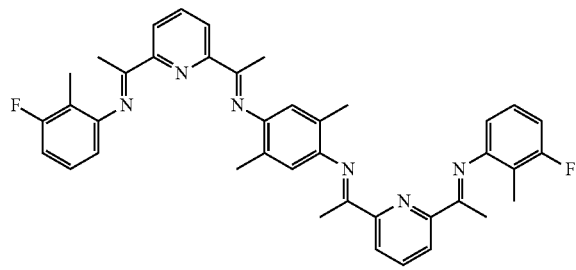
Structure 48
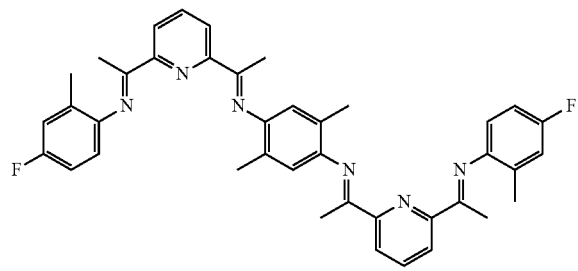
Structure 49
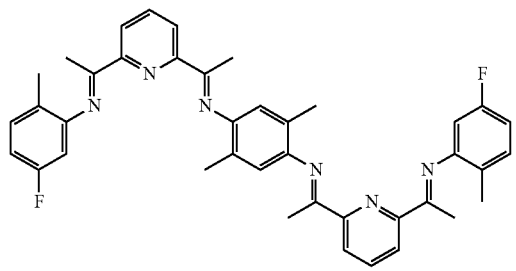

-continued
Structure 50
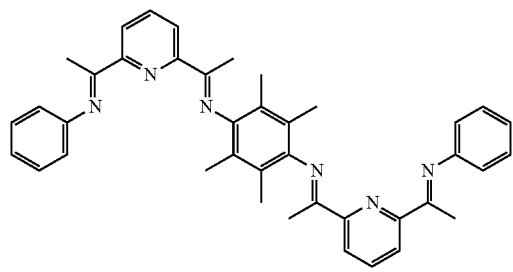
Structure 51
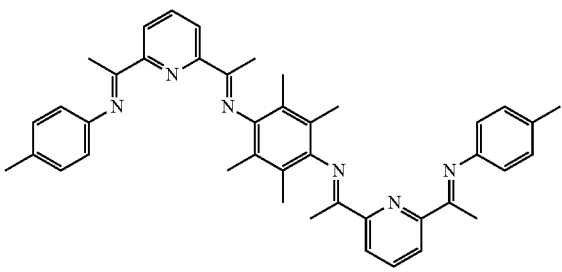
Structure 52
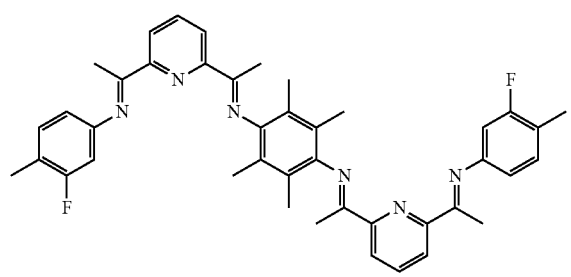
Structure 53
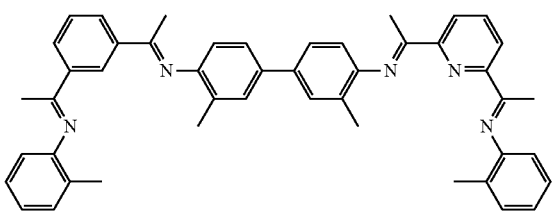
Structure 54
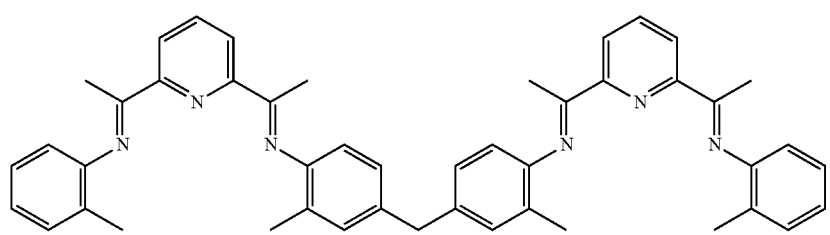
Structure 55
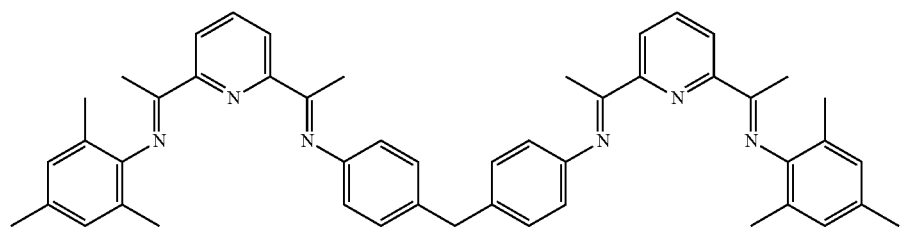
Structure 56
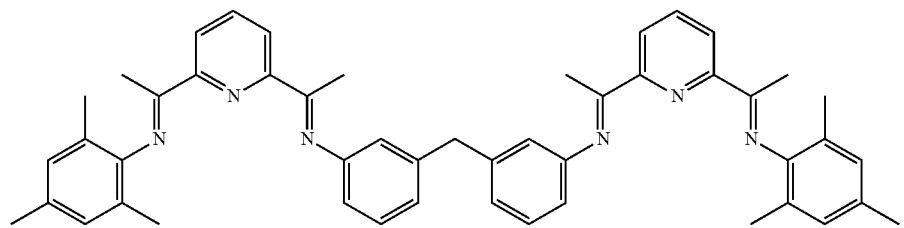
Structure 57
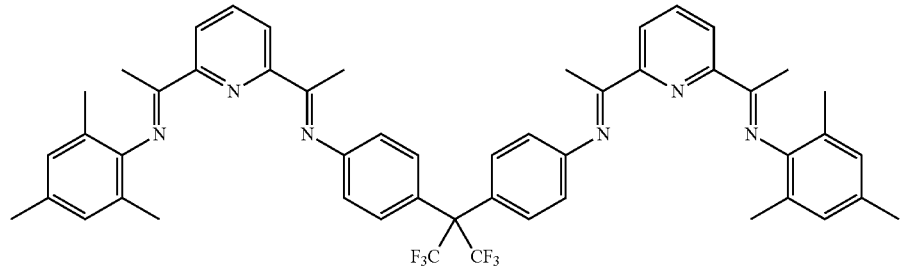

-continued
Structure 58
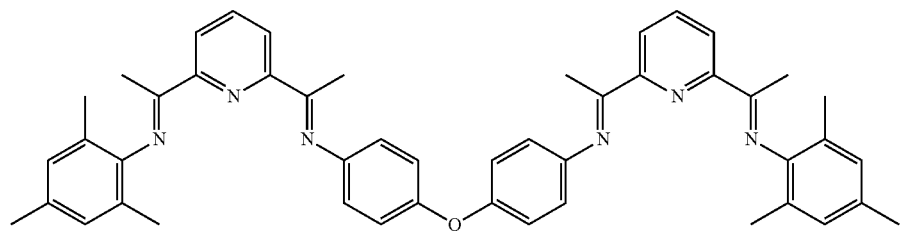
Structure 59
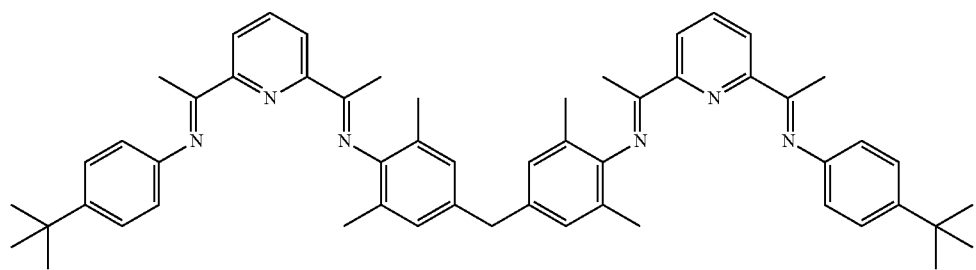
Structure 60
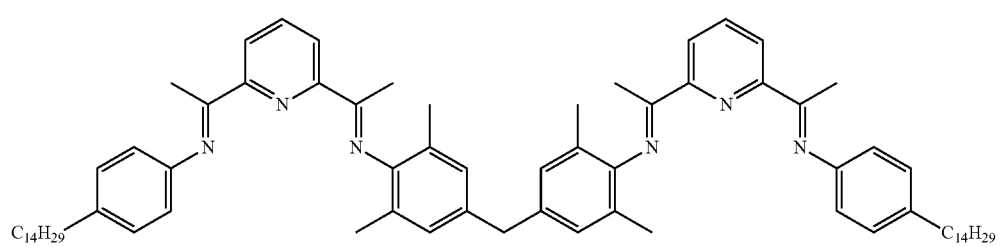
Structure 61
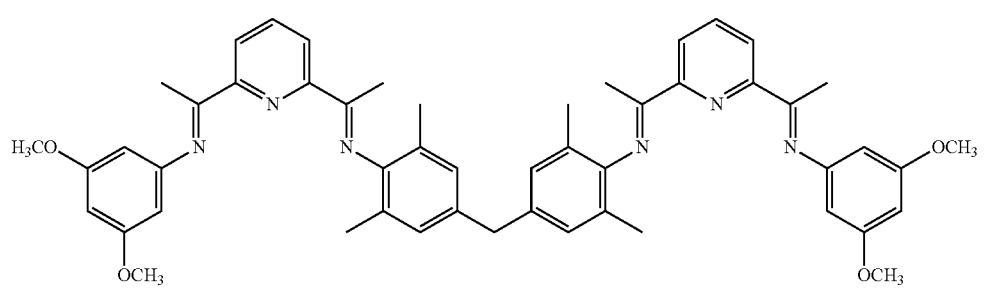
Structure 62
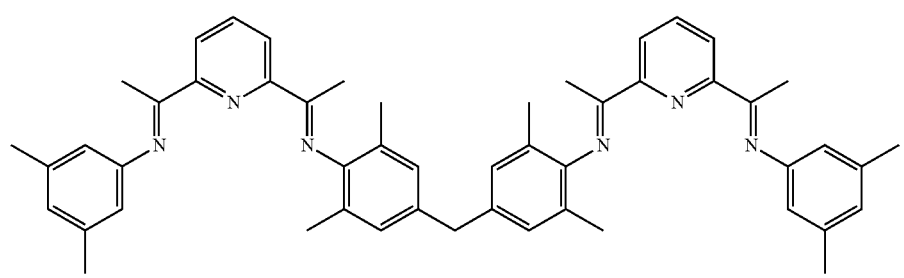
Structure 63
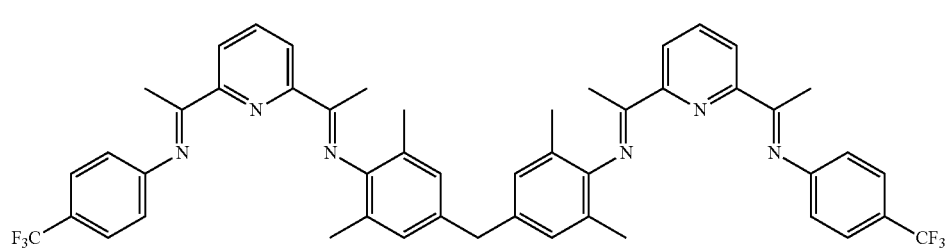

Structure 64

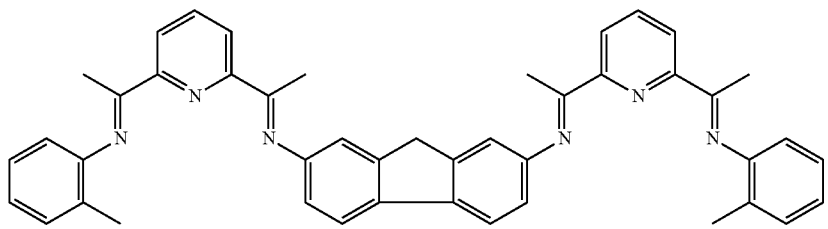

Structure 65

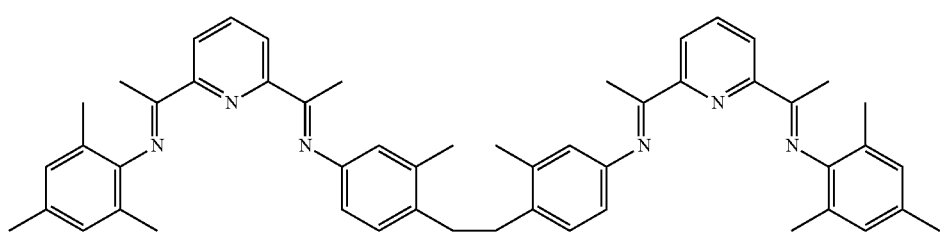

Generally, the metal compound of the metal compound complexed to a ligand (or any metal complex depicted herein) can be, comprise, or consist essentially of a metal compound having the formula $MX_n$. Within the formula of the metal compound having the formula $MX_n$, M represent the metal atom, X represents an anionic specie, and n represent the number of anionic species (or the metal oxidation state). Generally, the metal, M, and the anionic ligand, X, and the number of anionic species (or the metal oxidation state), n, are independent elements of the metal compound and are independently describe herein. The metal compound having the formula $MX_n$ can be described utilizing any aspect or embodiment of the metal atom described herein, any aspect or embodiment of the anionic specie described herein, and any aspect or embodiment of the number of anionic species (or metal atom oxidation state) described herein.

In an aspect, the metal compound can be complexed to a ligand comprising a pyridine bisimine group (a pyridine bisimine ligand or pyridine bisimine compound). In some embodiments, the metal compound can be complexed to a pyridine bisimine ligand comprising only one pyridine bisimine group; or alternatively, a pyridine bisimine ligand comprising only two pyridine bisimine groups. In an embodiment, a metal compound complexed to a ligand can be, comprise, or consist essentially of, Structure MPBI I, Structure MPBI II, Structure MPBI III, Structure BMPBI I, or Structure BMPBI III; alternatively, Structure MPBI I, Structure MPBI II, or Structure MPBI III; alternatively, Structure BMPBI I or Structure BMPBI III; alternatively, Structure MPBI I; alternatively, Structure MPBI II; alternatively, Structure MPBI III; alternatively, Structure BMPBI I; or alternatively, Structure BMPBI III. In other non-limiting embodiments, the metal compound complexed to a ligand can be, comprise, or consist essentially of, Structure MPBI IV, Structure MPBI V, Structure MPBI VI, Structure BMPBI IV, or Structure BMPBI VI; alternatively, Structure MPBI IV, Structure MPBI V, or Structure MPBI VI; alternatively, Structure BMPBI IV or Structure BMPBI VI; alternatively, Structure MPBI V or Structure MPBI VI; alternatively, Structure MPBI IV; alternatively, Structure MPBI V; alternatively, Structure MPBI VI; alternatively, Structure BMPBI IV; or alternatively, Structure BMPBI VI.

Structure MPBI I

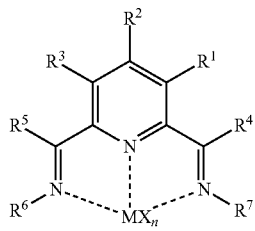

Structure MPBI II

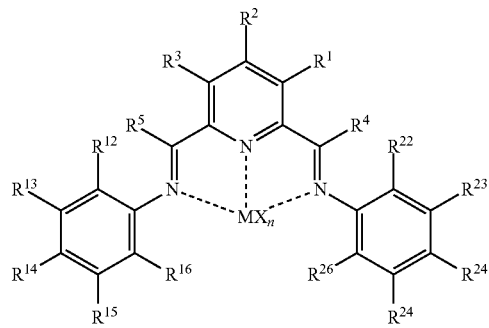

-continued
Structure MPBI III
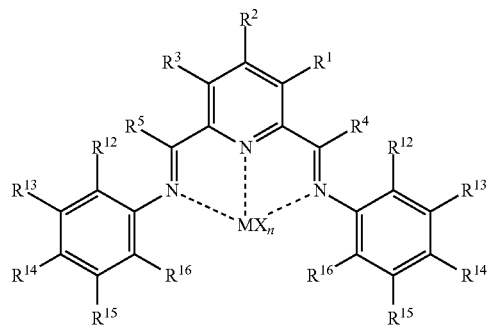
Structure BMPBI I
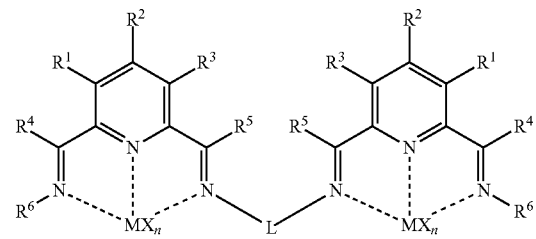
Structure BMPBI III
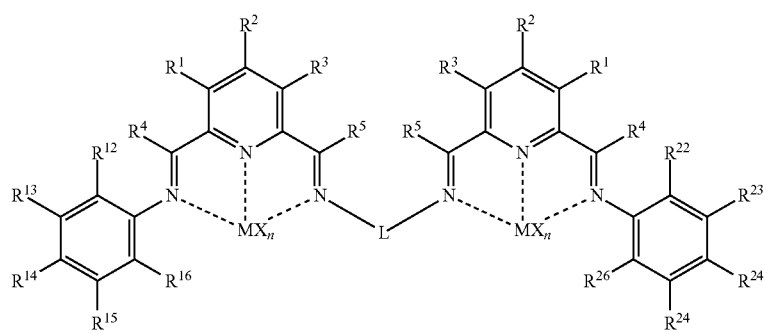
Structure MPBI IV
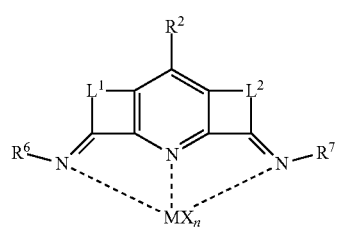
Structure MPBI V
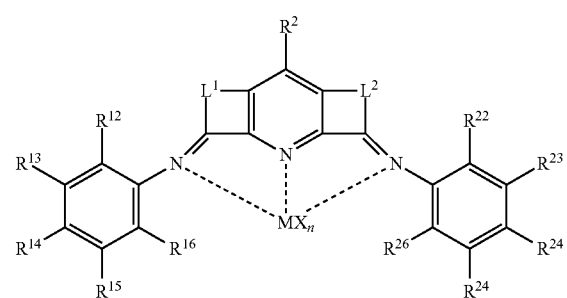
Structure MPBI VI
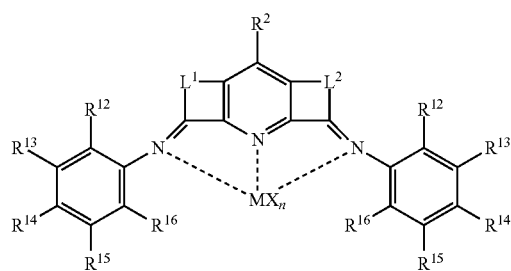
Structure BMPBI IV
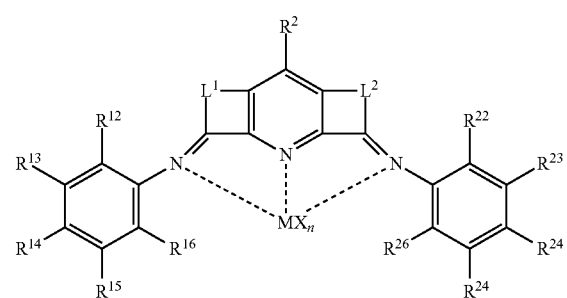
Structure BMPBI VI
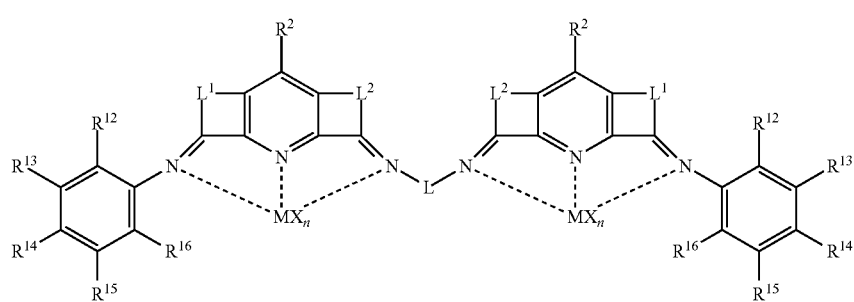

Generally, $R^1$, $R^2$, $R^3$, $R^4$, $R^5$, $R^6$, $R^7$, $R^{12}$, $R^{13}$, $R^{14}$, $R^{15}$, $R^{16}$, $R^{22}$, $R^{23}$, $R^{24}$, $R^{25}$, $R^{26}$, L, $L^1$, $L^2$, $MX_n$ are independent elements of their respective metal complexes having Structure MPBI I, Structure MPBI II, Structure MPBI III, Structure MPBI IV, Structure MPBI V, Structure MPBI VI, Structure BMPBI I, Structure BMPBI II, Structure BMPBI IV, and Structure BMPBI VI. The metal complexes having Structure MPBI I, Structure MPBI II, Structure MPBI III, Structure MPBI IV, Structure MPBI V, Structure MPBI VI, Structure BMPBI I, Structure BMPBI III, Structure BMPBI IV, and Structure BMPBI VI can be described utilizing any aspect or embodiment of $R^1$, $R^2$, $R^3$, $R^4$, $R^5$, $R^6$, $R^7$, $R^{12}$, $R^{13}$, $R^{14}$, $R^{15}$, $R^{16}$, $R^{22}$, $R^{23}$, $R^{24}$, $R^{25}$, and $R^{26}$ described herein, any aspect or embodiment of L described herein, any aspect or embodiment of L' described herein, any aspect or embodiment of $L^2$ described herein, and any aspect or embodiment of the metal compound $MX_n$ described herein (including any aspect or embodiment of M described herein, any aspect or embodiment of X described herein, and any aspect or embodiment of n described herein) when present in the metal compound complexed to a pyridine bisimine ligand. Other depictions of $MX_n$ complexed to a ligand can be prepared (and are readily apparent) by showing the ligation bonds of $MX_n$ to any ligand provided herein in a manner similar to the depictions of the metal compound, $MX_n$, complexed to respective general ligand depicted herein. These depictions can have the structure designation MPBI Q1, BMPBI Q2, or Y where Q1, Q2, and Y represent the ligand designation of the ligand having Structure PBI Q1, Structure BPBI Q2, or Structure Y, respectively. Further depictions of $MX_n$ complexed to a ligand can be prepared (and are readily apparent) by replacing $MX_n$ with any metal compound provided herein and/or showing the ligation bonds of metal compound to any ligand provided herein in a manner similar to the depictions of the metal compound, $MX_n$, complexed to respective general ligand depicted herein. These depictions can have the structure designation $MX_n$PBI Q1, $BMX_n$PBI Q2, or Structure $MX_n$Y where $MX_n$ represents the specific metal compound, and Q1, Q2, and Y represent the ligand designation of the ligand having Structure PBI Q1, Structure BPBI Q2, or Structure Y, respectively, or any other ligand provided herein.

It should be noted that the general metal complex structures depicted herein can further comprise a neutral ligand (also referred to a neutral Lewis base) other than the pyridine bisimine ligand. While the non-pyridine bisimine neutral ligand for the metal complex structures is not shown, it should be understood that the metal complex structure depiction without the non-pyridine bisimine neutral ligand does not limit the metal complexes to those not having a non-pyridine bisimine neutral ligand. In fact the metal complex structures which can be utilized in any aspect disclosed herein and any embodiment disclosed herein can include a non-pyridine bisimine neutral ligand and that these depictions provided herein do not limit metal complexes to those which do not comprise a non-pyridine bisimine neutral ligand regardless of the language utilized to describe the metal complexes. In an aspect, the non-pyridine bisimine neutral ligand can be, comprise, or consist essentially of, an ether, amine, a sulfide, a nitrile, or any combination thereof; alternatively, an ether; alternatively, an amine; alternatively, a sulfide; or alternatively, a nitrile.

In an embodiment, the ether which can be utilized as the non-pyridine bisimine neutral ligand can be a $C_2$ to $C_{30}$ ether; alternatively, a $C_2$ to $C_{20}$ ether; alternatively, a $C_2$ to $C_{10}$ ether; or alternatively, a $C_2$ to $C_5$ ether. In some embodiments, the ether which can be utilized as the non-pyridine bisimine neutral ligand can be a dihydrocarbyl ether. Hydrocarbyl groups (general and specific) are disclosed herein (e.g., as substituent groups, among other places) and can be utilized without limitation to further describe the dihydrocarbyl ethers which can be utilized as the non-pyridine bisimine neutral ligand. Generally, each hydrocarbyl group of the dihydrocarbyl ether is independent of each other and can be the same: or alternatively, can be different. In some embodiments, the two hydrocarbyl group can be joined to form a cyclic ether wherein the ether oxygen atom is part of a ring or ring system. In a non-limiting embodiment, the ether which can be utilized a the non-pyridine bisimine neutral ligand can be, comprise, or consist essentially of, dimethyl ether, diethyl ether, dipropyl ether, dibutyl ether, methyl ethyl ether, methyl propyl ether, methyl butyl ether, tetrahydrofuran, or any combination thereof; or alternatively, dimethyl ether, diethyl ether, dipropyl ether, dibutyl ether, methyl ethyl ether, methyl propyl ether, methyl butyl ether, or any combination thereof. In another non-limiting embodiment, the ether which can be utilized a the non-pyridine bisimine neutral ligand can be, comprise, or consist essentially of, dimethyl ether; alternatively, diethyl ether; alternatively, dipropyl ether; alternatively, dibutyl ether; alternatively, methyl ethyl ether; alternatively, methyl propyl ether; alternatively, methyl butyl ether; or alternatively, tetrahydrofuran.

In an embodiment, the amine which can be which can be utilized as the non-pyridine bisimine neutral ligand can be, comprise, or consist essentially of, a monohydrocarbylamine, a dihydrocarbylamine, or a trihydrocarbylamine, or any combination thereof; alternatively, monohydrocarbylamine; alternatively, a dihydrocarbylamine; or alternatively, a trihydrocarbylamine. Monohydrocarbylamines which can be utilized as the non-pyridine bisimine neutral ligand can be a $C_1$ to $C_{30}$ monohydrocarbylamine; alternatively, a $C_1$ to $C_{20}$ monohydrocarbylamine; alternatively, a $C_1$ to $C_{10}$ monohydrocarbylamine; or alternatively, a $C_1$ to $C_5$ monohydrocarbylamine. Dihydrocarbylamines which can be utilized as the non-pyridine bisimine neutral ligand can be have the same number of carbon atoms as the monohydrocarbylamines with the exception that the lowest carbon number dihydrocarbylamine is $C_2$. Trihydrocarbylamines which can be utilized as the non-pyridine bisimine neutral ligand can be have the same number of carbon atoms as the monohydrocarbylamines with the exception that the lowest carbon number dihydrocarbylamine is $C_2$. Hydrocarbyl groups (general and specific) are disclosed herein (e.g., as substituent groups, among other places) and can be utilized without limitation to further describe the monohydrocarbylamines, dihydrocarbylamines, and/or trihydrocarbylamines which can be utilized as the non-pyridine bisimine neutral ligand. Generally, each hydrocarbyl group of the dihydrocarbylamine (and trihydrocarbylamines) is independent of each other and can be the same: or alternatively, can be different. In a non-limiting embodiment, the monohydrocarbylamine, which can be utilized as the non-pyridine bisimine neutral ligand can be, comprise, or consist essentially of, methyl amine, ethyl amine, propyl amine, butyl amine, or any combination thereof; alternatively, methyl amine; alternatively, ethyl amine; alternatively, propyl amine; or alternatively, butyl amine. In some embodiments, the dihydrocarbylamine, which can be utilized as the non-pyridine bisimine neutral ligand can be, comprise, or consist essentially of, dimethyl amine, diethyl amine, dipropyl amine, dibutylamine, or any combination thereof; alternatively, dimethyl amine; alternatively, diethyl amine; alternatively, dipropyl amine; or alternatively, dibutylamine. In some embodiments, the trihydrocarbylamine, which can be utilized as the non-pyridine bisimine neutral ligand can be, comprise, or consist essentially of, trimethyl amine, triethyl amine, tripropyl amine, tributyl amine, or any combination thereof; alternatively, trimethyl amine; alternatively, triethyl amine; alternatively, tripropyl amine; or alternatively, tributyl amine.

In an embodiment, the thioether which can be utilized as the non-pyridine bisimine neutral ligand can be a $C_2$ to $C_{30}$ thioether; alternatively, a $C_2$ to $C_{20}$ thioether; alternatively, a $C_2$ to $C_{10}$ thioether; or alternatively, a $C_2$ to $C_5$ thioether. In some embodiments, the thioether which can be utilized as the non-pyridine bisimine neutral ligand can be a dihydrocarbyl thioether. Hydrocarbyl groups (general and specific) are disclosed herein (e.g., as substituent groups, among other places) and can be utilized without limitation to further describe the dihydrocarbyl thioethers which can be utilized as the non-pyridine bisimine neutral ligand. Generally, each hydrocarbyl group of the dihydrocarbyl thioether is independent of each other and can be the same: or alternatively, can be different. In some embodiments, the two hydrocarbyl group can be joined to form a cyclic thioether wherein the thioether sulfur atom is part of a ring or ring system. In a non-limiting embodiment, the thioether, which can be utilized as the non-pyridine bisimine neutral ligand can be, comprise, or consist essentially of, dimethyl thioether, diethyl thioether, dipropyl thioether, dibutyl thioether, methyl ethyl thioether, methyl propyl thioether, methyl butyl thioether, tetrahydrothiophene, thiane, or any combination thereof; alternatively, dimethyl thioether, diethyl thioether, dipropyl thioether, dibutyl thioether, methyl ethyl thioether, methyl propyl thioether, methyl butyl thioether, or any combination thereof; alternatively, tetrahydrothiophene, thiane, or any combination thereof. In another non-limiting embodiment, the thioether, which can be utilized as the non-pyridine bisimine neutral ligand can be, comprise, or consist essentially of, dimethyl thioether; alternatively, diethyl thioether; alternatively, dipropyl thioether; alternatively, dibutyl thioether; alternatively, methyl ethyl thioether; alternatively, methyl propyl thioether; alternatively, methyl butyl thioether; alternatively, tetrahydrothiophene; or alternatively, thiane.

In an embodiment, the nitrile which can be utilized as the neutral ligand can be a $C_2$ to $C_{30}$ nitrile; alternatively, a $C_2$ to $C_{20}$ nitrile; alternatively, a $C_2$ to $C_{10}$ nitrile; or alternatively, a $C_2$ to $C_5$ nitrile. In a non-limiting embodiment, the nitrile can be, comprise, or consist essentially of, acetonitrile, propionitrile, butyronitrile, benzonitrile, or any combination thereof; alternatively, acetonitrile; alternatively, propionitrile; alternatively, butyronitrile; or alternatively, benzonitrile.

In an embodiment, the metal, M, of the metal compound (or the metal complex), can be, comprise, or consist essentially of, a transition metal. In some embodiments, the metal, M, of the metal compound (or the metal complex) can be, comprise, or consist essentially of, a Group 5-10 metal, alternatively, a group 8-10 metal; alternatively, a Group 8-9 metal; alternatively, a Group 5 metal; alternatively, a Group 6 metal; alternatively, a Group 7 metal; alternatively, a Group 8 metal; alternatively, a Group 9 metal; or alternatively, a Group 10 metal. In other embodiments, the metal, M, of the metal compound (or the metal complex) can be, comprise, or consist essentially of, vanadium, chromium, iron, cobalt, or any combination thereof; alternatively, cobalt, iron, or any combination thereof; alternatively, vanadium; alternatively, chromium; alternatively, iron; or alternatively, cobalt.

In an embodiment, the oxidation state of the metal, M, of the metal compound (or the metal complex) can be +1, +2 or +3; alternatively, +2 or +3; alternatively, +1; alternatively, +2; or alternatively, +3. In an embodiment, n of the metal compound $MX_n$ can be the oxidation state of the metal, M. Consequently, the number of anionic ligands, X, can be 1, 2 or 3; alternatively, 2 or 3; alternatively, 1; alternatively, 2; or alternatively, 3. In should be noted that in some nomenclatures, when referring to a metal compound, the oxidation state of the metal (general or specific) in the metal compound can be indicated by placing the Roman Numeral of the oxidation state in parentheses after the name of the metal; for example iron(III) chloride and iron(II) chloride represent the chloride compounds of iron in the +3 and +2 oxidation states, respectively.

In an embodiment, the anionic specie of the metal compound (or the metal complex) can be any anion. In an embodiment, the anionic specie of the metal compound (or the metal complex) can be inorganic or organic; alternatively, inorganic; or alternatively, organic. Independently, the anionic specie of the metal compound (or the metal complex) can be a mono-anionic specie.

In an embodiment, each anionic specie of the metal compound (or the metal complex) independently can be a halide, a nitrate, a sulfate, a phosphate, a halate, a hydrocarboxide, a carboxylate, or a β-dionate (e.g., acetylacetonate); alternatively, a halide, a nitrate, a sulfate, a phosphate, or a halate; alternatively, a hydrocarboxide, a carboxylate, or a β-dionate (e.g., acetylacetonate); alternatively, a halide; alternatively, a nitrate; alternatively, a sulfate; alternatively, a phosphate; alternatively, a halate; alternatively, a hydrocarboxide; alternatively, a carboxylate; or alternatively, or a β-dionate (e.g., acetylacetonate). In an embodiment, each halide which can be utilized as the anionic species of the metal compound (or the metal complex) independently can be fluoride, chloride, bromide, or iodide; alternatively, chloride, bromide, or iodide; alternatively, chloride or bromide; alternatively, fluoride; alternatively, chloride: alternatively, bromide; or alternatively, iodide. In an embodiment, each halate which can be utilized as the anionic species of the metal compound (or the metal complex) independently can be fluorate, chlorate, bromate, or iodate; alternatively, fluorate; alternatively, chlorate; alternatively, bromate; or alternatively, iodate.

In an embodiment, each hydrocarboxide which can be utilized as the anionic species of the metal compound (or the metal complex) independently can be a $C_1$ to $C_{20}$ hydrocarboxide; alternatively, a $C_1$ to $C_{15}$ hydrocarboxide; or alternatively, a $C_1$ to $C_{10}$ hydrocarboxide. In an embodiment, each hydrocarboxide which can be utilized as the anionic species of the metal compound (or the metal complex) independently can be an alkoxide, a cycloalkoxide, an aroxide, or an aralkoxide; alternatively, an alkoxide; alternatively, a cycloalkoxide; alternatively, an aroxide; or alternatively, an aralkoxide.

Generally, each alkoxide which can be utilized as the anionic species of the metal compound (or the metal complex) independently can have the same number of carbon atoms as the hydrocarboxide which can be utilized as the anionic specie(s). In an embodiment, each alkoxide which can be utilized as the anionic species of the metal compound (or the metal complex) independently can be methoxide, ethoxide, a propoxide, a butoxide, a pentoxide, a hexoxide, a heptoxide, an octaoxide, a nonoxide, or a decoxide; alternatively, methoxide, ethoxide, a propoxide, a butoxide or a pentoxide; alternatively, methoxide; alternatively, an ethoxide; alternatively, a propoxide; alternatively, a butoxide; alternatively, a pentoxide; alternatively, a hexoxide; alternatively, a heptoxide; alternatively, an octaoxide; alternatively, a nonoxide; or alternatively, a decoxide. In an embodiment, each cycloalkoxide which can be utilized as the anionic species of the metal compound (or the metal complex) independently can be a $C_4$ to $C_{20}$ cycloalkoxide; alternatively, a $C_5$ to $C_{15}$, cycloalkoxide; or alternatively, a $C_6$ to $C_{10}$ cycloalkoxide. In an embodiment, each cycloalkoxide which can be utilized as the anionic species independently can be cyclopentoxide, a substituted cyclopentoxide, cyclohexoxide, or a substituted cyclohexide; alternatively, cyclopentoxide or a substituted cyclopentoxide; alternatively, cyclohexoxide or a substituted cyclohexoxide; alternatively, cyclopentoxide or cyclohexoxide; alternatively, cyclopentoxide; or alternatively, cyclohexoxide. In an embodiment, each aroxide which can be utilized as the anionic species of the metal compound (or the metal complex) independently can be a $C_6$ to $C_{20}$ aroxide; alternatively, a $C_6$ to $C_{15}$, aroxide; or alternatively, a $C_6$ to $C_{10}$ aroxide. In an embodiment, each aroxide which can be utilized as the anionic species of the metal compound (or the metal complex) independently can be phenoxide or a substituted phenoxide; or alternatively, a phenoxide. In an embodiment, the aralkoxide which can be utilized as the anionic species of the metal compound (or the metal complex) can be a $C_7$ to $C_{20}$ aralkoxide; alternatively, a $C_7$ to $C_{15}$, aralkoxide; or alternatively, a $C_7$ to $C_{10}$ aralkoxide. In an embodiment, each aroxide which can be utilized as the anionic species of the metal compound (or the metal complex) independently can be benzoxide or a substituted benzoxide; or alternatively, a benzoxide. Substituent groups (or substituents) phenoxide are independently disclosed herein and can be utilized without limitation to further describe any general or specific the substituted cycloalkoxide, aroxide, and/or aralkoxide which can be utilized as the anionic specie of the metal compound (or the metal complex).

In an embodiment, each carboxylate which can be utilized as the anionic species of the metal compound (or the metal complex) independently can be a $C_2$ to $C_{20}$ carboxylate; alternatively, a $C_3$ to $C_{15}$/carboxylate; or alternatively, a $C_3$ to $C_{10}$ carboxylate. In an embodiment, each carboxylate which can be utilized as the anionic species of the metal compound (or the metal complex) independently can be acetate, propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, acetate, propionate, a butyrate, a pentanoate, a hexanoate, a heptanoate, an octanoate, a nonanoate, or a decanoate. In an embodiment, each carboxylate which can be utilized as the anionic species of the metal compound (or the metal complex) independently can be acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, or caprate (n-decanoate); alternatively, acetate; alternatively, propionate; alternatively, n-butyrate; alternatively, isobutyrate; alternatively, valerate (n-pentanoate); alternatively, capronate (n-hexanoate); alternatively, caprylate (n-octanoate); alternatively, 2-ethylhexanoate; alternatively, caprate (n-decanoate); alternatively, laurate (n-dodecanoate); or alternatively, stearate(n-octadecanoate). In other embodiments, the carboxylate which can be utilized as the anionic species of the metal compound (or the metal complex) independently can be triflate.

In an aspect, each β-dionate group which can be utilized as the anionic species of the metal compound (or the metal complex) independently can be a $C_5$ to $C_{20}$ β-dionate group; alternatively, a $C_5$ to $C_{15}$ β-dionate group; or alternatively, a $C_5$ to $C_{10}$ β-dionate group. In an embodiment, each β-dionate group which can be utilized as the anionic species of the metal compound (or the metal complex) independently can be acetylacetonate (alternatively, 2,4-pentanedionate), hexafluoroacetylacetone (alternatively, 1,1,1,5,5,5-hexafluoro-2,4-pentanedionate), benzoylacetonate, or 1,3-diphenyl-1,3-propanedionate; alternatively, acetylacetonate; alternatively, hexafluoroacetylacetone; alternatively, benzoylacetonate, or alternatively, 1,3-diphenyl-1,3-propanedionate.

In an embodiment, the metal compound complexed to the ligand can be, comprise, or consist essentially of, a metal halide. In some embodiments, the metal compound can be, comprise, or consist essentially of, a chromium(II) halide, a chromium(III) halide, an iron(II) halide, an iron(III) halide, a cobalt(II) halide, or a cobalt(III) halide; alternatively, a chromium(II) halide or chromium(III) halide alternatively, an iron(II) halide or iron(III) halide; or alternatively, a cobalt(II) halide or a cobalt(III) halide. In other embodiments, the metal compound can be, comprise, or consist essentially of, a chromium(II) halide; alternatively, chromium(III) halide; alternatively, an iron(II) halide; alternatively, an iron(III) halide; alternatively, a cobalt(II) halide; or alternatively, a cobalt(III) halide.

In an embodiment, the metal compound(s) can be chromium(II) chloride, chromium(III) chloride, chromium(II) fluoride, chromium(III) fluoride, chromium(II) bromide, chromium(III) bromide, chromium(II) iodide, chromium (III) iodide, chromium(II) acetate, chromium(III) acetate, chromium(II) acetylacetonate, chromium(III) acetylacetonate, chromium(II) 2-ethylhexanoate, chromium(III) 2-ethylhexanoate, chromium(II) triflate, chromium(III) triflate, chromium(II) nitrate, chromium(III) nitrate, iron(II) chloride, iron(III) chloride, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, iron(II) nitrate, iron(III) nitrate, cobalt(II) chloride, cobalt (III) chloride, cobalt(II) fluoride, cobalt(III) fluoride, cobalt (II) bromide, cobalt(III) bromide, cobalt(II) iodide, cobalt (III) iodide, cobalt(II) acetate, cobalt(III) acetate, cobalt(II) acetylacetonate, cobalt(III) acetylacetonate, cobalt(II) benzoylacetonate, cobalt(III) benzoylacetonate, cobalt(II) acetylacetonate, cobalt(III) acetylacetonate, cobalt(II) 2-ethylhexanoate, cobalt(III) 2-ethylhexanoate, cobalt(II) triflate, cobalt(III) triflate, cobalt(II) nitrate, cobalt(III) nitrate, vanadium(III) chloride, vanadium(II) chloride, vanadium(III) chloride, vanadium(III) chloride tetrahydrofuran complex, vanadium(II) iodide, vanadium(III) iodide, manganese(II) acetate, manganese(III) acetate, manganese(II) acetylacetonate, manganese(III) acetylacetonate, manganese(II) bromide, manganese(III) bromide, manganese(II) chloride, manganese(III) chloride, manganese(II) fluoride, manganese(III) fluoride, manganese(II) iodide, manganese(III) iodide, or any combination thereof. In some embodiments, the metal compound can be chromium(II) chloride, chromium(III) chloride, chromium(II) acetate, chromium(III) acetate, chromium(II) acetylacetonate, chromium(III) acetylacetonate, iron(II) chloride, iron(III) chloride, iron(II)

acetate, iron(III) acetate, iron(II) acetylacetonate, iron(III) acetylacetonate, cobalt(II) chloride, cobalt(III) chloride, cobalt(II) acetate, cobalt(III) acetate, or cobalt(II) acetylacetonate, cobalt(III) acetylacetonate, or any combination thereof. In other embodiments, the metal compound can be chromium(II) chloride, chromium(III) chloride, chromium (II) acetylacetonate, chromium(III) acetylacetonate, iron(II) chloride, iron(III) chloride, iron(II) acetylacetonate, iron(III) acetylacetonate, cobalt(II) chloride, cobalt(III) chloride, cobalt(II) acetylacetonate, cobalt(III) acetylacetonate, or any combination thereof. In further embodiments, the metal compound can be chromium(II) chloride; alternatively, chromium(II) chloride; alternatively, chromium(II) acetylacetonate; alternatively, chromium(III) acetylacetonate; alternatively, iron(II) chloride; alternatively, iron(II) acetylacetonate; alternatively, cobalt(II) chloride; or alternatively, cobalt(II) acetylacetonate.

Depictions of specific metal compounds, $MX_n$, complexed to a ligand can be prepared (and are readily apparent) by replacing $MX_n$ with any specific metal compound provided herein and/or showing the ligation bonds of specific metal compound to any ligand provided herein in a manner similar to the depictions of the metal compound, $MX_n$, complexed to respective general ligand depicted herein. These depictions can have the designation Structure MCPBI Q1, Structure BMCPBI Q2, or Structure MC Y where MC represents the specific metal compound, and Q1, Q2, and Y represent the ligand designation of the ligand having Structure PBI Q1, Structure BPBI Q2, or Structure Y, respectively, or any other ligand provided herein.

In an aspect, the metal compound complexed to a ligand can be an iron compound complexed to a ligand comprising a pyridine bisimine group. In an embodiment, the metal compound complexed to a ligand can be an iron compound complexed to a ligand comprising a pyridine bisimine group. In some embodiments, the metal compound can be complexed to a ligand can be an iron compound complexed to a ligand comprising only one pyridine bisimine group; or alternatively, an iron compound complexed to a ligand comprising only of two pyridine bisimine groups. In an embodiment, a metal compound complexed to a ligand can be, comprise, or consist essentially of, Structure FePBI II, Structure FePBI III, or Structure BFePBI III; alternatively, Structure FePBI II or Structure FePBI III; alternatively, Structure FePBI II; alternatively, Structure FePBI III; or alternatively, Structure BFePBI III.

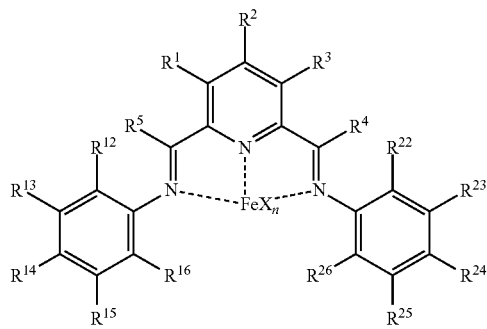

Structure FePBI II

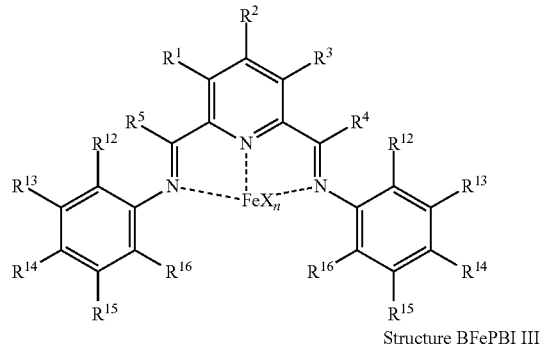

Structure FePBI III

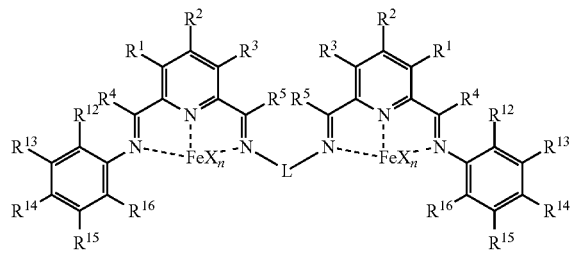

Structure BFePBI III

Generally, $R^1$, $R^2$, $R^3$, $R^4$, $R^5$, $R^6$, $R^7$, $R^{12}$, $R^{13}$, $R^{14}$, $R^{15}$, $R^{16}$, $R^{22}$, $R^{23}$, $R^{24}$, $R^{25}$, and $R^{26}$, L, $FeX_n$, are independent elements of the iron complexes having Structure FePBI II, Structure FePBI III, and Structure BFePBI III. The iron complexes having Structure FePBI II, Structure FePBI III, and Structure BFePBI III can be described utilizing any aspect or embodiment of $R^1$, $R^2$, $R^3$, $R^4$, $R^5$, $R^6$, $R^7$, $R^{12}$, $R^{13}$, $R^{14}$, $R^{15}$, $R^{16}$, $R^{22}$, $R^{23}$, $R^{24}$, $R^{25}$, and $R^{26}$ described herein, any aspect or embodiment of L described herein, and any aspect or embodiment of the metal compound $FeX_n$ described herein (including any aspect or embodiment of X described herein, and any aspect or embodiment of n described herein). Other structures for the iron compound complexed to a ligand are readily apparent from the present disclosure by taking any iron compound provided herein and any ligand provided herein.

It should be noted that the iron complex structures depicted herein can further comprise a neutral ligand other than the non-pyridine bisimine. While the non-pyridine bisimine neutral ligand for the iron complex structures is not shown, it should be understood that the iron complex structure depiction without the non-pyridine bisimine neutral ligand does not limit the iron complexes to those not having a non-pyridine bisimine neutral ligand. In fact the iron complex structures which can be utilized in any aspect disclosed herein and any embodiment disclosed herein can include a non-pyridine bisimine neutral ligand and that these depictions provided herein do not limit iron complexes to those which do not comprise a non-pyridine bisimine neutral ligand regardless of the language utilized to describe the iron complexes. Non-pyridine bisimine neutral ligands are provide herein (e.g., as non-pyridine bisimine neutral ligands for the general metal complexes) and can be utilized without limitation to further describe the iron complexes.

In a non-limiting aspect of the iron complex having BFePBI III, each carbon atom of L attached to the imine nitrogen atom can be an aromatic carbon atom and as such can be any group described herein wherein each carbon atom of L attached to the imine nitrogen atom can be an aromatic carbon atom. In another non-limiting aspect, of the iron complexes having Structure BFePBI III, L can have Structure 8L, 9L, 10L, 11L, 12L, 13L, and/or 14L; alternatively, Structure 8L, 9L, or 10L; alternatively, Structure 11L, 12L, 13L, or 14L; alternatively, Structure 11L or 12L; alternatively, Structure 13L or 14L; alternatively, Structure 8L; alternatively, Structure 9L; alternatively, Structure 10L; alternatively, Structure 11L; alternatively, Structure 12L; alternatively, Structure 13L; or alternatively, Structure 14L.

In a non-limiting embodiment of the iron complexes having Structure FePBI II, Structure FePBI III, or Structure BFePBI III, each anion, X, independently can be a halide. Halides which can be utilized as X have been independently disclosed herein and can be utilized without limitation to further describe the iron complexes having Structure FePBI II, Structure FePBI III, or Structure BFePBI III. Other depictions of $FeX_1$, complexed to a ligand can be prepared (and are readily apparent) by showing the ligation bonds of $FeX_1$, to any ligand provided herein in a manner similar to the depictions of the metal compound, $MX_n$, complexed to respective general ligand depicted herein. Further depictions of $FeX_n$ complexed to a ligand can be prepared (and are readily apparent) by replacing $MX_n$ with any iron compound provided herein and/or showing the ligation bonds of iron compound to any ligand provided herein in a manner similar to the depictions of the metal compound, $MX_n$, complexed to any respective general ligand depicted herein. These depictions can have the structure designation FePBI Q1 or BFePBI Q2 where Q1 and Q2 represent the ligand designation of the ligand having Structure PBI Q1 or BPBI Q2, respectively, or any other ligand provided herein.

In some non-limiting embodiments, the iron compound complexed to a ligand can have any structure disclosed herein can be $FeCl_2$ or $FeCl_3$; alternatively, $FeCl_2$; or alternatively, $FeCl_3$. Other depictions of $FeCl_2$ (or $FeCl_3$) complexed to a ligand can be prepared by replacing $MX_n$ in any depiction of a metal compound complexed with a ligand provided herein with $FeCl_2$ (or $FeCl_3$); or alternatively, replacing $FeX_n$ in any depiction of an iron compound complexed with a ligand provided herein with $FeCl_2$ (or $FeCl_3$). Further depictions of $FeCl_2$ (or $FeCl_3$) complexed to a ligand can be prepared (and are readily apparent) by showing the ligation bonds of $FeCl_2$ (or $FeCl_3$) to any ligand provided herein in a manner similar to the depictions of the metal compound (or general iron compound) complexed to respective general ligand depicted herein. These depictions can have the structure designation $FeCl_2PBI$ Q1 (or Structure $FeCl_3PBI$ Q1), Structure $FeCl_2PBI$ Q2 (or Structure $FeCl_3PBI$ Q2), or Structure $FeCl_2$ Y (or Structure $FeCl_3$ Y) where Q1, Q2, and Y represent the ligand designation of the ligand having Structure PBI Q1, Structure BPBI Q2, or Structure Y, respectively, or any other ligand provided herein. It should be noted that the iron chloride complexes can further comprise a neutral ligand other than the pyridine bisimine ligand. While this non-pyridine bisimine neutral ligand for the iron chloride complexes may not be shown, it should be understood that the iron chloride complex depictions without the neutral ligand does not limit the iron chloride complexes to those not having a neutral ligand. In fact the iron chloride complexes which can be utilized in any aspect disclosed herein and any embodiment disclosed herein can include a non-pyridine bisimine neutral ligand and that any depictions provided herein do not limit iron chloride complexes to those which do not comprise a non-pyridine bisimine neutral ligand regardless of the language utilized to describe the iron chloride complexes. Non-pyridine bisimine neutral ligands are provided herein (e.g., as non-pyridine bisimine neutral ligands for the general metal complexes) and can be utilized without limitation to further describe the iron chloride complexes.

Additional descriptions of catalysts suitable for use in the present disclosure can be found in the following U.S. patents and European patent publication U.S. Pat. No. 5,955,555, U.S. Pat. No. 6,103,946, U.S. Pat. No. 6,291,733, U.S. Pat. No. 6,489,497, U.S. Pat. No. 6,451,939, U.S. Pat. No. 6,455,660, U.S. Pat. No. 6,458,739, U.S. Pat. No. 6,472,341, U.S. Pat. No. 6,545,108, U.S. Pat. No. 6,559,091, U.S. Pat. No. 6,657,026, U.S. Pat. No. 6,683,187, U.S. Pat. No. 6,710,006, U.S. Pat. No. 6,911,505, U.S. Pat. No. 6,911,506, U.S. Pat. No. 7,001,964, U.S. Pat. No. 7,045,632, U.S. Pat. No. 7,056,997, U.S. Pat. No. 7,223,893, U.S. Pat. No. 7,456,284, U.S. Pat. No. 7,683,149, U.S. Pat. No. 7,902,415, U.S. Pat. No. 7,994,376 and EP 1229020A1. Each of these documents is incorporated by reference herein in its entirety.

The Lewis acid capable of abstracting capable of abstracting an anionic specie, a hydride, or an alkyl group can be a neutral Lewis acid, a cationic Lewis acid, or any combination thereof; alternatively, a neutral Lewis acid; or alternatively, a cationic Lewis acid. In an embodiment, the Lewis acid can be capable of alkylating the transition metal complex; or alternatively, adding a hydride anion to the transition metal complex. If the Lewis acid is not capable of alkylating the transition metal complex (or alternatively, adding a hydride anion to the transition metal complex), the catalyst system can further comprise an additional agent capable of alkylating the transition metal complex (or alternatively, adding a hydride anion to the transition metal complex).

In a non-limiting embodiment, the neutral Lewis acid can be, comprise, or consist essentially of, $SbF_5$, $Ar_3B$ (wherein Ar is aryl group), and $BF_3$, or any combination thereof; alternatively, $SbF_5$; alternatively, $Ar_3B$; or alternatively, $BF_3$. In a non-limiting embodiment, the cationic Lewis acid can be, comprise, or consist essentially of, NaBAF, silver trifluoromethanesulfonate, $HBF_4$, or $[C_6H_5NH(CH_3)_2]^+[B(C_6F_5)_4]^-$. When an additional agent capable of alkylating the transition metal complex is necessary, the agent capable of alkylating the transition metal complex can be, comprise, or consist essentially of, a metal alkyl compound. Metal alkyl compounds are described herein and can be utilized, without limitation, as the agent capable of alkylating the transition metal complex. When an additional agent capable of adding a hydride anion to the transition metal complex is necessary, the agent capable of adding a hydride anion to the transition metal complex can be, comprise, or consist essentially of, a metal hydride compound. Metal hydride compounds which can be utilized, without limitation, as the agent capable of adding a hydride anion to the transition metal complex can be, comprise, or consist essentially of $NaBH_4$, $LiAlH_4$, $AlH_3$, an alkylaluminum hydride, or any combination thereof; alternatively, $NaBH_4$; alternatively, $LiAlH_4$; alternatively, $AlH_3$; or alternatively, an alkylaluminum hydride. Alkyl groups are describe herein (e.g., as alkyl group for the metal alkyl compounds) and the alkyl group can be utilized without limitation as the alkyl groups for the alkylaluminum hydride.

The metal alkyl compound which can be utilized in the catalyst system of this disclosure can be any heteroleptic or homoleptic metal alkyl compound. In an embodiment, the metal alkyl compound can comprise, consist essentially of, or consist of, a non-halide metal alkyl, a metal alkyl halide, or any combination thereof; alternatively, a non-halide metal alkyl; or alternatively, a metal alkyl halide.

In an embodiment, the metal of the metal alkyl compound can comprise, consist essentially of, or consist of, a group 1, 2, 11, 12, 13, or 14 metal; or alternatively, a group 13 or 14 metal; or alternatively, a group 13 metal. In some embodiments, the metal of the metal alkyl compound (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl compound (non-halide metal alkyl or metal alkyl halide) can comprise, consist essentially of, or consist of, a lithium alkyl compound, a sodium alkyl compound, a magnesium alkyl compound, a boron alkyl compound, a zinc alkyl compound, or an aluminum alkyl compound. In some embodiments, the metal alkyl (non-halide metal alkyl or metal alkyl halide) can comprise, consist essentially of, or consist of, an aluminum alkyl compound.

In an embodiment, the aluminum alkyl compound can be a trialkylaluminum, an alkylaluminum halide, an alkylaluminum alkoxide, an aluminoxane, or any combination thereof. In some embodiments, the aluminum alkyl compound can be a trialkylaluminum, an alkylaluminum halide, an aluminoxane, or any combination thereof; or alternatively, a trialkylaluminum, an aluminoxane, or any combination thereof. In other embodiments, the aluminum alkyl compound can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the Formula I:

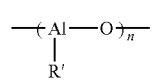

Formula I wherein R' is a linear or branched alkyl group. Alkyl groups for metal alkyl compounds are independently described herein and can be utilized without limitation to further describe the aluminoxanes having Formula I. Generally, n of Formula I is greater than 1; or alternatively, greater than 2. In an embodiment, n can range from 2 to 15; or alternatively, range from 3 to 10.

In an aspect, each halide of any metal alkyl halide disclosed herein independently can be, comprise, or consist essentially of, fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any metal alkyl compound disclosed herein (non-halide metal alkyl or metal alkyl halide) independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) of any metal alkyl compound disclosed herein (non-halide metal alkyl or metal alkyl halide) independently can be, comprise, or consist essentially of, a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, alkyl group independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any metal alkyl alkoxide disclosed herein independently can be, comprise, or consist essentially of, a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein independently can be, comprise, or consist essentially of, a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any metal alkyl alkoxide disclosed herein independently can be, comprise, or consist essentially of, a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the metal alkyl compound can be, comprise, or consist essentially of, methyl lithium, n-butyl lithium, sec-butyl lithium, tert-butyl lithium, diethyl magnesium, di-n-butylmagnesium, ethylmagnesium chloride, n-butylmagnesium chloride, and diethyl zinc.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, alkylaluminum halide can be, comprise, or consist essentially of, diethylaluminum chloride, diethylaluminum bromide, ethylaluminum dichloride, ethylaluminum sesquichloride, and mixtures thereof. In some non-limiting embodiments, alkylaluminum halide can be, comprise, or consist essentially of, diethylaluminum chloride, ethylaluminum dichloride, ethylaluminum sesquichloride, and mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentyl-aluminoxane, iso-pentylaluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentylaluminoxane; alternatively, iso-pentylaluminoxane; or alternatively, neopentylaluminoxane.

In an aspect, the metal alkyl compound and transition metal complex can be combined in any ratio that can form an active catalyst system. In an embodiment, the minimum metal of the metal alkyl compound to the metal of the transition metal complex molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, greater than or equal to 150:1; or alternatively, greater than or equal to 200:1. In an embodiment, the maximum metal of the metal alkyl compound to the metal of the transition metal complex molar ratio can be 100,000:1; alternatively, 50,000:1; alternatively, 25,000:1; alternatively, 10,000:1; alternatively, 5,000:1, alternatively, 2,500:1; alternatively, 2,000:1; alternatively, 1,500:1; alternatively, 1,250:1; alternatively, 1,250:1; or alternatively, 1,000:1. In an embodiment, the minimum metal of the metal alkyl compound to the metal of the transition metal complex molar ratio can range from any minimum metal of the metal alkyl compound to the metal of the transition metal complex molar ratio disclosed herein to any maximum of the metal alkyl compound to the metal of the transition metal complex molar ratio disclosed herein. In some non-limiting embodiments, the metal of the metal alkyl compound to the metal of the transition metal complex molar ratio can range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1; or alternatively, range from 100:1 to 1,500:1. Other metal of the metal alkyl compound to the metal of the transition metal complex molar ratios are readily apparent from the present disclosure.

When a metal alkyl compound having a specific metal and a transition metal complex having a specific transition metal are utilized, the metal of the metal alkyl to the metal of the transition metal complex molar ratio can be stated as a specific metal of the metal alkyl compound to specific transition metal of transition metal complex molar ratio. For example, when the metal alkyl compound is an alkylaluminum compound (e.g., trialkylaluminum, alkylaluminum halide, alkylaluminum alkoxide, and/or aluminoxane) and the transition metal complex is an iron compound complexed to a ligand comprising a pyridine bisimine group, the metal of the metal alkyl compound to metal of the transition metal compound can be an aluminum to iron molar ratio. In some embodiments, the minimum aluminum to iron molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, greater than or equal to 150:1; or alternatively, greater than or equal to 200:1. In an embodiment, the maximum aluminum to iron molar ratio can be 100,000:1; alternatively, 50,000:1; alternatively, 25,000:1; alternatively, 10,000:1; alternatively, 5,000:1, alternatively, 2,500:1; alternatively, 2,000:1; alternatively, 1,500:1; alternatively, 1, 250:1; alternatively, 1,250:1; or alternatively, 1,000:1. In an embodiment, the aluminum to iron molar ratio can range from any minimum aluminum to iron molar ratio disclosed herein to any maximum aluminum to iron molar ratio disclosed herein. In some non-limiting embodiments, the aluminum to iron molar ratio can range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1; or alternatively, range from 100:1 to 1,500:1. Other aluminum to iron molar ratios are readily apparent from the present disclosure. Other specific metal of the metal alkyl compound to the specific metal of the transition metal complex molar ratios are readily apparent from the present disclosure.

In an aspect, the present disclosure relates to an olefin oligomerization process. In an embodiment, the olefin oligomerization process can comprise contacting an olefin and a catalyst system comprising i) a transition metal complex comprising a transition metal compound complexed to a ligand and ii) a metal alkyl compound to from an olefin oligomer product; alternatively, the olefin oligomerization process can comprise contacting an olefin and a catalyst system comprising i) a transition metal complex comprising a transition metal compound complexed to a ligand and ii) a Lewis acid capable of abstracting capable of abstracting an anionic specie, a hydride, or an alkyl group (or a Lewis acid and an agent capable of alkylating the transition metal complex and/or adding a hydride anion to the transition metal complex) to from an olefin oligomer product; alternatively, the olefin oligomerization process can comprise contacting a an olefin, hydrogen, and a catalyst system comprising i) a transition metal complex comprising a transition metal compound and ii) a metal alkyl compound to form an olefin oligomer product; or alternatively, the olefin oligomerization process can comprise contacting a an olefin, hydrogen, and a catalyst system comprising i) a transition metal complex comprising a transition metal compound and ii) a Lewis acid capable of abstracting capable of abstracting an anionic specie, a hydride, or an alkyl group (or a Lewis acid and an agent capable of alkylating the transition metal complex and/or adding a hydride anion to the transition metal complex) to form an olefin oligomer product. In some embodiments, the olefin oligomerization process can comprise: a) contacting transition metal complex and a metal alkyl to form a catalyst system; and b) contacting the catalyst system and an olefin to form an olefin oligomer product; alternatively, a) contacting transition metal complex and a Lewis acid capable of abstracting capable of abstracting an anionic specie, a hydride, or an alkyl group (or a Lewis acid and an agent capable of alkylating the transition metal complex and/or adding a hydride anion to the transition metal complex) to form a catalyst system; and b) contacting the catalyst system and an olefin to form an olefin oligomer product; alternatively, a) contacting a transition metal complex and a metal alkyl to form a catalyst system; and b) contacting the catalyst system, an olefin, and hydrogen to form an olefin oligomer product; or alternatively, a) contacting a transition metal complex and a Lewis acid capable of abstracting capable of abstracting an anionic specie, a hydride, or an alkyl group (or a Lewis acid and an agent capable of alkylating the transition metal complex and/or adding a hydride anion to the transition metal complex) to form a catalyst system; and b) contacting the catalyst system, an olefin, and hydrogen to form an olefin oligomer product. In other embodiments, the olefin oligomerization process can comprise contacting a) an olefin, b) a transition metal complex, and c) a metal alkyl compound to form an olefin oligomer product; alternatively, the olefin oligomerization process can comprise contacting a) an olefin, b) a transition metal complex, and c) a Lewis acid capable of abstracting capable of abstracting an anionic specie, a hydride, or an alkyl group (or a Lewis acid and an agent capable of alkylating the transition metal complex and/or adding a hydride anion to the transition metal complex) to form an olefin oligomer product; alternatively, the olefin oligomerization process can comprise contacting a) an olefin, b) a transition metal complex, c) a metal alkyl compound, and d) hydrogen to produce an olefin oligomer product; or alternatively, the olefin oligomerization process can comprise contacting a) an olefin, b) a transition metal complex, c) a Lewis acid capable of abstracting capable of abstracting an anionic specie, a hydride, or an alkyl group (or a Lewis acid and an agent capable of alkylating the transition metal complex and/or adding a hydride anion to the transition metal complex), and d) hydrogen to produce an olefin oligomer product.

In an embodiment, the olefin oligomer product can be formed under conditions capable forming an olefin oligomer product. In an embodiment, the olefin oligomer product can be formed in an olefin oligomerization reactor. In some embodiments, the catalyst system can be prepared in the presence of a solvent; or alternatively, the catalyst system can be contact with a solvent prior to contact with the olefin (or olefin and hydrogen). In another embodiment, a diluent (olefin oligomerization diluent) can also be contacted with the olefin and the catalyst system; alternatively, contacted with the olefin, the transition metal complex, and the metal alkyl compound; alternatively, the transition metal complex, and the Lewis acid capable of abstracting capable of abstracting an anionic specie, a hydride, or an alkyl group (or the Lewis acid and the agent capable of alkylating the transition metal complex and/or adding a hydride anion to the transition metal complex); alternatively, the olefin, the catalyst system, and hydrogen; alternatively, the olefin, hydrogen, the transition metal complex, and the metal alkyl compound; or alternatively, the olefin, hydrogen, the transition metal complex, and the Lewis acid capable of abstracting capable of abstracting an anionic specie, a hydride, or an alkyl group (or the Lewis acid and the agent capable of alkylating the transition metal complex and/or adding a hydride anion to the transition metal complex).

Generally, the olefin, the catalyst system (alternatively, olefin, transition metal complex, and metal alkyl compound; or alternatively, olefin, transition metal complex, and Lewis acid capable of abstracting capable of abstracting an anionic specie, a hydride, or an alkyl group (or Lewis acid and an agent capable of alkylating the transition metal complex and/or adding a hydride anion to the transition metal complex)), the olefin oligomer product, the conditions capable of producing an olefin oligomer product, any solvent, the olefin oligomerization diluent, and the olefin oligomerization reactor, among other features are independent elements of the olefin oligomerization process and are independently described herein, among other olefin oligomerization features. The olefin oligomerization process can be described using any combination of any aspect or embodiment of the olefin described herein, and any aspect or embodiment of the catalyst system described herein (alternatively, any aspect or embodiment of the transition metal complex described herein, and any aspect or embodiment of the metal alkyl compound described herein; or alternatively, any aspect or embodiment of the Lewis acid capable of abstracting capable of abstracting an anionic specie, a hydride, or an alkyl group (or any aspect or embodiment of the Lewis acid and any aspect or embodiment of the agent capable of alkylating the transition metal complex and/or adding a hydride anion to the transition metal complex)), any aspect or embodiment of the olefin oligomer product described herein, any aspect or embodiment of the solvent described herein, any aspect of embodiment of the olefin oligomerization diluent described herein, any aspect or embodiment of the olefin oligomerization process described herein, and any aspect or embodiment of any other olefin oligomerization feature described herein.

Generally, the olefin and the catalyst system can be contacted in any manner; alternatively, the olefin, the transition metal complex, and the metal alkyl compound can be contacted in any manner; or alternatively, the olefin, the transition metal complex, and the Lewis acid capable of abstracting capable of abstracting an anionic specie, a hydride, or an alkyl group (or the Lewis acid and the agent capable of alkylating the transition metal complex and/or adding a hydride anion to the transition metal complex) can be contacted in any manner. Herein the methods of contact of the components for the olefin oligomerization are illustrated utilizing a metal alkyl compound. These methods can be adapted for catalyst system utilizing a Lewis acid capable of abstracting capable of abstracting an anionic specie, a hydride, or an alkyl group (or a Lewis acid and an agent capable of alkylating the transition metal complex and/or adding a hydride anion to the transition metal complex) by substituting the Lewis acid capable of abstracting capable of abstracting an anionic specie, a hydride, or an alkyl group (or the Lewis acid and the agent capable of alkylating the transition metal complex and/or adding a hydride anion to the transition metal complex) for the metal alky compound.

In an aspect, the catalyst system components (i.e., the transition metal complex and the metal alkyl compound) can be contacted prior to the contact of the catalyst system with the olefin. In some embodiments, the olefin oligomerization process can comprise a step where the olefin and the catalyst system can be simultaneously (or substantially simultaneously) introduced into an olefin oligomerization reactor; or alternatively, comprise steps where the olefin and the catalyst system are contacted outside of the olefin oligomerization reactor and then introduced into the olefin oligomerization reactor. In an embodiment where the olefin and the catalyst system are contacted outside of the olefin reactor, the olefin can be added to the catalyst system; alternatively, the catalyst system can be added to the olefin; or alternatively, the olefin and the catalyst system can be contacted simultaneously (or contacted substantially simultaneously) outside of the olefin oligomerization reactor and then introduced into the olefin oligomerization reactor. In yet other embodiments, the olefin can be introduced into the olefin oligomerization reactor and then the catalyst system introduced into the olefin oligomerization reactor. In further embodiments, the catalyst system can be introduced into the olefin oligomerization reactor and then the olefin introduced into the olefin oligomerization reactor.

In some embodiments, the catalyst system can be part of a composition (e.g., a catalyst system composition) which further comprises a solvent. In other embodiments, the olefin can be part of a composition (e.g., an olefin composition) which further comprises a solvent. In an embodiment, the solvent can be the olefin oligomerization diluent; or alternatively, the solvent can be different from the olefin oligomerization diluent. In embodiments where the catalyst system and the olefin are parts of separate compositions which further comprise a solvent, the solvent which can be utilized in the catalyst system composition can be the same as the solvent which can be utilized in the olefin composition; or alternatively, the solvent which can be utilized in the catalyst system composition can be different from the solvent which can be utilized in the olefin composition.

In an aspect, the olefin oligomer product can be formed in the presence of an olefin oligomerization diluent. In embodiments which utilize an olefin oligomerization diluent, the olefin oligomerization diluent can be simultaneous (or substantially simultaneously) introduced into the olefin oligomerization reactor with the olefin and the catalyst system; or alternatively, the olefin oligomerization diluent can be simultaneous (or substantially simultaneously) introduced into the olefin oligomerization reactor with the olefin, the transition metal complex, and the metal alkyl compound. In other embodiments, the olefin oligomerization diluent (or a portion of the olefin oligomerization diluent) can be contacted with the catalyst system to form a catalyst system composition comprising, or consisting essentially of, the catalyst system and the olefin oligomerization diluent, and the catalyst system composition and then the olefin simultaneously introduced into the olefin oligomerization reactor; alternatively, the olefin oligomerization diluent (or a portion of the olefin oligomerization diluent) can be contacted with the olefin to form an olefin composition comprising, or consisting essentially of, the olefin and the olefin oligomerization diluent, and then the olefin composition and the catalyst system simultaneously introduced into the olefin oligomerization reactor; or alternatively, i) the olefin oligomerization diluent (or a portion of the olefin oligomerization diluent) can be contacted with the catalyst system to form a catalyst system composition comprising, or consisting essentially of, the catalyst system and the olefin oligomerization diluent, ii) a portion the olefin oligomerization diluent can be contacted with the olefin to form an olefin composition comprising, or consisting essentially of, the olefin and the olefin oligomerization diluent, and then the olefin composition and the catalyst system simultaneously introduced into the olefin oligomerization reactor, and iii) the catalyst system composition and the olefin composition can be introduced into the olefin oligomerization reactor. When a portion of the olefin oligomerization diluent is contacted with the catalyst system and/or the olefin to form a catalyst system composition and/or a olefin composition, respectively, any remaining portion of the olefin oligomerization solvent can be introduced into the olefin oligomerization reactor in any manner (e.g., simultaneously with the other components, before the introduction of the other component, or after the addition of the other components).

In an aspect, the olefin oligomerization process can comprise a step where the olefin, the transition metal complex, and the metal alkyl compound can be simultaneously (or substantially simultaneously) introduced into an olefin oligomerization reactor. In another aspect, the olefin oligomerization process can comprise a step where the olefin, the transition metal complex, and the metal alkyl compound can be simultaneously (or substantially simultaneously) contacted outside of an olefin oligomerization reactor and then introduced into the olefin oligomerization reactor.

In an aspect, the olefin oligomerization process can comprise a step where the metal alkyl compound and a mixture comprising i) the olefin and ii) the transition metal complex (or alternatively, a mixture comprising, or consisting essentially of, i) the olefin, ii) the transition metal complex, and iii) an olefin oligomerization diluent) can be simultaneously (or substantially simultaneously) introduced into an olefin oligomerization reactor; or alternatively, comprise steps where the metal alkyl compound and a mixture comprising i) the olefin and ii) the transition metal complex (or alternatively, a mixture comprising or consisting essentially of, i) the olefin, ii) the transition metal complex, and iii) an olefin oligomerization diluent) are contacted outside of the olefin oligomerization reactor and then introduced into the olefin oligomerization reactor. In some embodiments where the metal alkyl compound and the mixture are contacted outside of the olefin oligomerization reactor, the metal alkyl compound can be added to the mixture comprising i) the olefin and ii) the transition metal complex (or alternatively, the mixture comprising, or consisting essentially of, i) the olefin, ii) the transition metal complex, and iii) an olefin oligomerization diluent); alternatively, the mixture comprising i) the olefin and ii) the transition metal complex (or alternatively, the mixture comprising, or consisting essentially of, i) the olefin, ii) the transition metal complex, and iii) an olefin oligomerization diluent) can be added to the metal alkyl compound; or alternatively, the metal alkyl compound and the mixture comprising i) the olefin and ii) the transition metal complex (or alternatively, the mixture comprising, or consisting essentially of, i) the olefin, ii) the transition metal complex, and iii) an olefin oligomerization diluent) can be contacted simultaneously (or contacted substantially simultaneously). In an embodiment, the mixture comprising the olefin and the transition metal complex can be prepared by adding the olefin to the transition metal complex; alternatively, adding the transition metal complex to the olefin; or alternatively, the olefin and the transition metal complex can be contacted simultaneously (or substantially simultaneously).

In an embodiment, the olefin oligomerization process can comprise a step where the transition metal complex and a mixture comprising i) the olefin and ii) the metal alkyl compound (or alternatively, a mixture comprising or consisting essentially of, i) the olefin, ii) the metal alkyl compound, and iii) an olefin oligomerization diluent) can be simultaneously (or substantially simultaneously) introduced into an olefin oligomerization reactor; or alternatively, comprise steps where the transition metal complex and a mixture comprising i) the olefin and ii) the metal alkyl compound (or alternatively, a mixture comprising or consisting essentially of, i) the olefin, ii) the metal alkyl compound, and iii) an olefin oligomerization diluent) can be contacted outside of the olefin oligomerization reactor and then introduced into the olefin oligomerization reactor. In some embodiments where the transition metal complex and the mixture are contacted outside of the olefin oligomerization reactor, the transition metal complex can be added to the mixture comprising i) the olefin and ii) the metal alkyl compound (or alternatively, the mixture comprising, or consisting essentially of, i) the olefin, ii) the metal alkyl compound, and iii) an olefin oligomerization diluent); alternatively, the mixture comprising i) the olefin and ii) the metal alkyl compound (or alternatively, the mixture comprising, or consisting essentially of, i) the olefin, ii) the metal alkyl compound, and iii) an olefin oligomerization diluent) can be added to the transition metal complex; or alternatively, the transition metal complex and the mixture comprising i) the olefin and ii) the metal alkyl compound (or alternatively, the mixture comprising, or consisting essentially of, i) the olefin, ii) the metal alkyl compound, and iii) an olefin oligomerization diluent) can be contacted simultaneously (or contacted substantially simultaneously). In an embodiment, the mixture comprising the olefin and the metal alkyl compound can be prepared by adding the olefin to the metal alkyl compound; alternatively, adding the metal alkyl compound to the olefin; or alternatively, the olefin and the metal alkyl compound can be contacted simultaneously (or substantially simultaneously).

In yet another aspect, the transition metal complex and the metal alkyl compound can contact each other in the presence of the olefin. In an embodiment, the transition metal complex and the metal alkyl compound can simultaneously (or substantially simultaneously) contact the olefin; or alternatively, the transition metal complex, the metal alkyl compound, and the olefin can be contacted simultaneously (or substantially simultaneously). In some embodiments, a mixture comprising the transition metal complex and the olefin can be contacted (in any manner described herein) with the metal alkyl compound. In yet other embodiments, a mixture comprising the metal alkyl compound and the olefin can be contacted (in any manner described herein) with the transition metal complex.

In an embodiment, an olefin oligomerization diluent can be simultaneously (or substantially simultaneously) introduced into the olefin oligomerization reactor along with the olefin and catalyst system (or alternatively, the olefin, the transition metal complex, and the metal alkyl compound). In other embodiments, an olefin oligomerization diluent (or a portion of the olefin oligomerization diluent) can be contacted with catalyst system and/or the olefin to form a catalyst system composition comprising (or consisting essentially of) the catalyst system and the olefin oligomerization diluent and/or a olefin composition comprising the olefin and the olefin oligomerization solvent, respectively. When an olefin composition and/or an catalyst system composition are utilized, the olefin composition, the catalyst system composition, and any remaining olefin oligomerization diluent (if any) can be contacted in any method described herein for contacting the olefin, the catalyst system, and the olefin oligomerization diluent (if any) wherein the olefin composition replaces the olefin, the catalyst system composition replaces the catalyst system.

In an embodiment wherein the olefin oligomer product can be formed in the presence of an olefin oligomerization diluent, the olefin, the transition metal complex, the metal alkyl compound, and the olefin oligomerization diluent can be simultaneously introduced into the olefin oligomerization reactor; or alternatively, the olefin, the transition metal complex, the metal alkyl compound, and the olefin oligomerization diluent can be contacted outside of the olefin oligomerization reactor (in any manner described herein) and then introduced into the olefin oligomerization reactor. In some embodiments, the olefin, the transition metal complex, and the metal alkyl can be introduced (in any manner described herein) into an olefin oligomerization reactor containing the oligomerization diluent. In other embodiments, a portion of the olefin oligomerization diluent can be contacted with the olefin, the transition metal complex, and/or the metal alkyl compound to form a olefin composition comprising (or consisting essentially of) the olefin and the olefin oligomerization diluent, a transition metal complex composition comprising (or consisting essentially of) the transition metal complex and the olefin oligomerization diluent, and/or a metal alkyl compound composition comprising (or consisting essentially of) the metal alkyl compound and the olefin oligomerization diluent, respectively. When an olefin composition, a transition metal complex composition, and/or a metal alkyl compound composition are utilized, the olefin composition, the transition metal complex composition, and/or the metal alkyl compound composition and any remaining olefin oligomerization solvent (if any) can be contacted in any method described herein for contacting the olefin, the transition metal complex, the metal alkyl compound, and the olefin oligomerization diluent (if any) wherein the olefin composition replaces the olefin, the transition metal complex composition replaces the transition metal complex, and/or the metal alkyl compound composition replaces the metal alkyl compound.

In an embodiment, a solvent utilized with a catalyst system, a mixture (or composition) comprising (or consisting essentially of) the catalyst system, a mixture (or composition) comprising (or consisting essentially of) a transition metal complex, a mixture (or composition) comprising (or consisting essentially of) a metal alkyl, a mixture (or composition) comprising (or consisting essentially of) a transition metal complex and a metal alkyl, a mixture (or composition) comprising (or consisting essentially of) the olefin, or any other mixture (or composition) utilizing a solvent described herein can be a hydrocarbon, a halogenated hydrocarbon, or any combination thereof; alternatively, a hydrocarbon; or alternatively, a halogenated hydrocarbon. In some embodiments, a solvent utilized with a catalyst system, a mixture (or composition) comprising (or consisting essentially of) the catalyst system, a mixture (or composition) comprising (or consisting essentially of) a transition metal complex, a mixture (or composition) comprising (or consisting essentially of) a metal alkyl, a mixture (or composition) comprising (or consisting essentially of) a transition metal complex and a metal alkyl, a mixture (or composition) comprising (or consisting essentially of) the olefin, or any other mixture (or composition) utilizing a solvent described herein can be an aliphatic hydrocarbon, a halogenated aliphatic hydrocarbon, an aromatic hydrocarbon, a halogenated aromatic compound, or any combination thereof; alternatively, an aliphatic hydrocarbon, a halogenated aliphatic hydrocarbon, or any combination thereof; alternatively, an aromatic hydrocarbon, a halogenated aromatic compound, or any combination thereof; alternatively, an aliphatic hydrocarbon; alternatively, a halogenated aliphatic hydrocarbon; alternatively, an aromatic hydrocarbon; or alternatively, a halogenated aromatic compound. General and specific hydrocarbons, halogenated hydrocarbons, aliphatic hydrocarbons, halogenated aliphatic hydrocarbons, aromatic hydrocarbons, and halogenated aromatic compounds which can be utilized as a solvent (or as a diluent) are described herein and can be utilized without limitation to further describe the olefin oligomerization process(es) described herein.

In an embodiment, the olefin oligomerization diluent can be a hydrocarbon, a halogenated hydrocarbon, or any combination thereof; alternatively, a hydrocarbon; or alternatively, a halogenated hydrocarbon. In some embodiments, the olefin oligomerization diluent can be an aliphatic hydrocarbon, a halogenated aliphatic hydrocarbon, an aromatic hydrocarbon, a halogenated aromatic, or any combination thereof; alternatively, an aliphatic hydrocarbon, a halogenated aliphatic hydrocarbon, or any combination thereof; alternatively, an aromatic hydrocarbon, a halogenated aromatic compound, or any combination thereof; alternatively, an aliphatic hydrocarbon; alternatively, a halogenated aliphatic hydrocarbon; alternatively, an aromatic hydrocarbon; or alternatively, a halogenated aromatic compound. General and specific hydrocarbons, halogenated hydrocarbons, aliphatic hydrocarbons, halogenated aliphatic hydrocarbon, aromatic hydrocarbon, and halogenated aromatic compounds which can be utilized as a diluent (or a solvent) are described herein and can be utilized without limitation as the olefin oligomerization diluent to further describe the olefin oligomerization process(es) described herein. In some embodiments, the olefin oligomerization diluent can be, can comprise, or can consist essentially of, an alkene. In some embodiments, the alkene which can be utilized as the olefin oligomerization diluent can be, comprise, or consist essentially of, a $C_4$ to $C_{20}$ alkene; alternatively, a $C_4$ to $C_{12}$ alkene; alternatively, a $C_{12}$ to $C_{18}$ alkene. In some embodiments, the alkene which can be utilized as the olefin oligomerization diluent can be, comprise, or consist essentially of, alpha olefin; or alternatively, a normal alpha olefin. In some non-limiting embodiments, the alkene which can be utilized as the olefin oligomerization diluent can be, comprise, or consist essentially of, 1-butene, 1-hexene, 1-octene, 1-decene, 1-dodecene, 1-tetradecene, 1-hexadecene, 1-octadecene, or any combination thereof; alternatively, 1-butene, 1-hexene, 1-octene, 1-decene, 1-dodecene, or any combination thereof; alternatively, 1-dodecene, 1-tetradecene, 1-hexadecene, 1-octadecene, or any combination thereof; alternatively, 1-butene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene.

In an aspect, the olefin oligomer product can be formed in one or more olefin oligomerization reactors. In some embodiments, the olefin oligomer product can be formed in a batch olefin oligomerization reactor, a continuous olefin oligomerization reactor, or any combination thereof; alternatively, a batch olefin oligomerization reactor; or alternatively, a continuous olefin oligomerization reactor. In an embodiment, the continuous olefin oligomerization reactor in which the olefin oligomer product can be formed can comprise, or can be, a loop reactor, a plugged flow reactor, a continuous stirred tank reactor (CSTR), or any combination thereof; alternatively, a loop reactor or a continuous stirred tank reactor; alternatively, a loop reactor; alternatively, a plugged flow reactor; or alternatively, a continuous stirred tank reactor (CSTR). In an embodiment wherein the olefin oligomer product is formed in more than one olefin oligomerization reactor each olefin oligomerization reactor can independently be any olefin oligomerization reactor described herein, and the olefin oligomerization reactors can be arrange in series, parallel, or any combination thereof; alternatively, in series; or alternatively, in parallel.

It should be noted that when multiple olefin oligomerization reactors are utilized each reactor can be independent of each other (regardless of whether they are operated in series or parallel). As such contact modes (if needed), conditions capable of producing the olefin oligomer product, other olefin oligomerization parameters, olefin oligomerization reactor parameters can be different for each reactor. In particular, when multiple olefin oligomerization reactors are utilized in series, each olefin oligomerization reactor can be operated to achieve different goals. For example, a first olefin oligomerization reactor can be operated to i) contact of the olefin and the catalyst system (or the olefin, the transition metal complex, and metal alkyl compound) and ii) initiate production of the olefin oligomer product under a first set of conditions capable of producing the olefin oligomer product to some intermediate olefin conversion and the effluent of the first olefin oligomerization reactor transferred to a second olefin oligomerization reactor operated to achieve the desired olefin conversion at a second set of conditions capable of producing the olefin oligomer product (with or without additional olefin and/or catalyst system (or additional olefin, transition metal complex, and/or metal alkyl compound)).

In an aspect, the olefin oligomer product can be formed under conditions capable of producing an olefin oligomer product. In an embodiment, the conditions capable of producing the olefin oligomer product can comprise, either singly or in any combination, an olefin oligomerization temperature, an olefin oligomerization pressure (or alternatively, an olefin pressure or olefin partial pressure), or an olefin oligomerization time; alternatively, an olefin oligomerization temperature, or an olefin oligomerization time; alternatively, an olefin oligomerization temperature; alternatively, an olefin oligomerization pressure (or alternatively, an olefin pressure or olefin partial pressure); or alternatively, an olefin oligomerization time. It should be noted that selection of the olefin oligomerization temperature, olefin oligomerization pressure, and/or olefin oligomerization time can be impacted by a number of factors such as the transition metal complex stability, cocatalyst identity, catalyst system activity, desired olefin oligomer product distribution K value, and/or desired product purity, among other factors.

It should be noted that when the olefin utilized for the olefin oligomerization process consists essentially of ethylene, the olefin oligomerization can be referred to as an ethylene oligomerization process and ethylene can replace olefin in any feature of the olefin oligomerization process which utilizes the word olefin. In some non-limiting examples, the olefin oligomer product can be referred to as an ethylene oligomer product, the olefin oligomerization conditions can be referred to as ethylene oligomerization conditions, the olefin oligomerization temperature can be referred to as an ethylene oligomerization temperature, the olefin oligomerization time can be referred to as an ethylene oligomerization time, and the olefin oligomerization reactor can be referred to as an ethylene oligomerization reactor. Other olefin oligomerization process features are readily apparent from the present disclosure and can be referred to as the appropriate ethylene oligomerization feature, without limitation, when the olefin consists essentially of ethylene.

Generally, the olefin oligomer product can be produced at any temperature that facilitates the oligomerization of the olefin. In an embodiment, the conditions capable of producing an olefin oligomer product can comprise a minimum oligomerization temperature of (or comprise an oligomerization temperature of at least) −100° C.; alternatively, −50° C.; alternatively, −25° C.; alternatively, 0° C.; alternatively, 20° C.; alternatively, 30° C.; alternatively, 40° C.; alternatively, 50° C.; alternatively, 60° C.; alternatively, 70° C.; alternatively, 80° C.; alternatively, 85° C.; alternatively, 90° C.; alternatively, 95° C.; or alternatively, 100° C. In an embodiment, the conditions capable of producing an olefin oligomer product can comprise a maximum oligomerization temperature of (or comprise an oligomerization temperature of less than or equal to) 300° C.; alternatively, 200° C.;

alternatively, 150° C.; alternatively, 140° C.; alternatively, 130° C.; alternatively, 120° C.; alternatively, 115° C.; alternatively, 110° C.; alternatively, 105° C.; alternatively, 100° C.; alternatively, 95° C.; or alternatively. In an embodiment, the conditions capable of producing an olefin oligomer product can comprise an olefin oligomerization temperature ranging from any minimum olefin oligomerization temperature disclosed herein to any maximum olefin oligomerization temperature disclosed herein. In a non-limiting embodiment, the conditions capable of producing an olefin oligomer product can comprise an olefin oligomerization temperature ranging from −100° C. to 300° C.; alternatively, from 0° C. to 200° C.; alternatively, from 20° C. to 150° C.; alternatively, from 30° C. to 100° C.; alternatively, from 40° C. to 95° C.; alternatively, from 80° C. to 150° C.; alternatively, from 90° C. to 140° C.; alternatively, from 95° C. to 130° C.; alternatively, from 95° C. to 120° C.; alternatively, from 100° C. to 150° C.; alternatively, from 100° C. to 140° C.; alternatively, from 100° C. to 130° C.; alternatively, from 100° C. to 120° C.; alternatively, from 100° C. to 120° C.; or alternatively, from 100° C. to 115° C. Other olefin oligomerization temperature ranges are readily apparent from the present disclosure.

Generally, the olefin oligomer product can be produced at any pressure that facilitates oligomerization of the olefin. In an embodiment, the olefin oligomer product can be produced at an olefin oligomerization pressure greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the olefin oligomer product can be produced at an olefin oligomerization pressure ranging from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the olefin can be a gas at the conditions capable of producing the olefin oligomer product, the olefin oligomerization pressure can be the olefin pressure. When the olefin consists essentially of ethylene, the olefin oligomer product (or ethylene oligomer product) can be produced at an olefin oligomerization pressure (ethylene oligomerization pressure) greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the olefin oligomer product (or ethylene oligomer product) can be produced at an olefin oligomerization pressure (ethylene oligomerization pressure) ranging from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases where the olefin can be a gas at the conditions capable of producing the olefin oligomer product (e.g., ethylene when forming an ethylene oligomer product) and/or inert gases and/or other gases (e.g., hydrogen) can form a portion of the olefin oligomerization pressure, the previously stated olefin oligomerization pressures (e.g., ethylene oligomerization pressure) which can be a condition capable of producing the olefin oligomer product (e.g., ethylene oligomer product) can be an olefin partial pressure (e.g., ethylene partial pressures). In the situation where the olefin provides all or a portion of the olefin oligomerization pressure, the olefin oligomerization pressure can decrease as the olefin is consumed. In this situation, additional olefin (e.g., ethylene) and/or inert gas can be added to maintain a desired olefin oligomerization pressure (e.g., ethylene oligomerization pressure). In some embodiments, additional olefin (e.g., ethylene) can be added at a rate to maintain the olefin oligomerization pressure (e.g., ethylene oligomerization pressure). In other embodiments, the olefin oligomerization pressure can be allowed to decrease without adding any additional olefin and/or inert gas.

In embodiments wherein hydrogen is utilized, the conditions capable of producing an olefin oligomer product can comprise a hydrogen partial pressure. Generally, when hydrogen is utilized, hydrogen can be added in any amount that produces the desired effect. In some embodiments wherein hydrogen is utilized, the conditions capable of producing an olefin oligomer product can comprise a hydrogen partial pressure greater than or equal to 1 psig (kPa); alternatively, greater than or equal to 5 psig (34 kPa); alternatively, greater than or equal to 10 psig (69 kPa); or alternatively, greater than or equal to 15 psig (100 kPa). In other embodiments wherein hydrogen is utilized, the conditions capable of producing an olefin oligomer product can comprise a hydrogen partial pressure ranging from 1 psig (6.9 kPa) to 500 psig (3.5 MPa); alternatively, 5 psig (34 kPa) to 400 psig (2.8 MPa); alternatively, 10 psig (69 kPa) to 300 psig (2.1 MPa); or alternatively, 15 psig (100 kPa) to 200 psig (1.4 MPa).

Generally, the olefin oligomer product can be produced using any an olefin oligomerization time (alternatively, olefin and catalyst system contact time; alternatively, olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) which produces the desired amount olefin oligomer product; alternatively, a desired olefin conversion; or alternatively, a desired catalyst system (or transition metal complex) productivity. In an embodiment, the conditions capable of producing an olefin oligomer product can comprise a minimum oligomerization time (alternatively, olefin and catalyst system minimum contact time; alternatively, olefin, transition metal complex, and alkyl metal compound minimum contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) minimum contact time) of 1 minute; alternatively, 5 minutes; alternatively, 10 minutes; or alternatively, 15 minutes. In an embodiment, the conditions capable of producing an olefin oligomer product can comprise a maximum oligomerization time (alternatively, olefin and catalyst system maximum contact time; alternatively, olefin, transition metal complex, and alkyl metal compound maximum contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) maximum contact time) of less than or equal to 6 hours; alternatively, 4 hours; alternatively, 2 hours; or alternatively, 1.5 hours. In a non-limiting embodiment, the conditions capable of producing an olefin oligomer product can comprise an olefin oligomerization time (alternatively, olefin and catalyst system contact time; alternatively, olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) ranging from 1 minute to 6 hours; alternatively, from 10 minutes to 4 hours; alternatively, 15 minutes to 2 hours. Other olefin oligomerization time ranges (alternatively, olefin and catalyst system contact time ranges; alternatively, olefin, transition metal complex, and alkyl metal compound contact time ranges; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time ranges) are readily apparent from the present disclosure. It should be noted that in some olefin oligomerization reactor designs, the olefin oligomerization time (alternatively, olefin and catalyst system contact time; alternatively, olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) can vary (e.g., a loop reactor). In these situations, the olefin oligomerization time (alternatively, olefin and catalyst system contact time; alternatively, olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) can be referred to as an average. The average olefin oligomerization time (alternatively, average olefin and catalyst system contact time; alternatively, average olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) can be an average minimum, average maximum, or average range having any minimum, maximum, or range for the olefin oligomerization time (alternatively, olefin and catalyst system contact time; alternatively, olefin, transition metal complex, and alkyl metal compound contact time; or alternatively, olefin, transition metal complex, and Lewis acid capable of abstracting capable of abstracting an anionic specie, a hydride, or an alkyl group (or a Lewis acid and an agent capable of alkylating the transition metal complex and/or adding a hydride anion to the transition metal complex) contact time) described herein. It should be noted that when the olefin oligomer product is produced in two or more olefin oligomerization reactors operated in series the olefin oligomerization time refers to the olefin oligomerization time across the entire series of reactors and not one individual reactor of the series.

In an aspect the olefin oligomerization process can be operated to obtain any desired olefin conversion to the olefin oligomer product. Generally, the olefin conversion can be any which provides a desired catalyst system (or transition metal of the transition metal complex) productivity, product purity, and/or process economics, among other factors. In some embodiments, the minimum olefin conversion can be at least 20 wt. %; alternatively, at least 30 wt. %; alternatively, at least 40 wt. %; alternatively, at least 45 wt. %; alternatively, at least 50 wt. %; alternatively, at least 55 wt. %; or alternatively, at least 60 wt. %. In some embodiment, the maximum olefin conversion can be 99 wt. %; alternatively, 95 wt. %; alternatively, 90 wt. %; alternatively, 85 wt. %; alternatively, 80 wt. %; alternatively, 75 wt. %; alternatively, 70 wt. %; or alternatively, 65 wt. %. In other embodiments, the olefin conversion can range from any minimum olefin conversion provided herein to any maximum olefin conversion provided herein. For example, in some non-limiting embodiments, the olefin conversion can range from 30 wt. % to 99 wt. %; alternatively, 30 wt. % to 90 wt. %; alternatively, 40 wt. % to 90 wt. %; alternatively, 45 wt. % to 80 wt. %; alternatively, 45 wt. % to 75 wt. %; or alternatively, 45 wt. % to 70 wt. %. Other olefin conversion ranges are readily apparent from the present disclosure. It should be noted that when the olefin oligomer product is produced in two or more olefin oligomerization reactors operated in series the olefin conversion refers to the olefin conversion across the entire series of reactors and not one individual reactor of the series. In some embodiments where the olefin oligomerization is practiced in a continuous reactor, the olefin conversion (any described herein) can be a single pass olefin conversion. When the olefin consists essentially of ethylene, the olefin conversion (any described herein) can be an ethylene conversion.

In an aspect, the catalyst system productivity for the olefin oligomerization process can be any catalyst system productivity which provides a desirable olefin oligomer product. In an embodiment, the minimum catalyst system productivity can be $1 \times 10^3$ grams (g) olefin oligomer product/mmol transition metal of the transition metal complex; alternatively, $5 \times 10^3$ g olefin oligomer product/mmol transition metal of the transition metal complex; alternatively, $1 \times 10^4$ g olefin oligomer product/mmol transition metal of the transition metal complex; alternatively, $5 \times 10^4$ g olefin oligomer product/mmol transition metal of the transition metal complex; alternatively, $1 \times 10^5$ g olefin oligomer product/mmol transition metal of the transition metal complex; or alternatively, $5 \times 10^3$ g olefin oligomer product/mmol transition metal of the transition metal complex. In an embodiment, the maximum catalyst system productivity can be $1 \times 10^8$ g olefin oligomer product/mmol transition metal of the transition metal complex; alternatively, $5 \times 10^7$ g olefin oligomer product/mmol transition metal of the transition metal complex; alternatively, $1 \times 10^7$ g olefin oligomer product/mmol transition metal of the transition metal complex; alternatively, $5 \times 10^6$ g olefin oligomer product/mmol transition metal of the transition metal complex; or alternatively, $1 \times 10^6$ g olefin oligomer product/mmol transition metal of the transition metal complex. In some embodiments, the catalyst system productivity can range from any minimum catalyst system productivity described herein to any maximum catalyst system productivity described herein. For example, in some non-limiting embodiments, the catalyst system productivity can range from $1 \times 10^3$ to $1 \times 10^8$ g olefin oligomer product/mmol transition metal of the transition metal complex; alternatively, $5 \times 10^3$ to $5 \times 10^7$ g olefin oligomer product/mmol transition metal of the transition metal complex; alternatively, $5 \times 10^4$ to $5 \times 10^7$ g olefin oligomer product/mmol transition metal of the transition metal complex; or alternatively, $1 \times 10^5$ to $1 \times 10^7$ g olefin oligomer product/mmol transition metal of the transition metal complex. Other catalyst system productivities are readily apparent from the present disclosure. When a specific transition metal of the transition metal complex is utilized, the catalyst system productivity can be provided utilizing the specific transition metal; for example when an iron transition metal complex is utilized, the catalyst system productivity can be provided in units of g olefin oligomer product/mmol Fe.

In an aspect where the olefin consists essentially of ethylene, the oligomerization process can produce an alpha olefin product with high selectivity to linear alpha olefins; or alternatively, to normal alpha olefins. In some embodiments where the olefin consists essentially of ethylene, the oligomerization process can produce a reactor effluent wherein the $C_6$ olefin oligomer product has a 1-hexene content of at least 98.5 wt. %; alternatively, at least 98.75 wt. %; alternatively, at least 99.0 wt. %; or alternatively, at least 99.25 wt. %. In other embodiments where the olefin consists essentially of ethylene, the oligomerization process can produce a reactor effluent wherein the $C_8$ olefin oligomer product has a 1-octene content of at least 98 wt. %; alternatively, at least 98.25 wt. %; alternatively, at least 98.5 wt. %; alternatively, at least 98.75 wt. %; or alternatively, at least 99.0 wt. %. In yet other embodiments where the olefin consists essentially of ethylene, the oligomerization process can produce a reactor effluent wherein the $C_{10}$ olefin oligomer product has a 1-decene content of at least 97.5 wt. %; alternatively, at least 97.75 wt. %; alternatively, at least 98 wt. %; alternatively, at least 98.25 wt. %; or alternatively, at least 98.5 wt. %. In yet other embodiments where the olefin consists essentially of ethylene, the oligomerization process can produce a reactor effluent wherein the $C_{12}$ olefin oligomer product has a 1-dodecene content of at least 96.5 wt. %; alternatively, at least 97 wt. %; alternatively, at least 97.5 wt. %; alternatively, at least 97.75 wt. %; or alternatively, at least 98.0 wt. %. In yet other embodiments where the olefin consists essentially of ethylene, the oligomerization process can produce a reactor effluent wherein the oligomer product can comprise any combination of any $C_6$ olefin oligomer product 1-hexene content described herein, any $C_8$ olefin oligomer product 1-octene content described herein, any $C_{10}$ olefin oligomer product 1-decene content described herein, and/or any $C_8$ olefin oligomer product 1-octene content described herein. In some non-limiting examples where the olefin consists essentially of ethylene, the oligomerization process can produce a reactor effluent having a $C_6$ olefin oligomer product 1-hexene content of at least 99 wt. % and a $C_{12}$ olefin oligomer product 1-dodecene content of at least 97.5 wt. %; alternatively, a $C_8$ olefin oligomer product 1-octene content of at least 98.5 wt. % and a $C_{12}$ olefin oligomer product 1-dodecene octene content of at least 97.5 wt. %; or alternatively, a $C_6$ olefin oligomer product 1-hexene content of at least 99 wt. %, a $C_8$ olefin oligomer product 1-octene content of at least 98.5 wt. %, a $C_{10}$ olefin oligomer product 1-decene content of at least 98 wt. %, and a $C_{12}$ olefin oligomer product 1-dodecene content of at least 97.5 wt. %. Other combinations of olefin oligomer 1-alkene content are readily apparent from the present disclosure.

For many olefin oligomerizations, it has been established that the olefin oligomer product distribution K value (also known as the Schulz-Flory chain growth factor among other terms) for an olefin oligomerization using a particular catalyst system can be impacted by identity of the components of the catalyst system and the temperature utilized for the olefin oligomerization. It has now been unexpectedly discovered that the olefin oligomer product distribution K value for olefin oligomerization utilizing a catalyst system comprising, or consisting essentially of a transition metal complex comprising a transition metal compound complexed to a ligand comprising a pyridine bisimine group can be impacted by other olefin oligomerization parameters in addition to the identity of the components of the catalyst system at an olefin oligomerization temperature. For example, it has been unexpectedly discovered that the olefin oligomer product distribution K value for olefin oligomerization utilizing a catalyst system comprising, or consisting essentially of a transition metal complex comprising a transition metal compound complexed to a ligand comprising a pyridine bisimine group can be impacted by i) a transition metal of the transition metal complex concentration in the reactor, ii) a metal of the metal alkyl compound concentration in the reactor, and/or iii) a metal of the metal alkyl to transition metal of the transition metal complex molar ratio in the reactor. When the reactor is a continuous reactor, these features can be stated in terms of a continuous reactor.

In an aspect, the olefin oligomerization process comprising contacting an olefin and a catalyst system (alternatively, contacting an olefin, a transition metal complex, and a metal alkyl compound; or alternatively, contacting an olefin, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)), or alternatively, an olefin, hydrogen, and a catalyst system (alternatively, contacting an olefin, hydrogen a transition metal complex, and a metal alkyl compound; or alternatively, contacting an olefin, hydrogen, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)) to form an olefin oligomer product can also comprise controlling an olefin oligomer product distribution K value; or alternatively, controlling an olefin oligomer product distribution K value by adjusting an olefin oligomerization parameter. In another aspect, the olefin oligomerization process comprising contacting an olefin and a catalyst system (alternatively, contacting an olefin, a transition metal complex, and a metal alkyl compound; or alternatively, contacting an olefin, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)) or contacting an olefin, hydrogen, and a catalyst system (alternatively, contacting an olefin, hydrogen a transition metal complex, and a metal alkyl compound; or alternatively, contacting an olefin, hydrogen, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)) to form an olefin oligomer product can also comprise selecting an olefin oligomer product distribution K value and adjusting an olefin oligomerization parameter to obtain the selected olefin oligomer product distribution K value. In yet another aspect, the olefin oligomerization process comprising contacting an olefin and a catalyst system (alternatively, contacting an olefin, a transition metal complex, and a metal alkyl compound; or alternatively, contacting an olefin, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)) or contacting an olefin, hydrogen, and a catalyst system (alternatively, contacting an olefin, hydrogen a transition metal complex, and a metal alkyl compound; or alternatively, contacting an olefin, hydrogen, a transition metal complex, and a Lewis acid capable of abstracting capable of abstracting an anionic specie, a hydride, or an alkyl group (or a Lewis acid and an agent capable of alkylating the transition metal complex and/or adding a hydride anion to the transition metal complex)) to form an olefin oligomer product can also comprise correlating an olefin oligomer product distribution with an olefin oligomerization parameter; alternatively, correlating an olefin oligomer product distribution with an olefin oligomerization parameter and selecting an olefin oligomer product distribution K value and oligomerizing the olefin at the selected olefin oligomer product distribution K value by setting the olefin oligomerization parameters necessary to achieve the selected olefin oligomer product distribution K value.

In an embodiment, the olefin oligomerization parameter which can be correlated with an olefin oligomer product distribution K value, adjusted, adjusted to control an olefin oligomer product distribution K value, or adjusted to obtain a selected olefin oligomer product distribution K value can be selected from i) a transition metal of the transition metal complex concentration in the reactor, ii) a metal of the metal alkyl concentration in the reactor, iii) a metal of the metal alkyl to transition metal of the transition metal complex molar ratio in the reactor, and iv) any combination thereof. In other embodiments, the olefin oligomerization parameter which can be correlated with an olefin oligomer product distribution K value, adjusted, adjusted to control an olefin oligomer product distribution K value, adjusted to obtain a selected olefin oligomer product distribution K value can be the transition metal of the transition metal complex concentration in the reactor; alternatively, the metal of the metal alkyl concentration in the reactor; alternatively, the metal of the metal alkyl to transition metal of the transition metal complex molar ratio in the reactor; alternatively, i) the transition metal of the transition metal complex concentration in the reactor and ii) the metal of the metal alkyl concentration in the reactor; alternatively, i) the transition metal of the transition metal complex concentration in the reactor and ii) the metal of the metal alkyl to transition metal of the transition metal complex molar ratio in the reactor; alternatively, i) the metal of the metal alkyl concentration in the reactor and ii) the metal of the metal alkyl to transition metal of the transition metal complex molar ratio in the reactor; or alternatively, i) the transition metal of the transition metal complex concentration in the reactor, ii) the metal of the metal alkyl concentration in the reactor, and iii) the metal of the metal alkyl to transition metal of the transition metal complex molar ratio in the reactor.

It should be noted that temperature can also impact the olefin oligomer product distribution. Consequently, any correlation of the olefin oligomer product distribution K value with i) the transition metal of the transition metal complex concentration in the reactor, ii) a metal of the metal alkyl concentration in the reactor, and/or iii) a metal of the metal alkyl to transition metal of the transition metal complex molar ratio in the reactor should hold the temperature as a constant. However, multiple correlations at a constant temperature can be made with i) the transition metal of the transition metal complex concentration in the reactor, ii) a metal of the metal alkyl concentration in the reactor, and/or iii) a metal of the metal alkyl to transition metal of the transition metal complex molar ratio to further correlate the affect that temperature has on the olefin oligomer product distribution K value. Alternatively, a correlation of the olefin oligomer product distribution K value with temperature and i) the transition metal of the transition metal complex concentration in the reactor, ii) a metal of the metal alkyl concentration in the reactor, and/or iii) a metal of the metal alkyl to transition metal of the transition metal complex molar ratio in the reactor can be made. In terms of an olefin oligomerization process, it should noted that an adjustment of one or more of i) the transition metal of the transition metal complex concentration in the reactor, ii) a metal of the metal alkyl concentration in the reactor, and/or iii) a metal of the metal alkyl to transition metal of the transition metal complex molar ratio in the reactor does not preclude the possibility of also adjusting the temperature to achieve further olefin oligomerization objectives (e.g., improved product purity, or improved process temperature control, improved catalyst system stability, or improved catalyst system productivity, among other feature). In some embodiments, the olefin oligomerization parameters selected from i) the transition metal of the transition metal complex concentration in the reactor, ii) the metal of the metal alkyl concentration in the reactor, iii) the metal of the metal alkyl to transition metal of the transition metal complex molar ratio in the reactor, and iv) any combination thereof are adjusted while other parameters of the olefin oligomerization which can affect the K value are held constant.

Generally, the olefin oligomer product distribution K value, the transition metal of the transition metal complex concentration in the reactor, the metal of the metal alkyl concentration in the reactor, and the metal of the metal alkyl to transition metal of the transition metal complex molar ratio in the reactor are independent elements of any olefin oligomerization process described herein Consequently, the olefin oligomerization process can be further described utilizing any olefin oligomer product distribution K value (or value range) described herein, any transition metal of the transition metal complex concentration in the reactor described herein, any metal of the metal alkyl concentration in the reactor described herein, and any metal of the metal alkyl to transition metal of the transition metal complex molar ratio in the reactor described herein.

In embodiments, the olefin oligomer product distribution K value can have a minimum value of (or can be at least) 0.4; alternatively, 0.45; alternatively, 0.5; alternatively, 0.55; alternatively, 0.6; alternatively, 0.65; alternatively, 0.7; alternatively, 0.75; or alternatively, 0.8. In an embodiment, the olefin oligomer product distribution K value can have a maximum value of 0.9; alternatively, 0.85; alternatively, 0.8; alternatively, 0.75; alternatively, 0.7; or alternatively, 0.6; or alternatively. In an embodiment, the olefin oligomer product distribution K value can have a range from any minimum olefin oligomer product distribution K value disclosed herein to any maximum olefin oligomer product distribution K value disclosed herein. For example, in some non-limiting embodiments, the olefin oligomer product distribution K value can range from 0.4 to 0.9; alternatively, from 0.4 to 0.8; alternatively, from 0.5 to 0.8; alternatively, from 0.5 to 0.7; alternatively, from 0.55 to 0.7. Other olefin oligomer product distribution K value ranges are readily apparent from the present disclosure.

The olefin oligomer product distribution K value (sometimes referred to as Schulz-Flory chain growth factor, K) can be defined the equation: $K=X_{q+1}/X_q$ wherein $X_{q+1}$ is the number of moles of olefin oligomer product produced having q+1 olefin units and $X_q$ is the number of moles of olefin oligomer product produced having q olefin units). Generally, the olefin oligomer product distribution K value can be determined using any two olefin oligomers of the olefin oligomer product which differs in the number of monomer units by 1. However, one would appreciate that product isolation and analysis can lead to inaccuracies in a determined olefin oligomer product distribution using particular olefin oligomers (e.g., incomplete recovery of gaseous product and/or solid product during product isolation). One having ordinary skill in the art would recognize such issues and can choose the appropriate oligomers upon which to base the determination of the olefin oligomer product distribution K value.

In an embodiment, the olefin oligomer product distribution K value can be determined using the olefin oligomer product containing four and five olefin units; alternatively, five and six olefin units; alternatively, six and seven olefin units; or alternatively, seven and eight olefin units. In some embodiments where the olefin is ethylene, the olefin oligomer product distribution K value can be determined using $C_8$ and $C_{10}$ olefin oligomer product; alternatively, using $C_{10}$ and $C_{12}$ olefin oligomer product; alternatively, using $C_{12}$ and $C_{14}$ olefin oligomer product; or alternatively, $C_{14}$ and $C_{16}$ olefin oligomer product. In an embodiment, olefin oligomer product distribution K values can be an average of any two or more olefin oligomer product distribution K values using different adjacent pairs of produced olefin oligomers described herein. In some embodiments, the olefin oligomer product distribution K value can be an average of any two olefin oligomer product distribution K values described herein; alternatively, any three olefin oligomer product distribution K values described herein; or alternatively, any three olefin oligomer product distribution K values described herein.

In an aspect, a transition metal of the transition metal complex concentration in the reactor can have any value useful to produce a desired olefin oligomer product and/or olefin oligomer product distribution. In some embodiments, the minimum transition metal of the transition metal complex concentration in the reactor can be $1.0\times10^{-6}$ mole of transition metal per kilogram olefin oligomerization solution; alternatively, $5.0\times10^{-6}$ mole of transition metal per kilogram olefin oligomerization solution; alternatively, $1.0\times10^{-5}$ mole of transition metal per kilogram olefin oligomerization solution; alternatively, $5.0\times10^{-5}$ mole of transition metal per kilogram olefin oligomerization solution; alternatively, $1.0\times10^{4}$ mole of transition metal per kilogram olefin oligomerization solution; alternatively, $5.0\times10^{4}$ mole of transition metal per kilogram olefin oligomerization solution; alternatively, $1.0\times10^{-3}$ mole of transition metal per kilogram olefin oligomerization solution; or alternatively, $5.0\times10^{-3}$ mole of transition metal per kilogram olefin oligomerization solution. In some embodiments, the maximum transition metal of the transition metal complex concentration in the reactor can be $5.0\times10^{-1}$ mole of transition metal per kilogram olefin oligomerization solution; alternatively, $1.0\times10^{-1}$ mole of transition metal per kilogram olefin oligomerization solution; alternatively, $5.0\times10^{-2}$ mole of transition metal per kilogram olefin oligomerization solution; alternatively, $1.0\times10^{-2}$ mole of transition metal per kilogram olefin oligomerization solution; alternatively, $5.0\times10^{-3}$ mole of transition metal per kilogram olefin oligomerization solution; alternatively, $1.0\times10^{-3}$ mole of transition metal per kilogram olefin oligomerization solution; alternatively, $5.0\times10^{4}$ mole of transition metal per kilogram olefin oligomerization solution; or alternatively, $1.0\times10^{-4}$ mole of transition metal per kilogram olefin oligomerization solution. In other embodiments, the transition metal of the transition metal complex concentration in the reactor can range from any minimum transition metal of the transition metal complex concentration in the reactor provided herein to any maximum transition metal of the transition metal complex concentration in the reactor provided herein. For example, in some non-limiting embodiments, the transition metal of the transition metal complex concentration in the reactor can range from $1.0\times10^{-6}$ to $5.0\times10^{-1}$ mole of transition metal per kilogram olefin oligomerization solution; alternatively, $1.0\times10^{-5}$ to $1.0\times10^{-1}$ mole of transition metal per kilogram olefin oligomerization solution; alternatively, $5.0\times10^{-5}$ to $5.0\times10^{-2}$ mole of transition metal per kilogram olefin oligomerization solution; or alternatively, $1.0\times10^{-5}$ to $1.0\times10^{-2}$ mole of transition metal per kilogram olefin oligomerization solution. Other transition metal of the transition metal complex concentrations in the reactor are readily apparent from the present disclosure. When a specific transition metal of the transition metal complex is utilized, the transition metal of the transition metal complex concentration in the reactor can be provided utilizing the specific transition metal; for example when a iron transition metal complex is utilized, the transition metal of the transition metal complex concentration in the reactor can be provided in units of mole of Fe per kilogram olefin oligomerization solution.

In an aspect, a metal of the metal alkyl compound concentration in the reactor can have any value useful to produce a desired olefin oligomer product and/or olefin oligomer product distribution. In some embodiments, the minimum metal of the metal alkyl compound concentration in the reactor can be $1.0\times10^{-3}$ mole of metal per kilogram olefin oligomerization solution; alternatively, $5.0\times10^{-3}$ mole of metal per kilogram olefin oligomerization solution; alternatively, $1.0\times10^{-2}$ mole of metal per kilogram olefin oligomerization solution; alternatively, $5.0\times10^{-2}$ mole of metal per kilogram olefin oligomerization solution; alternatively, $1.0\times10^{-1}$ mole of metal per kilogram olefin oligomerization solution; alternatively, $5.0\times10^{-1}$ mole of metal per kilogram olefin oligomerization solution; alternatively, $1.0\times10^{2}$ mole of metal per kilogram olefin oligomerization solution; or alternatively, $5.0\times10^{0}$ mole of metal per kilogram olefin oligomerization solution. In some embodiments, the maximum metal of the metal alkyl compound concentration in the reactor can be $1.0\times10^{3}$ mole of metal per kilogram olefin oligomerization solution; alternatively, $5.0\times10^{2}$ mole of metal per kilogram olefin oligomerization solution; alternatively, $1.0\times10^{2}$ mole of metal per kilogram olefin oligomerization solution; alternatively, $5.0\times10^{1}$ mole of metal per kilogram olefin oligomerization solution; alternatively, $1.0\times10^{1}$ mole of metal per kilogram olefin oligomerization solution; alternatively, $5.0\times10^{0}$ mole of metal per kilogram olefin oligomerization solution; or alternatively, $1.0\times10^{0}$ mole of metal per kilogram olefin oligomerization solution. In other embodiments, the metal alkyl compound concentration in the reactor can range from any minimum metal alkyl compound concentration in the reactor provided herein to any maximum metal alkyl compound concentration in the reactor provided herein. For example, in some non-limiting embodiments, the metal of the metal alkyl compound concentration in the reactor can range from $5.0\times10^{-3}$ to $1.0\times10^{3}$ mole of metal per kilogram olefin oligomerization solution; alternatively, $1.0\times10^{-3}$ to $5.0\times10^{2}$ mole of metal per kilogram olefin oligomerization solution; alternatively, $5.0\times10^{-2}$ to $1.0\times10^{1}$ mole of metal per kilogram olefin oligomerization solution; or alternatively, $1.0\times10^{-1}$ to $5.0\times10^{0}$ mole of metal per kilogram olefin oligomerization solution. Other metal of the metal alkyl compound concentrations in the reactor are readily apparent from the present disclosure. When a specific metal of the metal alkyl compound is utilized, the metal of the metal alkyl compound concentration in the reactor can be provided utilizing the specific metal; for example when an aluminum alkyl compound is utilized, the metal of the metal alkyl compound concentration in the reactor can be provided in units of mole of Al per kilogram olefin oligomerization solution.

In an aspect, the metal of the metal alkyl to transition metal of the transition metal complex molar ratio in the reactor can have any value useful to produce a desired olefin oligomer product and/or olefin oligomer product distribution. Catalyst system metal of the metal alkyl to transition metal of the transition metal complex molar ratios are independently described herein. These independently described metal of the metal alkyl to transition metal of the transition metal complex molar ratios can be utilized without limitation to further describe an olefin oligomerization process described herein. When a specific metal of the metal alkyl compound and a specific transition metal of the transition metal complex are utilized, the metal of the metal alkyl compound to transition metal of the transition metal complex molar ratio can be provided utilizing the specific metal of the metal alkyl compound and transition of the transition metal compound; for example when an aluminum alkyl compound and iron complex are utilized, the metal of the metal alkyl compound to transition metal of the transition metal complex can be provided as an Al:Fe molar ratio.

It has further been unexpectedly discovered that when the olefin oligomerization is carried out in a continuous reactor, the olefin oligomer product can be formed at a temperature higher than possible when the olefin oligomerization is practiced in a batch reactor. In an embodiment, the olefin oligomerization process can comprise a) contacting an olefin and a catalyst system comprising i) a transition metal complex comprising a transition metal compound complexed to a ligand comprising a pyridine bisimine group, and ii) a metal alkyl compound, and b) forming an olefin oligomer product in a continuous reactor at any olefin oligomerization temperature of at least 95° C. In other embodiments, the olefin oligomer product can be formed in a continuous reactor at any olefin oligomerization temperature described herein or olefin oligomerization temperature range described herein with a temperature of at least 95° C. Other aspects and embodiments of the olefin oligomerization process are independently described herein and can be utilized, without limitation to further describe the olefin oligomerization carried out in a continuous reactor where the olefin oligomer product is produced at an olefin oligomerization temperature of (or olefin oligomerization temperature range with a temperature of) at least 95° C.

In an embodiment the olefin oligomerization reaction can be carried out using a continuous reactor wherein the variance of the concentration of the olefin (over the oligomerization time or average oligomerization time) at any point in the reactor can be less than 1 wt. %, 0.8 wt. %, 0.7 wt. %, 0.6 wt. %, 0.5 wt. %, less than 0.4 wt. %, less than 0.3 wt. %, less than 0.2 wt. %, or less than 0.1 wt. %.

Any suitable methodology or technique can be employed to maintain the variance in olefin concentration to within the disclosed ranges. In an embodiment, the variation in olefin concentration can be maintained within the disclosed ranges through the use of one or more reactors comprising an injection port configured to supply additional amounts of olefin to the reactor during the oligomerization of the olefin. The injection port can be in fluid communication with one or more controllers which function, in addition to controlling the operation of the injection port, to monitor one or more conditions of the reactions that correlate to the olefin concentration present during the oligomerization process. In one embodiment, the controller can detect an olefin concentration variance that approaches but is not outside of the olefin concentration variances disclosed herein. The controller can then implement one or more commands to ensure the olefin concentration remains within the concentration variances disclosed herein. For example and with reference to FIG. 3, in an ethylene oligomerization process, ethylene can be introduced to a continuous stirred tank reactor 50 through injection port 40 which can be in fluid communication with controller 15. Upon detection of an ethylene concentration approaching a value outside of the concentration variances disclosed herein, the controller can implement one or more functions to introduce additional amounts of ethylene to the reactor and result in maintenance of the ethylene concentration within the disclosed concentration variances.

In an alternative embodiment, the variation in olefin concentration can be maintained within the disclosed ranges through the use of one or more reactors comprising a plurality of injection ports disposed throughout the reactor that can be utilized to introduce additional amounts of olefin to the continuous process that result in maintenance of the olefin concentration within the disclosed variances.

The processes described herein can utilize one or more solvents and/or diluents. Solvents and or/diluents which can be utilized in aspects of the present disclosure include without limitation water, hydrocarbons, halogenated hydrocarbons, ethers, carbonates, esters, ketones, aldehydes, alcohols, nitriles and combinations thereof. In some embodiments, an aspect of the invention can call for a polar solvent (and/or diluent). Polar solvents (and/or diluents) which can be utilized include, without limitation, water ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. In some embodiments, an aspect of the invention can call for an aprotic polar solvent (and/or diluent). Aprotic polar solvents (and/or diluents) which can be utilized include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. In other embodiments, an aspect of the disclosure can call for a non-polar solvent (and/or diluent). Non-polar solvents (and/or diluents) include without limitation hydrocarbons, halogenated hydrocarbons, or mixtures thereof; alternatively, a hydrocarbon; or alternatively, a halogenated hydrocarbon. In another embodiment, an aspect of the present disclosure can call for a solvent (and/or diluent) that is substantially unreactive with a metal alkyl. Solvents (and/or diluents) which are unreactive with a metal alkyl include without limitation ethers, hydrocarbons, and mixtures thereof; alternatively, ethers; or alternatively, hydrocarbons.

Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively, aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent (and/or diluent) include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents (and/or diluents) that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents (and/or diluents) include cyclohexane, methyl cyclohexane; alternatively, cyclohexane; or alternatively, methylcyclohexane. Aromatic hydrocarbons which can be useful as a solvent (and/or diluent) include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent (and/or diluent) include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent (and/or diluent) include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively, chlorobenzene and dichlorobenzene.

Ethers, carbonates, esters, ketones, aldehydes, or alcohols which can be useful as a solvent (and/or diluent) include $C_2$ to $C_{20}$ ethers, carbonates, esters, ketones, aldehydes, or alcohols; alternatively, $C_2$ to $C_{10}$ ethers, carbonates, esters, ketones, aldehydes, or alcohols; or alternatively, $C_2$ to $C_5$ ethers, carbonates, esters, ketones, aldehydes, or alcohols. Suitable ether solvents (and/or diluents) can be cyclic or acyclic. Non-limiting examples of suitable ethers which can be useful as a solvent (and/or diluent) include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent group are disclosed herein and can be utilized without limitation of further describe the substituted tetrahydrofuran, dihydrofuran, furan, 1,3-dioxane, or 1,4 dioxane solvents (and/or diluents). Non-limiting examples of suitable carbonates which can be utilized as a solvent (and/or diluent) include ethylene carbonate, propylene carbonate, diethyl carbonate, diethyl carbonate, glycerol carbonate, and combinations thereof. Non-limiting examples of suitable esters which can be utilized as a solvent (and/or diluent) include ethyl acetate, propyl acetate, butyl acetate, isobutyl isobutyrate, methyl lactate, ethyl lactate, and combinations thereof. Non-limiting examples of suitable ketones which can be utilized as a (and/or diluent) include acetone, ethyl methyl ketone, methyl isobutyl ketone, and combinations thereof. Non-limiting examples of suitable alcohols which can be utilized as a solvent (and/or diluent) include methanol, ethanol, propanol, isopropanol, n-butanol, isobutanol, pentanol, hexanol, heptanol, octanol, benzyl alcohol, phenol, cyclohexanol, and the like, or combinations thereof.

Various aspects and embodiments described herein refer to non-hydrogen substituents such as halogen (or halo, halide), hydrocarbyl, hydrocarboxy, alkyl, and/or alkoxy substituents, among others. The non-hydrogen substituents of any aspect or any embodiment calling for a substituent can be a halide, a $C_1$ to $C_{10}$ hydrocarbyl group, a $C_1$ to $C_{10}$ halogenated hydrocarbyl group, a $C_1$ to $C_{10}$ hydrocarboxy group, or a $C_1$ to $C_{20}$ trihydrocarbylsiloxy group; alternatively, a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; alternatively, a $C_1$ to $C_{10}$ halogenated hydrocarbyl group; alternatively, a $C_1$ to $C_{10}$ hydrocarboxy group; or alternatively, a $C_1$ to $C_{20}$ trihydrocarbylsiloxy group. In other embodiments, the non-hydrogen substituents of any aspect or any embodiment calling for a substituent can be a halide, a $C_1$ to $C_5$ hydrocarbyl group, a $C_1$ to $C_5$ halogenated hydrocarbyl group, a $C_1$ to $C_5$ hydrocarboxy group, or a $C_1$ to $C_{10}$ trihydrocarbylsiloxy group; alternatively, halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; alternatively, a $C_1$ to $C_5$ halogenated hydrocarbyl group; alternatively, a $C_1$ to $C_5$ hydrocarboxy group; or alternatively, a $C_1$ to $C_{10}$ trihydrocarbylsiloxy group.

In an embodiment, any halide substituent of any aspect or any embodiment calling for a substituent can be a fluoride, chloride, bromide, or iodide; alternatively, a fluoride or chloride. In some embodiments, any halide substituent of any aspect or any embodiment calling for a substituent can be a fluoride; alternatively, a chloride; alternatively, a bromide; or alternatively, an iodide.

In an embodiment, any hydrocarbyl substituent can be an alkyl group, an aryl group, or an aralkyl group; alternatively, an alkyl group; alternatively, an aryl group; or alternatively, an aralkyl group. Generally, the alkyl substituent group(s), the aryl substituent group(s), and/or an aralkyl substituent group(s) can have the same number of carbon atoms of the hydrocarbyl substituent group disclosed herein. In an embodiment, any alkyl substituent of any aspect or any embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or any embodiment calling for a substituent can be phenyl group, a tolyl group, a xylyl group, or a 2,4,6-trimethylphenyl group; alternatively, a phenyl group; alternatively, a tolyl group; alternatively, a xylyl group; alternatively, a 2,4,6-trimethylphenyl group; or alternatively, a tert-butylphenyl group (e.g., a 4-tert-butylphenyl group, among others). In an embodiment, each tolyl group which can be utilized as an aryl substituent independently can be a 2-methylphenyl group, a 3-methylphenyl group, or a 4-methyl phenyl group; alternatively, a 2-methylphenyl group; alternatively, a 3-methylphenyl group; or alternatively, a 4-methyl phenyl group. In an embodiment, each xylyl group which can be utilized as an aryl substituent independently can be a 2,3-dimethyl phenyl group, a 2,4-dimethylphenyl group, a 2,5-dimethyl phenyl group, a 2,6-dimethyl phenyl group, a 3,4-dimethyl phenyl group, or a 3,5-dimethyl phenyl group; alternatively, a 2,4-dimethylphenyl group or a 2,6-dimethyl phenyl group; alternatively, a 2,3-dimethyl phenyl group; alternatively, a 2,4-dimethylphenyl group; alternatively, a 2,5-dimethyl phenyl group; alternatively, a 2,6-dimethyl phenyl group; alternatively, a 3,4-dimethyl phenyl group; or alternatively, a 3,5-dimethyl phenyl group. In an embodiment, any aralkyl substituent of any aspect or any embodiment calling for a substituent can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an embodiment, any halogenated hydrocarbyl substituent can be a halogenated alkyl group, a halogenated aryl group, or a halogenated aralkyl group; alternatively, a halogenated alkyl group; alternatively, a halogenated aryl group; or alternatively, a halogenated aralkyl group. Generally, the halogenated alkyl substituent group(s), the halogenated aryl substituent group(s), and/or the halogenated aralkyl substituent group(s) can have the same number of carbon atoms of the halogenated hydrocarbyl substituent group disclosed herein. The halogenated alkyl substituent group(s), the halogenated aryl substituent group(s), and/or the halogenated aralkyl substituent group(s) can described utilizing any combination of the alkyl, aryl, or aralkyl substituents described herein and the halide substituent described herein. In some embodiments, any halogenated hydrocarbyl substituent of any aspect or any embodiment calling for a substituent can be a trifluoromethyl group.

In an embodiment, any hydrocarboxy substituent of any aspect or any embodiment calling for a substituent can be an alkoxy group, an aryloxy group, or an aralkoxy group; alternatively, an alkoxy group; alternatively, an aryloxy group; or alternatively, an aralkoxy group. Generally, the alkoxy substituent group(s), the aroxy substituent group(s), and/or an aralkoxy substituent group(s) can have the same number of carbon atoms of the hydrocarboxy substituent group disclosed herein. In an embodiment, any alkoxy substituent of any aspect or any embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or any embodiment calling for a substituent can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, any aralkoxy substituent of any aspect or any embodiment calling for a substituent can be benzoxy group.

In an embodiment, each hydrocarbyl group of any trihydrocarbylsiloxy substituent independently can be any hydrocarbyl substituent described herein (e.g., any general or specific alkyl group, aryl group, or aralkyl group described herein). In some embodiments, each trihydrocarbylsiloxy substituent independently can be a trialkylsiloxy group or a triarylsiloxy group; alternatively, a trialkylsiloxy group; or alternatively, a triarylsiloxy group. In some embodiments, each trihydrocarbylsiloxy substituent independently can be a trimethylsiloxy group, a triethylsiloxy, group, a tripropylsiloxy group, or a triphenylsiloxy group; alternatively, a trimethylsiloxy group, a triethylsiloxy, group, or a tripropylsiloxy group; or alternatively, a trimethylsiloxy group or a triphenylsiloxy group; alternatively, a trimethylsiloxy group; alternatively, a triethylsiloxy group; alternatively, a tripropylsiloxy group; or alternatively, a triphenylsiloxy group.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and olefin oligomerization and/or olefin polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES

All operations were performed in an oxygen free and moisture free environment. Solvents were dried over 13× molecular sieves, and ethylene was purified using in-stream de-oxygenation and moisture removal beds. MMAO 3A was purchased from Akzo Nobel. Ethylene oligomerizations were performed using the apparatus shown in FIG. 3 using Complex 1 which was prepared according to methods described in the literature (e.g., U.S. Pat. No. 6,710,006).

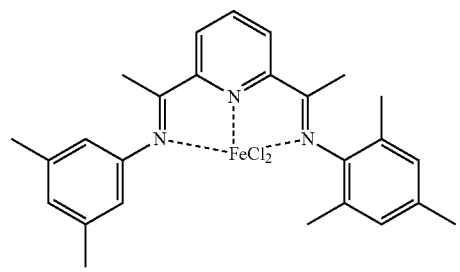

Figure 3:
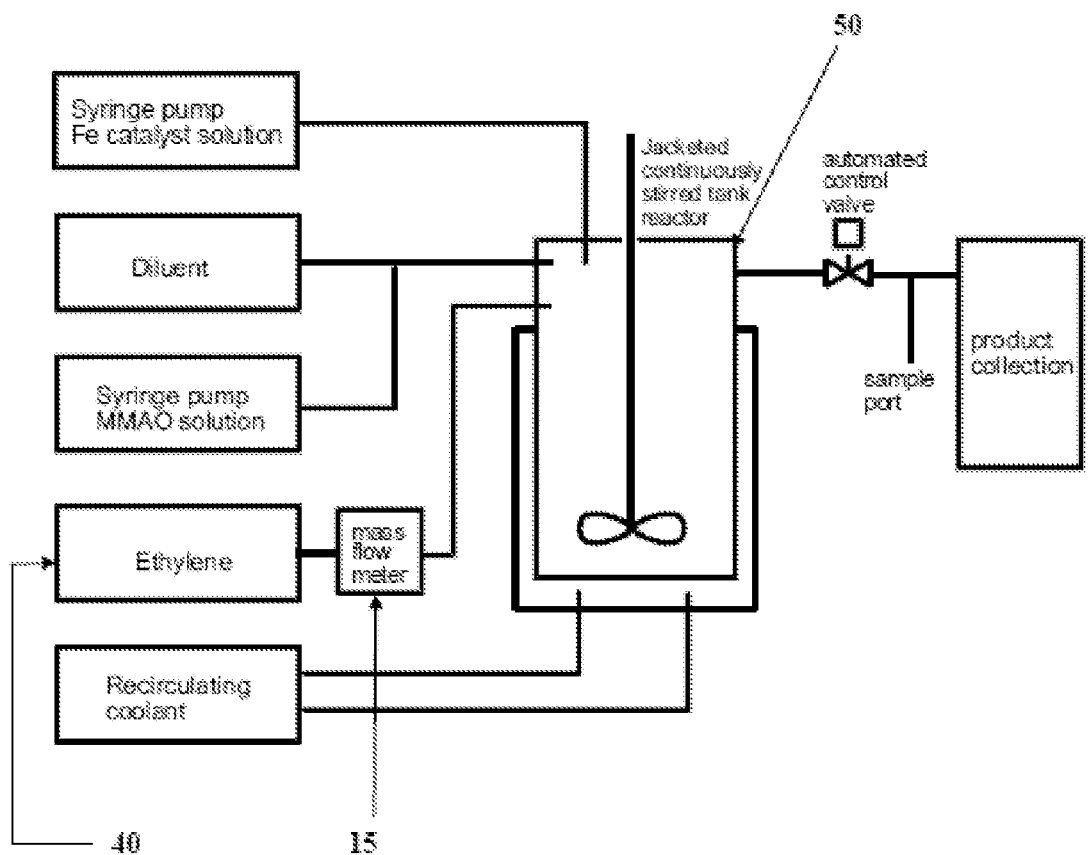
FIG. 3 provides a diagram of the experimental olefin oligomerization apparatus.

The Fe catalyst and MMAO cocatalyst solutions were prepared, and transferred under inert conditions to the appropriate syringe pumps shown in FIG. 3. Cyclohexane diluent was transferred from a circulating drier bed to the diluent reservoir, which was on a scale. Coolant flow at the proper temperature for maintaining the correct reactor temperature was established. Diluent was pumped continuously from the diluent reservoir to the reactor, and once the reactor was full and had reached the run pressure (1200 psig), the ethylene, catalyst, and cocatalyst flows were started. Reactor pressure was maintained at 1200 psig in all experiments by use of the automated control valve. Once steady state conditions were established in the reactor, samples were analyzed for the properties shown in Table 1. The notes for Table 1 provide more details about the reactor conditions. Once steady state ("line-out") conditions had been reached, at least three samples were analyzed before changing reaction conditions.

The data in Table 1 show that the ethylene oligomer product distribution K value can be controlled by adjusting an ethylene oligomerization parameter, such as i) the iron of the iron complex concentration in the continuous reactor; ii) the aluminum of the aluminoxane concentration in the continuous reactor; iii) the aluminum of the aluminoxane to iron of the iron complex molar ratio in the continuous reactor; or iv) any combination of these ethylene oligomerization parameters.

FIG. 1 provides a graph showing the relationship between the aluminum of the aluminoxane concentration in the continuous reactor and the ethylene oligomer product distribution K value at an aluminum of the aluminoxane to iron of the iron complex molar ratio of approximately 1000. This graph shows that the ethylene oligomer product distribution K value can be controlled by adjusting the aluminum of the aluminoxane concentration in the continuous reactor of an ethylene oligomerization using catalyst system comprising a Fe pyridine bisimine complex.

Figure 2:
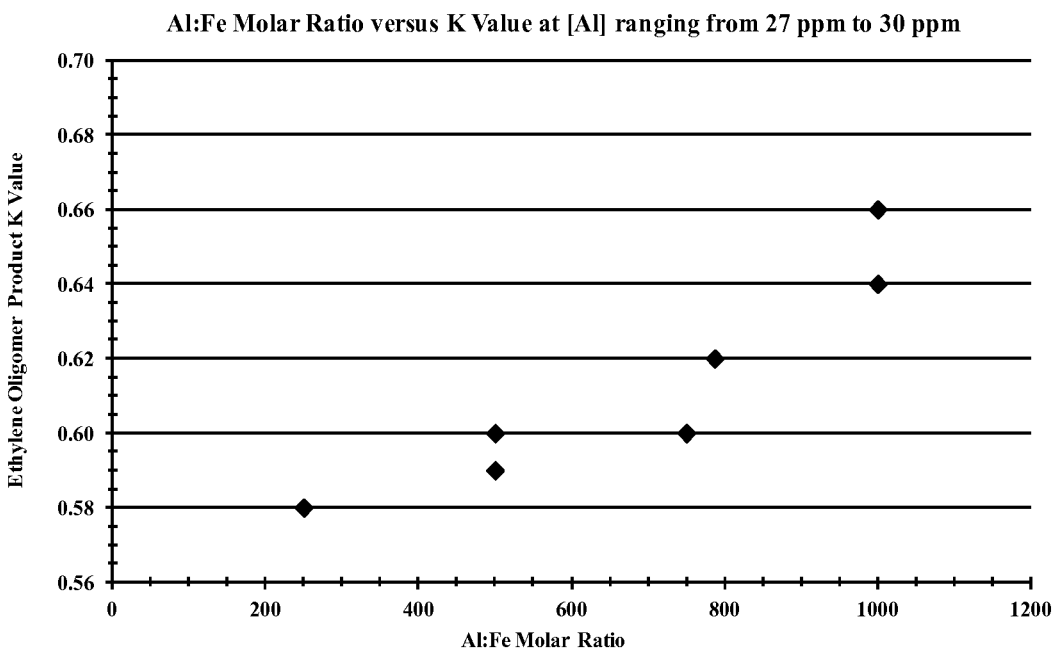
FIG. 2 provides a graph showing the relationship between the aluminum of the aluminoxane to iron of the iron complex molar ratio and the ethylene oligomer product distribution.

FIG. 2 provides a graph showing the relationship between the aluminum of the aluminoxane to iron of the iron complex molar ratio in the continuous reactor and the ethylene oligomer product distribution at an aluminum of the aluminoxane concentration ranging from 26 ppm to 30 ppm. This graph shows that the ethylene oligomer product distribution K value can be controlled by adjusting the aluminum of the aluminoxane to iron of the iron complex molar ratio in the continuous reactor of an ethylene oligomerization using catalyst system comprising a Fe pyridine bisimine complex.

TABLE 1

Ethylene Olefin Oligomerization Runs

| | Complex 1 Solution[a, b] | | | MMAO 3A Solution[c] | | Al:Fe | | |
|---|---|---|---|---|---|---|---|---|
| Entry | mg Fe Complex/h | g Fe Complex solution/h | μmol Fe/L-h) | g MMAO solution/h | mmol Al/L-h) | molar ratio | g dil/h[d] | g $C_2$/h[e] |
| 1 | 0.60 | 3.18 | 3.44 | 3.42 | 3.44 | 1000 | 410 | 310 |
| 2 | 0.30 | 1.59 | 1.72 | 1.71 | 1.72 | 1000 | 451 | 370 |
| 3 | 0.61 | 3.18 | 3.49 | 3.42 | 3.44 | 984 | 389 | 420 |
| 4 | 0.61 | 3.18 | 3.49 | 3.08 | 3.10 | 886 | 389 | 420 |
| 5 | 0.61 | 3.18 | 3.49 | 2.74 | 2.75 | 787 | 389 | 420 |
| 6 | 0.50 | 10.71 | 2.86 | 3.08 | 2.86 | 1000 | 364 | 420 |
| 7 | 0.67 | 5.35 | 3.84 | 3.08 | 2.88 | 750 | 364 | 420 |
| 8 | 1.00 | 3.56 | 5.73 | 3.08 | 2.86 | 500 | 364 | 420 |
| 9 | 2.00 | 2.68 | 11.45 | 3.08 | 2.86 | 250 | 364 | 420 |
| 10 | 0.80 | 4.17 | 4.58 | 2.46 | 2.29 | 500 | 364 | 330 |
| 11 | 0.40 | 2.09 | 2.29 | 2.46 | 2.29 | 1000 | 364 | 330 |

| Entry | Wt. % $C_2$ in feed | ppm Al in feed | Reactor WHSV (kg/L-h)[g] | Temp. (° C.) | $C_2$ Conv. (wt. %) | K value ($C_{12}/C_{10}$) | Productivity (g/mmol Fe) |
|---|---|---|---|---|---|---|---|
| 1 | 42.7 | 38.3 | 2.42 | 108 | 74 | 0.59 | 222,518 |
| 2 | 44.9 | 16.9 | 2.75 | 105 | 71 | 0.66 | 509,638 |
| 3 | 51.5 | 34.2 | 2.72 | 111 | 66 | 0.58 | 264,476 |
| 4 | 51.5 | 30.8 | 2.72 | 112 | 66 | 0.59 | 264,476 |
| 5 | 51.5 | 27.3 | 2.72 | 112 | 61 | 0.62 | 244,440 |
| 6 | 52.6 | 29.1 | 2.66 | 112 | 61 | 0.64 | 298,217 |
| 7 | 53.0 | 29.4 | 2.64 | 107 | 61 | 0.60 | 222,550 |
| 8 | 53.1 | 29.3 | 2.64 | 104 | 60 | 0.59 | 146,664 |
| 9 | 53.2 | 29.4 | 2.63 | 99 | 52 | 0.58 | 63,554 |
| 10 | 47.1 | 26.5 | 2.34 | 107 | 76 | 0.60 | 182,457 |
| 11 | 47.2 | 26.6 | 2.33 | 109 | 60 | 0.66 | 288,090 |

[a]Complex 1 solution was prepared in methylene chloride to a concentration of 0.25 mg of the iron complex/ml methylene chloride.
[b]Calculations based upon weight assumed one equivalent of THF per molecule of Fe complex.
[c]MMAO 3A solutions were prepared as ~0.7 wt. % Al in heptane.
[d]The diluent was cyclohexane.
[e]Ethylene flow was measured by a coriolis mass flow meter
[f]Temperatures, flow rates, WHSVs, ethylene oligomer distribution K values, ethylene oligomerization productivities, and ethylene conversions were determined as an average of at least 3 readings taken under reactor steady state conditions.
[g]WHSV = kg total feed to the reactor per L of reactor volume per hour.

We claim:

1. An olefin oligomerization process comprising:
   a) contacting an olefin and a catalyst system comprising
      i) a transition metal complex comprising an iron compound complexed to a ligand comprising a pyridine bisimine group, and
      ii) a metal alkyl compound
   to form an olefin oligomer product in a continuous reactor, wherein the contacting is carried out at a temperature ranging from 90° C. to 150° C. with a catalyst productivity of greater than $1\times10^5$ g olefin oligomer product/mmol iron of the transition metal complex; and
  b) controlling, in the continuous reactor, an olefin oligomer product distribution K value in a range from 0.5 to 0.8 for the transition metal complex by adjusting an olefin oligomerization parameter selected from
    i) iron of the transition metal complex concentration in the continuous reactor,
    ii) a metal of the metal alkyl compound concentration in the continuous reactor,
    iii) a metal of the metal alkyl to iron of the transition metal complex molar ratio in the continuous reactor of greater than 250:1, or
    iv) any combination thereof.

2. The process of claim 1, wherein the iron compound comprises a halide, nitrate, sulfate, phosphate, halate, hydrocarboxide, carboxylate, or β-dionate and the metal alkyl compound comprises an aluminoxane.

3. The process of claim 2, wherein the olefin, the transition metal complex, and the aluminoxane are simultaneously introduced into the continuous reactor.

4. The process of claim 1, wherein the olefin oligomer product distribution K value for the transition metal complex is controlled by adjusting an olefin oligomerization parameter selected from
  i) the iron of the transition metal complex concentration in the continuous reactor ranges from $1.0\times10^{-6}$ to $5.0\times10^{-1}$ mole of iron per kilogram olefin oligomerization solution,
  ii) the metal of the metal alkyl compound concentration in the continuous reactor ranges from $5.0\times10^{-3}$ to $1.0\times10^{3}$ mole of metal per kilogram olefin oligomerization solution,
  iii) the metal of the metal alkyl to iron of the transition metal complex molar ratio in the continuous reactor ranges from greater than 250:1 to 100,000:1, or
  iv) any combination thereof.

5. The process of claim 1, wherein the olefin consists essentially of ethylene, the transition metal compound comprises an iron(II) halide, the metal alkyl compound comprises an alumoxane, the olefin oligomer product is produced at a temperature ranging from 95° C. to 120° C. and an ethylene partial pressure ranging from 150 psig to 2,000 psig, and wherein the olefin oligomer product distribution K value for the transition metal complex is controlled in a range from 0.55 to 0.7 by adjusting an olefin oligomerization parameter selected from
  i) the iron of the transition metal complex concentration in the continuous reactor ranges from $1.0\times10^{-5}$ to $1.0\times10^{-2}$ mole of iron per kilogram olefin oligomerization solution,
  ii) the metal of the metal alkyl compound concentration in the continuous reactor ranges from $5.0\times10^{-2}$ to $1.0\times10^{1}$ mole of metal per kilogram olefin oligomerization solution,
  iii) the metal of the metal alkyl to iron of the transition metal complex molar ratio in the continuous reactor ranges from greater than 250:1 to 100,000:1, or
  iv) any combination thereof.

6. The process of claim 1 further comprising withdrawing a sample of the olefin oligomer product from the reactor prior to step b.

7. The process of claim 6 further comprising determining the olefin oligomer product distribution K value of the sample and determining the variance of the olefin oligomer product distribution K value of the sample from the range of 0.5 to 0.8.

8. An olefin oligomerization process comprising:
  a) contacting an olefin and a catalyst system comprising
    i) a transition metal complex comprising an iron compound complexed to a ligand comprising a pyridine bisimine group, and
    ii) a metal alkyl compound
  to form an olefin oligomer product in a continuous reactor, wherein the contacting is carried out at a temperature ranging from 90° C. to 150° C. with a catalyst productivity of greater than $1\times10^5$ g olefin oligomer product/mmol iron of the transition metal complex;
  b) selecting an olefin oligomer product distribution K value in a range from 0.5 to 0.8 for the transition metal complex from a correlation of the olefin oligomer product distribution K value with an olefin oligomerization parameter selected from
    i) an iron of the transition metal complex concentration in the continuous reactor,
    ii) a metal of the metal alkyl compound concentration in the continuous reactor,
    iii) a metal of the metal alkyl to iron of the transition metal complex molar ratio in the continuous reactor of greater than 250:1, or
    iv) any combination thereof; and
  c) adjusting, in the continuous reactor, the selected olefin oligomerization parameter to obtain the selected olefin oligomer product distribution K value.

9. The process of claim 8, wherein the iron compound comprises a halide, nitrate, sulfate, phosphate, halate, hydrocarboxide, carboxylate, or β-dionate and the metal alkyl compound comprises an aluminoxane.

10. The process of claim 9, wherein the olefin, the transition metal complex, and the aluminoxane are simultaneously introduced into the continuous reactor.

11. The process of claim 8, wherein the selected olefin oligomer product distribution K value is obtained by adjusting an olefin oligomerization parameter selected from
  i) the iron of the transition metal complex concentration in the continuous reactor ranges from $1.0\times10^{-6}$ to $5.0\times10^{-1}$ mole of iron per kilogram olefin oligomerization solution,
  ii) the metal of the metal alkyl compound concentration in the continuous reactor ranges from $5.0\times10^{-3}$ to $1.0\times10^{3}$ mole of metal per kilogram olefin oligomerization solution,
  iii) the metal of the metal alkyl to iron of the transition metal complex molar ratio in the continuous reactor ranges from greater than 250:1 to 100,000:1, or
  iv) any combination thereof.

12. The process of claim 8, wherein the olefin consists essentially of ethylene, the transition metal compound comprises an iron(II) halide, the metal alkyl compound comprises an alumoxane, the olefin oligomer product is produced at a temperature ranging from 90° C. to 120° C. and an ethylene partial pressure ranging from 150 psig to 2,000 psig, and wherein the selected olefin oligomer product distribution K value for the transition metal complex ranges from 0.55 to 0.7 and is obtained by adjusting an olefin oligomerization parameter selected from
  i) the iron of the transition metal complex concentration in the continuous reactor ranges from $1.0\times10^{-5}$ to $1.0\times10^{-2}$ mole of iron per kilogram olefin oligomerization solution, ii) the metal of the metal alkyl compound concentration in the continuous reactor ranges from $5.0 \times 10^{-2}$ to $1.0 \times 10^1$ mole of metal per kilogram olefin oligomerization solution, iii) the metal of the metal alkyl to iron of the transition metal complex molar ratio in the continuous reactor ranges from greater than 250:1 to 100,000:1, or iv) any combination thereof.

13. An olefin oligomerization process comprising:
a) correlating an olefin oligomer product distribution K value for oligomerizing an olefin in a continuous reactor in the presence of a catalyst system comprising
   1) an iron compound complexed to a ligand comprising a pyridine bisimine group, and
   2) a metal alkyl compound
   to an olefin oligomerization parameter selected from
   i) an iron of the transition metal complex concentration in the continuous reactor,
   ii) a metal of the metal alkyl compound concentration in the continuous reactor,
   iii) a metal of the metal alkyl to iron of the transition metal complex molar ratio in the continuous reactor of greater than 250:1, or
   iv) any combination thereof;
b) selecting an olefin oligomerization reactor K value; and
c) oligomerizing the olefin in the continuous reactor to form an olefin oligomer product at the selected olefin oligomer product distribution K value by setting, in the continuous reactor, the selected olefin oligomerization parameters necessary to achieve the selected olefin oligomer distribution K value, wherein the oligomerizing is carried out at a temperature ranging from 100° C. to 150° C. with a catalyst productivity of greater than $1 \times 10^5$ g olefin oligomer product/mmol iron of the transition metal complex.

14. The process of claim 13, wherein the iron compound comprises a halide, nitrate, sulfate, phosphate, halate, hydrocarboxide, carboxylate, or β-dionate and the metal alkyl compound comprises an aluminoxane.

15. The process of claim 14, wherein the olefin, the transition metal complex, and the aluminoxane are simultaneously introduced into the continuous reactor.

16. The process of claim 13, wherein the selected olefin oligomer product distribution K value ranges from 0.5 to 0.8 and the olefin is oligomerized at an olefin oligomerization parameter selected from
   i) the iron of the transition metal complex concentration in the continuous reactor ranges from $1.0 \times 10^{-6}$ to $5.0 \times 10^{-1}$ mole of iron per kilogram olefin oligomerization solution,
   ii) the metal of the metal alkyl compound concentration in the continuous reactor ranges from $5.0 \times 10^{-3}$ to $1.0 \times 10^3$ mole of metal per kilogram olefin oligomerization solution,
   iii) the metal of the metal alkyl to iron of the transition metal complex molar ratio in the continuous reactor ranges from greater than 250:1 to 100,000:1, or
   iv) any combination thereof.

17. The process of claim 13, wherein the olefin consists essentially of ethylene, the transition metal compound comprises an iron(II) halide, the metal alkyl compound comprises an alumoxane, the olefin oligomer product is produced at a temperature ranging from 100° C. to 120° C. and an ethylene partial pressure ranging from 150 psig to 2,000 psig, and wherein the selected olefin oligomer product distribution K value for the transition metal complex ranges from 0.55 to 0.7 and the olefin is oligomerized at an olefin oligomerization parameter selected from
   i) the iron of the transition metal complex concentration in the continuous reactor ranges from $1.0 \times 10^{-5}$ to $1.0 \times 10^{-2}$ mole of iron per kilogram olefin oligomerization solution,
   ii) the metal of the metal alkyl compound concentration in the continuous reactor ranges from $5.0 \times 10^{-2}$ to $1.0 \times 10^1$ mole of metal per kilogram olefin oligomerization solution,
   iii) the metal of the metal alkyl to iron of the transition metal complex molar ratio in the continuous reactor ranges from greater than 250:1 to 100,000:1, or
   iv) any combination thereof.

18. An oligomerization process comprising a) contacting an olefin and a catalyst system comprising i) a transition metal complex comprising an iron compound complexed to a ligand comprising a pyridine bisimine group, and ii) a metal alkyl compound, and b) forming an olefin oligomer product in a continuous reactor at a temperature ranging from 100° C. to 150° C. wherein the olefin oligomer product distribution K value is adjusted in the continuous reactor and wherein the process has a catalyst productivity of greater than $1 \times 10^5$ g olefin oligomer product/mmol iron of the transition metal complex, wherein the olefin is oligomerized at an olefin oligomerization parameter selected from
   i) an iron of the transition metal complex concentration in the continuous reactor ranges from $1.0 \times 10^{-6}$ to $5.0 \times 10^{-1}$ mole of iron per kilogram olefin oligomerization solution,
   ii) a metal of the metal alkyl compound concentration in the continuous reactor ranges from $5.0 \times 10^{-3}$ to $1.0 \times 10^{-1}$ mole of metal per kilogram olefin oligomerization solution,
   iii) a metal of the metal alkyl to iron of the transition metal complex molar ratio in the continuous reactor ranges from greater than 250:1 to 100,000:1, or
   iv) any combination thereof.

19. The process of claim 18, wherein the iron compound comprises a halide, nitrate, sulfate, phosphate, halate, hydrocarboxide, carboxylate, or β-dionate and the metal alkyl compound comprises an aluminoxane.

20. The process of claim 18, wherein the olefin oligomer product is produced at a temperature ranging from 100° C. to 120° C.

21. The process of claim 19, wherein the olefin, the transition metal complex, and the aluminoxane are simultaneously introduced into the continuous reactor.

22. The process of claim 18, wherein the olefin consists essentially of ethylene, the transition metal compound comprises an iron(II) halide, the metal alkyl compound comprises an alumoxane, the olefin oligomer product is produced at an ethylene partial pressure ranging from 150 psig to 2,000 psig, and wherein the olefin is oligomerized at an olefin oligomerization parameter selected from
   i) an iron of the transition metal complex concentration from $1.0 \times 10^{-5}$ to $1.0 \times 10^{-2}$ mole of iron per kilogram olefin oligomerization solution,
   ii) a metal of the metal alkyl compound concentration in the continuous reactor ranges from $5.0 \times 10^{-2}$ to $1.0 \times 10^1$ mole of metal per kilogram olefin oligomerization solution, iii) a metal of the metal alkyl to iron of the transition metal complex molar ratio in the continuous reactor ranges from greater than 250:1 to 100,000:1, or
iv) any combination thereof.

* * * * *